(12) United States Patent
Houghton et al.

(10) Patent No.: US 6,312,889 B1
(45) Date of Patent: *Nov. 6, 2001

(54) COMBINATIONS OF HEPATITIS C VIRUS (HCV) ANTIGENS FOR USE IN IMMUNOASSAYS FOR ANTI-HCV ANTIBODIES

(75) Inventors: Michael Houghton, Danville; Qui-Lim Choo, El Cerrito; George Kuo, San Francisco, all of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/440,549

(22) Filed: May 12, 1995

Related U.S. Application Data

(63) Continuation of application No. 07/910,760, filed on Jul. 7, 1992, now Pat. No. 5,683,864, which is a continuation-in-part of application No. 07/504,352, filed on Apr. 4, 1990, now abandoned.

(51) Int. Cl.[7] .......................... C12Q 1/70; G01N 33/543; G01N 33/545; C07K 14/18
(52) U.S. Cl. .............................. 435/5; 436/518; 436/531; 436/820; 530/350
(58) Field of Search .............................. 435/5, 7.92, 7.95, 435/69.3; 436/820, 518, 531; 530/826, 350

(56) References Cited

U.S. PATENT DOCUMENTS

| | | | |
|---|---|---|---|
| 4,464,474 | 8/1984 | Coursaget | 436/513 |
| 4,701,421 | 10/1987 | Kupers | 436/518 |
| 5,106,726 | 4/1992 | Wang | 435/5 |
| 5,308,750 | 5/1994 | Mehta et al. | 435/5 |
| 5,350,671 | 9/1994 | Houghton et al. | 435/5 |
| 5,436,126 | 7/1995 | Wang et al. | 435/5 |

FOREIGN PATENT DOCUMENTS

| | | |
|---|---|---|
| 0318216 | 5/1989 | (EP) . |
| 0363025 | 4/1990 | (EP) . |
| 0468527 | 1/1992 | (EP) . |
| 0484787 | 5/1992 | (EP) . |
| 0472207 | 6/1992 | (EP) . |
| 2212511 | 7/1989 | (GB) . |
| 2239245 | 6/1991 | (GB) . |
| 4054197 | 2/1992 | (JP) . |
| 4159298 | 6/1992 | (JP) . |
| WO 90/00597 | 1/1990 | (WO) . |
| WO 91/14779 | 10/1991 | (WO) . |
| WO 91/15574 | 10/1991 | (WO) . |
| WO 92/10514 | 6/1992 | (WO) . |
| WO 92/17493 | 10/1992 | (WO) . |

OTHER PUBLICATIONS

Bradley et al., Posttransfusion Non–A, Non–B Hepatitis in Chimpanzees Physicochemical Evidence That the Tubule–Forming Agent Is a Small, Enveloped Virus. Gastroenterology 88:773–779, 1985.*

Choo et al., "Isolation of a cDNA clone derived from a blood borne non–A, non–B viral hepatitis genome" *Science* (1989) 244:359–362.

Geysen et al., "Use of peptide synthesis to probe viral antigens for epitopes to a resolution of a single amino acid" *Proc. Natl. Acad. Sci. USA* (1984) 81:3998–4002.

Kuo et al., "An assay for circulating antibodies to a major etiologic virus of human non–A, non–B hepatitis" *Science* (1989) 244:362–264.

Krawczynski et al., "Hepatitis C virus antigen in hepatocytes: Immunomorphologic detection and identification" *Gastroenterology* (1992) 103:622–629.

Saito et al., "Performance of an enzyme–linked immunosorbent system for antibodies to hepatitis C virus with two new antigens (c11/c7)" *Clin. Chem.* (1992) 38(12):2434–2439.

Sällberg et al., Immunodominant regions within the hepatitis C virus core and putative matrix proteins *J. Clin. Microbiol.* (1992) 30(8):1989–1994.

* cited by examiner

Primary Examiner—Donna C. Wortman
(74) Attorney, Agent, or Firm—Gladys H. Monroy; Alisa A. Harbin; Robert P. Blackburn

(57) ABSTRACT

Combinations of HCV antigens that have a broader range of immunological reactivity than any single HCV antigen. The combinations consist of an antigen from the C domain of the HCV polyprotein, and at least one additional HCV antigen from either the NS3 domain, the NS4 domain, the S domain, or the NS5 domain, and are in the form of a fusion protein, a simple physical mixture, or the individual antigens commonly bound to a solid matrix.

17 Claims, 19 Drawing Sheets

```
                                                    -341  GCCAGCCCCCTGATGGGGGCGA
                                                          CGGTCGGGGGACTACCCCCGCT

-319  CACTCCACCATGAATCACTCCCCTGTGAGGAACTACTGTCTTCACGCAGAAAGCGTCTAG
      GTGAGGTGGTACTTAGTGAGGGGACACTCCTTGATGACAGAAGTGCGTCTTTCGCAGATC

-259  CCATGGCGTTAGTATGAGTGTCGTGCAGCCTCCAGGACCCCCCCTCCCGGGAGAGCCATA
      GGTACCGCAATCATACTCACAGCACGTCGGAGGTCCTGGGGGGAGGGCCCTCTCGGTAT

-199  GTGGTCTGCGGAACCGGTGAGTACACCGGAATTGCCAGGACGACCGGGTCCTTTCTTGGA
      CACCAGACGCCTTGGCCACTCATGTGGCCTTAACGGTCCTGCTGGCCCAGGAAAGAACCT

-139  TCAACCCGCTCAATGCCTGGAGATTTGGGCGTGCCCCCGCAAGACTGCTAGCCGAGTAGT
      AGTTGGGCGAGTTACGGACCTCTAAACCCGCACGGGGGCGTTCTGACGATCGGCTCATCA

- 79  GTTGGGTCGCGAAAGGCCTTGTGGTACTGCCTGATAGGGTGCTTGCGAGTGCCCCGGGAG
      CAACCCAGCGCTTTCCGGAACACCATGACGGACTATCCCACGAACGCTCACGGGGCCCTC

- 19  GTCTCGTAGACCGTGCACC
      CAGAGCATCTGGCACGTGG
                                      Arg  Thr
      ---  MetSerThrAsnProLysProGlnLysLysAsnLysArgAsnThrAsnArgArgProGln
   1  ATGAGCACGAATCCTAAACCTCAAAAAAAAAACAAACGTAACACCAACCGTCGCCCACAG
      TACTCGTGCTTAGGATTTGGAGTTTTTTTTTTGTTTGCATTGTGGTTGGCAGCGGGTGTC

AspValLysPheProGlyGlyGlyGlnIleValGlyGlyValTyrLeuLeuProArgArg
  61  GACGTCAAGTTCCCGGGTGGCGGTCAGATCGTTGGTGGAGTTTACTTGTTGCCGCGCAGG
      CTGCAGTTCAAGGGCCCACCGCCAGTCTAGCAACCACCTCAAATGAACAACGGCGCGTCC

GlyProArgLeuGlyValArgAlaThrArgLysThrSerGluArgSerGlnProArgGly
 121  GGCCCTAGATTGGGTGTGCGCGCGACGAGAAAGACTTCCGAGCGGTCGCAACCTCGAGGT
      CCGGGATCTAACCCACACGCGCGCTGCTCTTTCTGAAGGCTCGCCAGCGTTGGAGCTCCA

ArgArgGlnProIleProLysAlaArgArgProGluGlyArgThrTrpAlaGlnProGly
 181  AGACGTCAGCCTATCCCCAAGGCTCGTCGGCCCGAGGGCAGGACCTGGGCTCAGCCCGGG
      TCTGCAGTCGGATAGGGGTTCCGAGCAGCCGGGCTCCCGTCCTGGACCCGAGTCGGGCCC

TyrProTrpProLeuTyrGlyAsnGluGlyCysGlyTrpAlaGlyTrpLeuLeuSerPro
 241  TACCCTTGGCCCCTCTATGGCAATGAGGGCTGCGGGTGGGCGGGATGGCTCCTGTCTCCC
      ATGGGAACCGGGGAGATACCGTTACTCCCGACGCCCACCCGCCCTACCGAGGACAGAGGG

ArgGlySerArgProSerTrpGlyProThrAspProArgArgArgSerArgAsnLeuGly
 301  CGTGGCTCTCGGCCTAGCTGGGGCCCCACAGACCCCCGGCGTAGGTCGCGCAATTTGGGT
      GCACCGAGAGCCGGATCGACCCCGGGGTGTCTGGGGCCGCATCCAGCGCGTTAAACCCA

LysValIleAspThrLeuThrCysGlyPheAlaAspLeuMetGlyTyrIleProLeuVal
 361  AAGGTCATCGATACCCTTACGTGCGGCTTCGCCGACCTCATGGGGTACATACCGCTCGTC
      TTCCAGTAGCTATGGGAATGCACGCCGAAGCGGCTGGAGTACCCCATGTATGGCGAGCAG

GlyAlaProLeuGlyGlyAlaAlaArgAlaLeuAlaHisGlyValArgValLeuGluAsp
 421  GGCGCCCCTCTTGGAGGCGCTGCCAGGGCCCTGGCGCATGGCGTCCGGGTTCTGGAAGAC
      CCGCGGGGAGAACCTCCGCGACGGTCCCGGGACCGCGTACCGCAGGCCCAAGACCTTCTG
```

FIG. IA

```
                          Thr
       GlyValAsnTyrAlaThrGlyAsnLeuProGlyCysSerPheSerIlePheLeuLeuAla
481    GGCGTGAACTATGCAACAGGGAACCTTCCTGGTTGCTCTTTCTCTATCTTCCTTCTGGCC
       CCGCACTTGATACGTTGTCCCTTGGAAGGACCAACGAGAAAGAGATAGAAGGAAGACCGG

LeuLeuSerCysLeuThrValProAlaSerAlaTyrGlnValArgAsnSerThrGlyLeu
541    CTGCTCTCTTGCTTGACTGTGCCCGCTTCGGCCTACCAAGTGCGCAACTCCACGGGGCTT
       GACGAGAGAACGAACTGACACGGGCGAAGCCGGATGGTTCACGCGTTGAGGTGCCCCGAA

TyrHisValThrAsnAspCysProAsnSerSerIleValTyrGluAlaAlaAspAlaIle
601    TACCACGTCACCAATGATTGCCCTAACTCGAGTATTGTGTACGAGGCGGCCGATGCCATC
       ATGGTGCAGTGGTTACTAACGGGATTGAGCTCATAACACATGCTCCGCCGGCTACGGTAG

LeuHisThrProGlyCysValProCysValArgGluGlyAsnAlaSerArgCysTrpVal
661    CTGCACACTCCGGGGTGCGTCCCTTGCGTTCGTGAGGGCAACGCCTCGAGGTGTTGGGTG
       GACGTGTGAGGCCCCACGCAGGGAACGCAAGCACTCCCGTTGCGGAGCTCCACAACCCAC

AlaMetThrProThrValAlaThrArgAspGlyLysLeuProAlaThrGlnLeuArgArg
721    GCGATGACCCCTACGGTGGCCACCAGGGATGGCAAACTCCCCGCGACGCAGCTTCGACGT
       CGCTACTGGGGATGCCACCGGTGGTCCCTACCGTTTGAGGGGCGCTGCGTCGAAGCTGCA

HisIleAspLeuLeuValGlySerAlaThrLeuCysSerAlaLeuTyrValGlyAspLeu
781    CACATCGATCTGCTTGTCGGGAGCGCCACCCTCTGTTCGGCCCTCTACGTGGGGGACCTA
       GTGTAGCTAGACGAACAGCCCTCGCGGTGGGAGACAAGCCGGGAGATGCACCCCCTGGAT

CysGlySerValPheLeuValGlyGlnLeuPheThrPheSerProArgArgHisTrpThr
841    TGCGGGTCTGTCTTTCTTGTCGGCCAACTGTTCACCTTCTCTCCCAGGCGCCACTGGACG
       ACGCCCAGACAGAAAGAACAGCCGGTTGACAAGTGGAAGAGAGGGTCCGCGGTGACCTGC

ThrGlnGlyCysAsnCysSerIleTyrProGlyHisIleThrGlyHisArgMetAlaTrp
901    ACGCAAGGTTGCAATTGCTCTATCTATCCCGGCCATATAACGGGTCACCGCATGGCATGG
       TGCGTTCCAACGTTAACGAGATAGATAGGGCCGGTATATTGCCCAGTGGCGTACCGTACC

Val
       AspMetMetMetAsnTrpSerProThrThrAlaLeuValMetAlaGlnLeuLeuArgIle
961    GATATGATGATGAACTGGTCCCCTACGACGGCGTTGGTAATGGCTCAGCTGCTCCGGATC
       CTATACTACTACTTGACCAGGGGATGCTGCCGCAACCATTACCGAGTCGACGAGGCCTAG

ProGlnAlaIleLeuAspMetIleAlaGlyAlaHisTrpGlyValLeuAlaGlyIleAla
1021   CCACAAGCCATCTTGGACATGATCGCTGGTGCTCACTGGGGAGTCCTGGCGGGCATAGCG
       GGTGTTCGGTAGAACCTGTACTAGCGACCACGAGTGACCCCTCAGGACCGCCCGTATCGC

TyrPheSerMetValGlyAsnTrpAlaLysValLeuValValLeuLeuLeuPheAlaGly
1081   TATTTCTCCATGGTGGGGAACTGGGCGAAGGTCCTGGTATTGCTGCTGCTATTTGCCGGC
       ATAAAGAGGTACCACCCCTTGACCCGCTTCCAGGACCATAACGACGACGATAAACGGCCG

ValAspAlaGluThrHisValThrGlyGlySerAlaGlyHisThrValSerGlyPheVal
1141   GTCGACGCGGAAACCCACGTCACCGGGGGAAGTGCCGGCCACACTGTGTCTGGATTTGTT
       CAGCTGCGCCTTTGGGTGCAGTGGCCCCCTTCACGGCCGGTGTGACACAGACCTAAACAA

SerLeuLeuAlaProGlyAlaLysGlnAsnValGlnLeuIleAsnThrAsnGlySerTrp
1201   AGCCTCCTCGCACCAGGCGCCAAGCAGAACGTCCAGCTGATCAACACCAACGGCAGTTGG
       TCGGAGGAGCGTGGTCCGCGGTTCGTCTTGCAGGTCGACTAGTTGTGGTTGCCGTCAACC
```

FIG. IB

```
            HisLeuAsnSerThrAlaLeuAsnCysAsnAspSerLeuAsnThrGlyTrpLeuAlaGly
1261  CACCTCAATAGCACGGCCCTGAACTGCAATGATAGCCTCAACACCGGCTGGTTGGCAGGG
      GTGGAGTTATCGTGCCGGGACTTGACGTTACTATCGGAGTTGTGGCCGACCAACCGTCCC

LeuPheTyrHisHisLysPheAsnSerSerGlyCysProGluArgLeuAlaSerCysArg
1321  CTTTTCTATCACCACAAGTTCAACTCTTCAGGCTGTCCTGAGAGGCTAGCCAGCTGCCGA
      GAAAAGATAGTGGTGTTCAAGTTGAGAAGTCCGACAGGACTCTCCGATCGGTCGACGGCT

ProLeuThrAspPheAspGlnGlyTrpGlyProIleSerTyrAlaAsnGlySerGlyPro
1381  CCCCTTACCGATTTTGACCAGGGCTGGGGCCCTATCAGTTATGCCAACGGAAGCGGCCCC
      GGGGAATGGCTAAAACTGGTCCCGACCCCGGGATAGTCAATACGGTTGCCTTCGCCGGGG

AspGlnArgProTyrCysTrpHisTyrProProLysProCysGlyIleValProAlaLys
1441  GACCAGCGCCCCTACTGCTGGCACTACCCCCCAAAACCTTGCGGTATTGTGCCCGCGAAG
      CTGGTCGCGGGGATGACGACCGTGATGGGGGGTTTTGGAACGCCATAACACGGGCGCTTC

SerValCysGlyProValTyrCysPheThrProSerProValValValGlyThrThrAsp
1501  AGTGTGTGTGGTCCGGTATATTGCTTCACTCCCAGCCCGTGGTGGTGGGAACGACCGAC
      TCACACACACCAGGCCATATAACGAAGTGAGGGTCGGGGCACCACCACCCTTGCTGGCTG

ArgSerGlyAlaProThrTyrSerTrpGlyGluAsnAspThrAspValPheValLeuAsn
1561  AGGTCGGGCGCGCCCACCTACAGCTGGGGTGAAAATGATACGGACGTCTTCGTCCTTAAC
      TCCAGCCCGCGCGGGTGGATGTCGACCCCACTTTTACTATGCCTGCAGAAGCAGGAATTG

AsnThrArgProProLeuGlyAsnTrpPheGlyCysThrTrpMetAsnSerThrGlyPhe
1621  AATACCAGGCCACCGCTGGGCAATTGGTTCGGTTGTACCTGGATGAACTCAACTGGATTC
      TTATGGTCCGGTGGCGACCCGTTAACCAAGCCAACATGGACCTACTTGAGTTGACCTAAG

ThrLysValCysGlyAlaProProCysValIleGlyGlyAlaGlyAsnAsnThrLeuHis
1681  ACCAAAGTGTGCGGAGCGCCTCCTTGTGTCATCGGAGGGGCGGGCAACAACACCCTGCAC
      TGGTTTCACACGCCTCGCGGAGGAACACAGTAGCCTCCCCGCCCGTTGTTGTGGGACGTG

CysProThrAspCysPheArgLysHisProAspAlaThrTyrSerArgCysGlySerGly
1741  TGCCCCACTGATTGCTTCCGCAAGCATCCGGACGCCACATACTCTCGGTGCGGCTCCGGT
      ACGGGGTGACTAACGAAGGCGTTCGTAGGCCTGCGGTGTATGAGAGCCACGCCGAGGCCA

Ile
            ProTrpLeuThrProArgCysLeuValAspTyrProTyrArgLeuTrpHisTyrProCys
1801  CCCTGGATCACACCCAGGTGCCTGGTCGACTACCCGTATAGGCTTTGGCATTATCCTTGT
      GGGACCTAGTGTGGGTCCACGGACCAGCTGATGGGCATATCCGAAACCGTAATAGGAACA

ThrIleAsnTyrThrIlePheLysIleArgMetTyrValGlyGlyValGluHisArgLeu
1861  ACCATCAACTACACCATATTTAAAATCAGGATGTACGTGGGAGGGGTCGAACACAGGCTG
      TGGTAGTTGATGTGGTATAAATTTTAGTCCTACATGCACCCTCCCCAGCTTGTGTCCGAC

GluAlaAlaCysAsnTrpThrArgGlyGluArgCysAspLeuGluAspArgAspArgSer
1921  GAAGCTGCCTGCAACTGGACGCGGGGCGAACGTTGCGATCTGGAAGACAGGGACAGGTCC
      CTTCGACGGACGTTGACCTGCGCCCCGCTTGCAACGCTAGACCTTCTGTCCCTGTCCAGG

GluLeuSerProLeuLeuLeuThrThrThrGlnTrpGlnValLeuProCysSerPheThr
1981  GAGCTCAGCCCGTTACTGCTGACCACTACACAGTGGCAGGTCCTCCCGTGTTCCTTCACA
      CTCGAGTCGGGCAATGACGACTGGTGATGTGTCACCGTCCAGGAGGGCACAAGGAAGTGT
```

FIG. 1C

```
     ThrLeuProAlaLeuSerThrGlyLeuIleHisLeuHisGlnAsnIleValAspValGln
2041 ACCCTACCAGCCTTGTCCACCGGCCTCATCCACCTCCACCAGAACATTGTGGACGTGCAG
     TGGGATGGTCGGAACAGGTGGCCGGAGTAGGTGGAGGTGGTCTTGTAACACCTGCACGTC

TyrLeuTyrGlyValGlySerSerIleAlaSerTrpAlaIleLysTrpGluTyrValVal
2101 TACTTGTACGGGGTGGGGTCAAGCATCGCGTCCTGGGCCATTAAGTGGGAGTACGTCGTT
     ATGAACATGCCCCACCCCAGTTCGTAGCGCAGGACCCGGTAATTCACCCTCATGCAGCAA

LeuLeuPheLeuLeuLeuAlaAspAlaArgValCysSerCysLeuTrpMetMetLeuLeu
2161 CTCCTGTTCCTTCTGCTTGCAGACGCGCGCGTCTGCTCCTGCTTGTGGATGATGCTACTC
     GAGGACAAGGAAGACGAACGTCTGCGCGCGCAGACGAGGACGAACACCTACTACGATGAG

IleSerGlnAlaGluAlaAlaLeuGluAsnLeuValIleLeuAsnAlaAlaSerLeuAla
2221 ATATCCCAAGCGGAGGCGGCTTTGGAGAACCTCGTAATACTTAATGCAGCATCCCTGGCC
     TATAGGGTTCGCCTCCGCCGAAACCTCTTGGAGCATTATGAATTACGTCGTAGGGACCGG

GlyThrHisGlyLeuValSerPheLeuValPhePheCysPheAlaTrpTyrLeuLysGly
2281 GGGACGCACGGTCTTGTATCCTTCCTCGTGTTCTTCTGCTTTGCATGGTATTTGAAGGGT
     CCCTGCGTGCCAGAACATAGGAAGGAGCACAAGAAGACGAAACGTACCATAAACTTCCCA

LysTrpValProGlyAlaValTyrThrPheTyrGlyMetTrpProLeuLeuLeuLeuLeu
2341 AAGTGGGTGCCCGGAGCGGTCTACACCTTCTACGGGATGTGGCCTCTCCTCCTGCTCCTG
     TTCACCCACGGGCCTCGCCAGATGTGGAAGATGCCCTACACCGGAGAGGAGGACGAGGAC

LeuAlaLeuProGlnArgAlaTyrAlaLeuAspThrGluValAlaAlaSerCysGlyGly
2401 TTGGCGTTGCCCCAGCGGGCGTACGCGCTGGACACGGAGGTGGCCGCGTCGTGTGGCGGT
     AACCGCAACGGGGTCGCCCGCATGCGCGACCTGTGCCTCCACCGGCGCAGCACACCGCCA

ValValLeuValGlyLeuMetAlaLeuThrLeuSerProTyrTyrLysArgTyrIleSer
2461 GTTGTTCTCGTCGGGTTGATGGCGCTGACTCTGTCACCATATTACAAGCGCTATATCAGC
     CAACAAGAGCAGCCCAACTACCGCGACTGAGACAGTGGTATAATGTTCGCGATATAGTCG (Asn)
     TrpCysLeuTrpTrpLeuGlnTyrPheLeuThrArgValGluAlaGlnLeuHisValTrp
2521 TGGTGCTTGTGGTGGCTTCAGTATTTTCTGACCAGAGTGGAAGCGCAACTGCACGTGTGG
     ACCACGAACACCACCGAAGTCATAAAAGACTGGTCTCACCTTCGCGTTGACGTGCACACC

IleProProLeuAsnValArgGlyGlyArgAspAlaValIleLeuLeuMetCysAlaVal
2581 ATTCCCCCCCTCAACGTCCGAGGGGGGCGCGACGCCGTCATCTTACTCATGTGTGCTGTA
     TAAGGGGGGGAGTTGCAGGCTCCCCCCGCGCTGCGGCAGTAGAATGAGTACACACGACAT

HisProThrLeuValPheAspIleThrLysLeuLeuLeuAlaValPheGlyProLeuTrp
2641 CACCCGACTCTGGTATTTGACATCACCAAATTGCTGCTGGCCGTCTTCGGACCCCTTTGG
     GTGGGCTGAGACCATAAACTGTAGTGGTTTAACGACGACCGGCAGAAGCCTGGGGAAACC

IleLeuGlnAlaSerLeuLeuLysValProTyrPheValArgValGlnGlyLeuLeuArg
2701 ATTCTTCAAGCCAGTTTGCTTAAAGTACCCTACTTTGTGCGCGTCCAAGGCCTTCTCCGG
     TAAGAAGTTCGGTCAAACGAATTTCATGGGATGAAACACGCGCAGGTTCCGGAAGAGGCC

PheCysAlaLeuAlaArgLysMetIleGlyGlyHisTyrValGlnMetValIleIleLys
2761 TTCTGCGCGTTAGCGCGGAAGATGATCGGAGGCCATTACGTGCAAATGGTCATCATTAAG
     AAGACGCGCAATCGCGCCTTCTACTAGCCTCCGGTAATGCACGTTTACCAGTAGTAATTC
```

FIG. ID

```
         LeuGlyAlaLeuThrGlyThrTyrValTyrAsnHisLeuThrProLeuArgAspTrpAla
2821     TTAGGGGCGCTTACTGGCACCTATGTTTATAACCATCTCACTCCTCTTCGGGACTGGGCG
         AATCCCCGCGAATGACCGTGGATACAAATATTGGTAGAGTGAGGAGAAGCCCTGACCCGC

HisAsnGlyLeuArgAspLeuAlaValAlaValGluProValValPheSerGlnMetGlu
2881     CACAACGGCTTGCGAGATCTGGCCGTGGCTGTAGAGCCAGTCGTCTTCTCCCAAATGGAG
         GTGTTGCCGAACGCTCTAGACCGGCACCGACATCTCGGTCAGCAGAAGAGGGTTTACCTC

ThrLysLeuIleThrTrpGlyAlaAspThrAlaAlaCysGlyAspIleIleAsnGlyLeu
2941     ACCAAGCTCATCACGTGGGGGGCAGATACCGCCGCGTGCGGTGACATCATCAACGGCTTG
         TGGTTCGAGTAGTGCACCCCCCGTCTATGGCGGCGCACGCCACTGTAGTAGTTGCCGAAC

ProValSerAlaArgArgGlyArgGluIleLeuLeuGlyProAlaAspGlyMetValSer
3001     CCTGTTTCCGCCCGCAGGGGCCGGGAGATACTGCTCGGGCCAGCCGATGGAATGGTCTCC
         GGACAAAGGCGGGCGTCCCCGGCCCTCTATGACGAGCCCGGTCGGCTACCTTACCAGAGG

LysGlyTrpArgLeuLeuAlaProIleThrAlaTyrAlaGlnGlnThrArgGlyLeuLeu
3061     AAGGGGTGGAGGTTGCTGGCGCCCATCACGGCGTACGCCCAGCAGACAAGGGGCCTCCTA
         TTCCCCACCTCCAACGACCGCGGGTAGTGCCGCATGCGGGTCGTCTGTTCCCCGGAGGAT

GlyCysIleIleThrSerLeuThrGlyArgAspLysAsnGlnValGluGlyGluValGln
3121     GGGTGCATAATCACCAGCCTAACTGGCCGGGACAAAAACCAAGTGGAGGGTGAGGTCCAG
         CCCACGTATTAGTGGTCGGATTGACCGGCCCTGTTTTTGGTTCACCTCCCACTCCAGGTC

IleValSerThrAlaAlaGlnThrPheLeuAlaThrCysIleAsnGlyValCysTrpThr
3181     ATTGTGTCAACTGCTGCCCAAACCTTCCTGGCAACGTGCATCAATGGGGTGTGCTGGACT
         TAACACAGTTGACGACGGGTTTGGAAGGACCGTTGCACGTAGTTACCCCACACGACCTGA

ValTyrHisGlyAlaGlyThrArgThrIleAlaSerProLysGlyProValIleGlnMet
3241     GTCTACCACGGGGCCGGAACGAGGACCATCGCGTCACCCAAGGGTCCTGTCATCCAGATG
         CAGATGGTGCCCCGGCCTTGCTCCTGGTAGCGCAGTGGGTTCCCAGGACAGTAGGTCTAC

Ser     Thr
         TyrThrAsnValAspGlnAspLeuValGlyTrpProAlaProGlnGlySerArgSerLeu
3301     TATACCAATGTAGACCAAGACCTTGTGGGCTGGCCCGCTCCGCAAGGTAGCCGCTCATTG
         ATATGGTTACATCTGGTTCTGGAACACCCGACCGGGCGAGGCGTTCCATCGGCGAGTAAC

ThrProCysThrCysGlySerSerAspLeuTyrLeuValThrArgHisAlaAspValIle
3361     ACACCCTGCACTTGCGGCTCCTCGGACCTTTACCTGGTCACGAGGCACGCCGATGTCATT
         TGTGGGACGTGAACGCCGAGGAGCCTGGAAATGGACCAGTGCTCCGTGCGGCTACAGTAA

ProValArgArgArgGlyAspSerArgGlySerLeuLeuSerProArgProIleSerTyr
3421     CCCGTGCGCCGGCGGGGTGATAGCAGGGGCAGCCTGCTGTCGCCCCGGCCCATTTCCTAC
         GGGCACGCGGCCGCCCCACTATCGTCCCCGTCGGACGACAGCGGGGCCGGGTAAAGGATG

LeuLysGlySerSerGlyGlyProLeuLeuCysProAlaGlyHisAlaValGlyIlePhe
3481     TTGAAAGGCTCCTCGGGGGGTCCGCTGTTGTGCCCCGCGGGGCACGCCGTGGGCATATTT
         AACTTTCCGAGGAGCCCCCCAGGCGACAACACGGGGCGCCCCGTGCGGCACCCGTATAAA

ArgAlaAlaValCysThrArgGlyValAlaLysAlaValAspPheIleProValGluAsn
3541     AGGGCCGCGGTGTGCACCCGTGGAGTGGCTAAGGCGGTGGACTTTATCCCTGTGGAGAAC
         TCCCGGCGCCACACGTGGGCACCTCACCGATTCCGCCACCTGAAATAGGGACACCTCTTG
```

FIG. 1E

```
              LeuGluThrThrMetArgSerProValPheThrAspAsnSerSerProProValValPro
     3601     CTAGAGACAACCATGAGGTCCCCGGTGTTCACGGATAACTCCTCTCCACCAGTAGTGCCC
              GATCTCTGTTGGTACTCCAGGGGCCACAAGTGCCTATTGAGGAGAGGTGGTCATCACGGG

GlnSerPheGlnValAlaHisLeuHisAlaProThrGlySerGlyLysSerThrLysVal
     3661     CAGAGCTTCCAGGTGGCTCACCTCCATGCTCCCACAGGCAGCGGCAAAAGCACCAAGGTC
              GTCTCGAAGGTCCACCGAGTGGAGGTACGAGGGTGTCCGTCGCCGTTTTCGTGGTTCCAG

ProAlaAlaTyrAlaAlaGlnGlyTyrLysValLeuValLeuAsnProSerValAlaAla
     3721     CCGGCTGCATATGCAGCTCAGGGCTATAAGGTGCTAGTACTCAACCCCTCTGTTGCTGCA
              GGCCGACGTATACGTCGAGTCCCGATATTCCACGATCATGAGTTGGGGAGACAACGACGT

Leu
              ThrLeuGlyPheGlyAlaTyrMetSerLysAlaHisGlyIleAspProAsnIleArgThr
     3781     ACACTGGGCTTTGGTGCTTACATGTCCAAGGCTCATGGGATCGATCCTAACATCAGGACC
              TGTGACCCGAAACCACGAATGTACAGGTTCCGAGTACCCTAGCTAGGATTGTAGTCCTGG

GlyValArgThrIleThrThrGlySerProIleThrTyrSerThrTyrGlyLysPheLeu
     3841     GGGGTGAGAACAATTACCACTGGCAGCCCCATCACGTACTCCACCTACGGCAAGTTCCTT
              CCCCACTCTTGTTAATGGTGACCGTCGGGGTAGTGCATGAGGTGGATGCCGTTCAAGGAA

AlaAspGlyGlyCysSerGlyGlyAlaTyrAspIleIleIleCysAspGluCysHisSer
     3901     GCCGACGGCGGGTGCTCGGGGGGCGCTTATGACATAATAATTTGTGACGAGTGCCACTCC
              CGGCTGCCGCCCACGAGCCCCCCGCGAATACTGTATTATTAAACACTGCTCACGGTGAGG (Val)
              ThrAspAlaThrSerIleLeuGlyIleGlyThrValLeuAspGlnAlaGluThrAlaGly
     3961     ACGGATGCCACATCCATCTTGGGCATCGGCACTGTCCTTGACCAAGCAGAGACTGCGGGG
              TGCCTACGGTGTAGGTAGAACCCGTAGCCGTGACAGGAACTGGTTCGTCTCTGACGCCCC

AlaArgLeuValValLeuAlaThrAlaThrProProGlySerValThrValProHisPro
     4021     GCGAGACTGGTTGTGCTCGCCACCGCCACCCCTCCGGGCTCCGTCACTGTGCCCCATCCC
              CGCTCTGACCAACACGAGCGGTGGCGGTGGGGAGGCCCGAGGCAGTGACACGGGGTAGGG

AsnIleGluGluValAlaLeuSerThrThrGlyGluIleProPheTyrGlyLysAlaIle
     4081     AACATCGAGGAGGTTGCTCTGTCCACCACCGGAGAGATCCCTTTTTACGGCAAGGCTATC
              TTGTAGCTCCTCCAACGAGACAGGTGGTGGCCTCTCTAGGGAAAAATGCCGTTCCGATAG

ProLeuGluValIleLysGlyGlyArgHisLeuIlePheCysHisSerLysLysLysCys
     4141     CCCCTCGAAGTAATCAAGGGGGGGAGACATCTCATCTTCTGTCATTCAAAGAAGAAGTGC
              GGGGAGCTTCATTAGTTCCCCCCCTCTGTAGAGTAGAAGACAGTAAGTTTCTTCTTCACG

AspGluLeuAlaAlaLysLeuValAlaLeuGlyIleAsnAlaValAlaTyrTyrArgGly
     4201     GACGAACTCGCCGCAAAGCTGGTCGCATTGGGCATCAATGCCGTGGCCTACTACCGCGGT
              CTGCTTGAGCGGCGTTTCGACCAGCGTAACCCGTAGTTACGGCACCGGATGATGGCGCCA

LeuAspValSerValIleProThrSerGlyAspValValValValAlaThrAspAlaLeu
     4261     CTTGACGTGTCCGTCATCCCGACCAGCGGCGATGTTGTCGTCGTGGCAACCGATGCCCTC
              GAACTGCACAGGCAGTAGGGCTGGTCGCCGCTACAACAGCAGCACCGTTGGCTACGGGAG

Tyr
              MetThrGlyTyrThrGlyAspPheAspSerValIleAspCysAsnThrCysValThrGln
     4321     ATGACCGGCTATACCGGCGACTTCGACTCGGTGATAGACTGCAATACGTGTGTCACCCAG
              TACTGGCCGATATGGCCGCTGAAGCTGAGCCACTATCTGACGTTATGCACACAGTGGGTC
```

FIG. IF

```
                                                            (Ser)
         ThrValAspPheSerLeuAspProThrPheThrIleGluThrIleThrLeuProGlnAsp
4381     ACAGTCGATTTCAGCCTTGACCCTACCTTCACCATTGAGACAATCACGCTCCCCCAGGAT
         TGTCAGCTAAAGTCGGAACTGGGATGGAAGTGGTAACTCTGTTAGTGCGAGGGGGTCCTA

AlaValSerArgThrGlnArgArgGlyArgThrGlyArgGlyLysProGlyIleTyrArg
4441     GCTGTCTCCCGCACTCAACGTCGGGGCAGGACTGGCAGGGGGAAGCCAGGCATCTATAGA
         CGACAGAGGGCGTGAGTTGCAGCCCCGTCCTGACCGTCCCCCTTCGGTCCGTAGATATCT

PheValAlaProGlyGluArgProSerGlyMetPheAspSerSerValLeuCysGluCys
4501     TTTGTGGCACCGGGGGAGCGCCCTCCGGCATGTTCGACTCGTCCGTCCTCTGTGAGTGC
         AAACACCGTGGCCCCCTCGCGGGGAGGCCGTACAAGCTGAGCAGGCAGGAGACACTCACG

TyrAspAlaGlyCysAlaTrpTyrGluLeuThrProAlaGluThrThrValArgLeuArg
4561     TATGACGCAGGCTGTGCTTGGTATGAGCTCACGCCCGCCGAGACTACAGTTAGGCTACGA
         ATACTGCGTCCGACACGAACCATACTCGAGTGCGGGCGGCTCTGATGTCAATCCGATGCT

AlaTyrMetAsnThrProGlyLeuProValCysGlnAspHisLeuGluPheTrpGluGly
4621     GCGTACATGAACACCCCGGGGCTTCCCGTGTGCCAGGACCATCTTGAATTTTGGGAGGGC
         CGCATGTACTTGTGGGGCCCCGAAGGGCACACGGTCCTGGTAGAACTTAAAACCCTCCCG

ValPheThrGlyLeuThrHisIleAspAlaHisPheLeuSerGlnThrLysGlnSerGly
4681     GTCTTTACAGGCCTCACTCATATAGATGCCCACTTTCTATCCCAGACAAAGCAGAGTGGG
         CAGAAATGTCCGGAGTGAGTATATCTACGGGTGAAAGATAGGGTCTGTTTCGTCTCACCC

GluAsnLeuProTyrLeuValAlaTyrGlnAlaThrValCysAlaArgAlaGlnAlaPro
4741     GAGAACCTTCCTTACCTGGTAGCGTACCAAGCCACCGTGTGCGCTAGGGCTCAAGCCCCT
         CTCTTGGAAGGAATGGACCATCGCATGGTTCGGTGGCACACGCGATCCCGAGTTCGGGGA

ProProSerTrpAspGlnMetTrpLysCysLeuIleArgLeuLysProThrLeuHisGly
4801     CCCCCATCGTGGGACCAGATGTGGAAGTGTTTGATTCGCCTCAAGCCCACCCTCCATGGG
         GGGGGTAGCACCCTGGTCTACACCTTCACAAACTAAGCGGAGTTCGGGTGGGAGGTACCC

ProThrProLeuLeuTyrArgLeuGlyAlaValGlnAsnGluIleThrLeuThrHisPro
4861     CCAACACCCCTGCTATACAGACTGGGCGCTGTTCAGAATGAAATCACCCTGACGCACCCA
         GGTTGTGGGGACGATATGTCTGACCCGCGACAAGTCTTACTTTAGTGGGACTGCGTGGGT

ValThrLysTyrIleMetThrCysMetSerAlaAspLeuGluValValThrSerThrTrp
4921     GTCACCAAATACATCATGACATGCATGTCGGCCGACCTGGAGGTCGTCACGAGCACCTGG
         CAGTGGTTTATGTAGTACTGTACGTACAGCCGGCTGGACCTCCAGCAGTGCTCGTGGACC

ValLeuValGlyGlyValLeuAlaAlaLeuAlaAlaTyrCysLeuSerThrGlyCysVal
4981     GTGCTCGTTGGCGGCGTCCTGGCTGCTTTGGCCGCGTATTGCCTGTCAACAGGCTGCGTG
         CACGAGCAACCGCCGCAGGACCGACGAAACCGGCGCATAACGGACAGTTGTCCGACGCAC

ValIleValGlyArgValValLeuSerGlyLysProAlaIleIleProAspArgGluVal
5041     GTCATAGTGGGCAGGGTCGTCTTGTCCGGGAAGCCGGCAATCATACCTGACAGGGAAGTC
         CAGTATCACCCGTCCCAGCAGAACAGGCCCTTCGGCCGTTAGTATGGACTGTCCCTTCAG

LeuTyrArgGluPheAspGluMetGluGluCysSerGlnHisLeuProTyrIleGluGln
5101     CTCTACCGAGAGTTCGATGAGATGGAAGAGTGCTCTCAGCACTTACCGTACATCGAGCAA
         GAGATGGCTCTCAAGCTACTCTACCTTCTCACGAGAGTCGTGAATGGCATGTAGCTCGTT
```

FIG. 1G

```
      GlyMetMetLeuAlaGluGlnPheLysGlnLysAlaLeuGlyLeuLeuGlnThrAlaSer
5161  GGGATGATGCTCGCCGAGCAGTTCAAGCAGAAGGCCCTCGGCCTCCTGCAGACCGCGTCC
      CCCTACTACGAGCGGCTCGTCAAGTTCGTCTTCCGGGAGCCGGAGGACGTCTGGCGCAGG

ArgGlnAlaGluValIleAlaProAlaValGlnThrAsnTrpGlnLysLeuGluThrPhe
5221  CGTCAGGCAGAGGTTATCGCCCCTGCTGTCCAGACCAACTGGCAAAAACTCGAGACCTTC
      GCAGTCCGTCTCCAATAGCGGGGACGACAGGTCTGGTTGACCGTTTTTGAGCTCTGGAAG

TrpAlaLysHisMetTrpAsnPheIleSerGlyIleGlnTyrLeuAlaGlyLeuSerThr
5281  TGGGCGAAGCATATGTGGAACTTCATCAGTGGGATACAATACTTGGCGGGCTTGTCAACG
      ACCCGCTTCGTATACACCTTGAAGTAGTCACCCTATGTTATGAACCGCCCGAACAGTTGC

LeuProGlyAsnProAlaIleAlaSerLeuMetAlaPheThrAlaAlaValThrSerPro
5341  CTGCCTGGTAACCCCGCCATTGCTTCATTGATGGCTTTTACAGCTGCTGTCACCAGCCCA
      GACGGACCATTGGGGCGGTAACGAAGTAACTACCGAAAATGTCGACGACAGTGGTCGGGT

LeuThrThrSerGlnThrLeuLeuPheAsnIleLeuGlyGlyTrpValAlaAlaGlnLeu
5401  CTAACCACTAGCCAAACCCTCCTCTTCAACATATTGGGGGGTGGGTGGCTGCCCAGCTC
      GATTGGTGATCGGTTTGGGAGGAGAAGTTGTATAACCCCCCCACCCACCGACGGGTCGAG

AlaAlaProGlyAlaAlaThrAlaPheValGlyAlaGlyLeuAlaGlyAlaAlaIleGly
5461  GCCGCCCCCGGTGCCGCTACTGCCTTTGTGGGCGCTGGCTTAGCTGGCGCCGCCATCGGC
      CGGCGGGGGCCACGGCGATGACGGAAACACCCGCGACCGAATCGACCGCGGCGGTAGCCG

SerValGlyLeuGlyLysValLeuIleAspIleLeuAlaGlyTyrGlyAlaGlyValAla
5521  AGTGTTGGACTGGGGAAGGTCCTCATAGACATCCTTGCAGGGTATGGCGCGGGCGTGGCG
      TCACAACCTGACCCCTTCCAGGAGTATCTGTAGGAACGTCCCATACCGCGCCCGCACCGC (Gly)
      GlyAlaLeuValAlaPheLysIleMetSerGlyGluValProSerThrGluAspLeuVal
5581  GGAGCTCTTGTGGCATTCAAGATCATGAGCGGTGAGGTCCCCTCCACGGAGGACCTGGTC
      CCTCGAGAACACCGTAAGTTCTAGTACTCGCCACTCCAGGGGAGGTGCCTCCTGGACCAG

AsnLeuLeuProAlaIleLeuSerProGlyAlaLeuValValGlyValValCysAlaAla
5641  AATCTACTGCCCGCCATCCTCTCGCCCGGAGCCCTCGTAGTCGGCGTGGTCTGTGCAGCA
      TTAGATGACGGGCGGTAGGAGAGCGGGCCTCGGGAGCATCAGCCGCACCAGACACGTCGT

IleLeuArgArgHisValGlyProGlyGluGlyAlaValGlnTrpMetAsnArgLeuIle
5701  ATACTGCGCCGGCACGTTGGCCCGGGCGAGGGGGCAGTGCAGTGGATGAACCGGCTGATA
      TATGACGCGGCCGTGCAACCGGGCCCGCTCCCCCGTCACGTCACCTACTTGGCCGACTAT

AlaPheAlaSerArgGlyAsnHisValSerProThrHisTyrValProGluSerAspAla
5761  GCCTTCGCCTCCCGGGGGAACCATGTTTCCCCCACGCACTACGTGCCGGAGAGCGATGCA
      CGGAAGCGGAGGGCCCCCTTGGTACAAAGGGGGTGCGTGATGCACGGCCTCTCGCTACGT (HisCys)
      AlaAlaArgValThrAlaIleLeuSerSerLeuThrValThrGlnLeuLeuArgArgLeu
5821  GCTGCCCGCGTCACTGCCATACTCAGCAGCCTCACTGTAACCCAGCTCCTGAGGCGACTG
      CGACGGGCGCAGTGACGGTATGAGTCGTCGGAGTGACATTGGGTCGAGGACTCCGCTGAC

HisGlnTrpIleSerSerGluCysThrThrProCysSerGlySerTrpLeuArgAspIle
5881  CACCAGTGGATAAGCTCGGAGTGTACCACTCCATGCTCCGGTTCCTGGCTAAGGGACATC
      GTGGTCACCTATTCGAGCCTCACATGGTGAGGTACGAGGCCAAGGACCGATTCCCTGTAG
```

FIG. 1H

```
           TrpAspTrpIleCysGluValLeuSerAspPheLysThrTrpLeuLysAlaLysLeuMet
5941       TGGGACTGGATATGCGAGGTGTTGAGCGACTTTAAGACCTGGCTAAAAGCTAAGCTCATG
           ACCCTGACCTATACGCTCCACAACTCGCTGAAATTCTGGACCGATTTTCGATTCGAGTAC

ProGlnLeuProGlyIleProPheValSerCysGlnArgGlyTyrLysGlyValTrpArg
6001       CCACAGCTGCCTGGGATCCCCTTTGTGTCCTGCCAGCGCGGGTATAAGGGGGTCTGGCGA
           GGTGTCGACGGACCCTAGGGGAAACACAGGACGGTCGCGCCCATATTCCCCCAGACCGCT (Val)
           GlyAspGlyIleMetHisThrArgCysHisCysGlyAlaGluIleThrGlyHisValLys
6061       GTGGACGGCATCATGCACACTCGCTGCCACTGTGGAGCTGAGATCACTGGACATGTCAAA
           CACCTGCCGTAGTACGTGTGAGCGACGGTGACACCTCGACTCTAGTGACCTGTACAGTTT

AsnGlyThrMetArgIleValGlyProArgThrCysArgAsnMetTrpSerGlyThrPhe
6121       AACGGGACGATGAGGATCGTCGGTCCTAGGACCTGCAGGAACATGTGGAGTGGGACCTTC
           TTGCCCTGCTACTCCTAGCAGCCAGGATCCTGGACGTCCTTGTACACCTCACCCTGGAAG

ProIleAsnAlaTyrThrThrGlyProCysThrProLeuProAlaProAsnTyrThrPhe
6181       CCCATTAATGCCTACACCACGGGCCCCTGTACCCCCCTTCCTGCGCCGAACTACACGTTC
           GGGTAATTACGGATGTGGTGCCCGGGGACATGGGGGGAAGGACGCGGCTTGATGTGCAAG

AlaLeuTrpArgValSerAlaGluGluTyrValGluIleArgGlnValGlyAspPheHis
6241       GCGCTATGGAGGGTGTCTGCAGAGGAATATGTGGAGATAAGGCAGGTGGGGGACTTCCAC
           CGCGATACCTCCCACAGACGTCTCCTTATACACCTCTATTCCGTCCACCCCCTGAAGGTG

TyrValThrGlyMetThrThrAspAsnLeuLysCysProCysGlnValProSerProGlu
6301       TACGTGACGGGTATGACTACTGACAATCTCAAATGCCCGTGCCAGGTCCCATCGCCCGAA
           ATGCACTGCCCATACTGATGACTGTTAGAGTTTACGGGCACGGTCCAGGGTAGCGGGCTT

PhePheThrGluLeuAspGlyValArgLeuHisArgPheAlaProProCysLysProLeu
6361       TTTTTCACAGAATTGGACGGGGTGCGCCTACATAGGTTTGCGCCCCCTGCAAGCCCTTG
           AAAAAGTGTCTTAACCTGCCCCACGCGGATGTATCCAAACGCGGGGGGACGTTCGGGAAC

LeuArgGluGluValSerPheArgValGlyLeuHisGluTyrProValGlySerGlnLeu
6421       CTGCGGGAGGAGGTATCATTCAGAGTAGGACTCCACGAATACCCGGTAGGGTCGCAATTA
           GACGCCCTCCTCCATAGTAAGTCTCATCCTGAGGTGCTTATGGGCCATCCCAGCGTTAAT

ProCysGluProGluProAspValAlaValLeuThrSerMetLeuThrAspProSerHis
6481       CCTTGCGAGCCCGAACCGGACGTGGCCGTGTTGACGTCCATGCTCACTGATCCCTCCCAT
           GGAACGCTCGGGCTTGGCCTGCACCGGCACAACTGCAGGTACGAGTGACTAGGGAGGGTA

IleThrAlaGluAlaAlaGlyArgArgLeuAlaArgGlySerProProSerValAlaSer
6541       ATAACAGCAGAGGCGGCCGGGCGAAGGTTGGCGAGGGGATCACCCCCCTCTGTGGCCAGC
           TATTGTCGTCTCCGCCGGCCCGCTTCCAACCGCTCCCCTAGTGGGGGGAGACACCGGTCG

SerSerAlaSerGlnLeuSerAlaProSerLeuLysAlaThrCysThrAlaAsnHisAsp
6601       TCCTCGGCTAGCCAGCTATCCGCTCCATCTCTCAAGGCAACTTGCACCGCTAACCATGAC
           AGGAGCCGATCGGTCGATAGGCGAGGTAGAGAGTTCCGTTGAACGTGGCGATTGGTACTG

SerProAspAlaGluLeuIleGluAlaAsnLeuLeuTrpArgGlnGluMetGlyGlyAsn
6661       TCCCCTGATGCTGAGCTCATAGAGGCCAACCTCCTATGGAGGCAGGAGATGGGCGGCAAC
           AGGGGACTACGACTCGAGTATCTCCGGTTGGAGGATACCTCCGTCCTCTACCCGCCGTTG
```

FIG. II

```
          IleThrArgValGluSerGluAsnLysValValIleLeuAspSerPheAspProLeuVal
6721      ATCACCAGGGTTGAGTCAGAAAACAAAGTGGTGATTCTGGACTCCTTCGATCCGCTTGTG
          TAGTGGTCCCAACTCAGTCTTTTGTTTCACCACTAAGACCTGAGGAAGCTAGGCGAACAC

AlaGluGluAspGluArgGluIleSerValProAlaGluIleLeuArgLysSerArgArg
6781      GCGGAGGAGGACGAGCGGGAGATCTCCGTACCCGCAGAAATCCTGCGGAAGTCTCGGAGA
          CGCCTCCTCCTGCTCGCCCTCTAGAGGCATGGGCGTCTTTAGGACGCCTTCAGAGCCTCT

PheAlaGlnAlaLeuProValTrpAlaArgProAspTyrAsnProProLeuValGluThr
6841      TTCGCCCAGGCCCTGCCCGTTTGGGCGCGGCCGGACTATAACCCCCCGCTAGTGGAGACG
          AAGCGGGTCCGGGACGGGCAAACCCGCGCCGGCCTGATATTGGGGGGCGATCACCTCTGC

TrpLysLysProAspTyrGluProProValValHisGlyCysProLeuProProProLys
6901      TGGAAAAAGCCCGACTACGAACCACCTGTGGTCCATGGCTGTCCGCTTCCACCTCCAAAG
          ACCTTTTTCGGGCTGATGCTTGGTGGACACCAGGTACCGACAGGCGAAGGTGGAGGTTTC

SerProProValProProProArgLysLysArgThrValValLeuThrGluSerThrLeu
6961      TCCCCTCCTGTGCCTCCGCCTCGGAAGAAGCGGACGGTGGTCCTCACTGAATCAACCCTA
          AGGGGAGGACACGGAGGCGGAGCCTTCTTCGCCTGCCACCAGGAGTGACTTAGTTGGGAT (Ser)
          SerThrAlaLeuAlaGluLeuAlaThrArgSerPheGlySerSerSerThrSerGlyIle
7021      TCTACTGCCCTTGGCCGAGCTCGCCACCAGAAGCTTTGGCAGCTCCTCAACTTCCGGCATT
          AGATGACGGAACCGGCTCGAGCGGTGGTCTTCGAAACCGTCGAGGAGTTGAAGGCCGTAA

ThrGlyAspAsnThrThrThrSerSerGluProAlaProSerGlyCysProProAspSer
7081      ACGGGCGACAATACGACAACATCCTCTGAGCCCGCCCCTTCTGGCTGCCCCCCCGACTCC
          TGCCCGCTGTTATGCTGTTGTAGGAGACTCGGGCGGGGAAGACCGACGGGGGGGCTGAGG (PheAla)
          AspAlaGluSerTyrSerSerMetProProLeuGluGlyGluProGlyAspProAspLeu
7141      GACGCTGAGTCCTATTCCTCCATGCCCCCCCTGGAGGGGGAGCCTGGGGATCCGGATCTT
          CTGCGACTCAGGATAAGGAGGTACGGGGGGGACCTCCCCCTCGGACCCCTAGGCCTAGAA

SerAspGlySerTrpSerThrValSerSerGluAlaAsnAlaGluAspValValCysCys
7201      AGCGACGGGTCATGGTCAACGGTCAGTAGTGAGGCCAACGCGGAGGATGTCGTGTGCTGC
          TCGCTGCCCAGTACCAGTTGCCAGTCATCACTCCGGTTGCGCCTCCTACAGCACACGACG

SerMetSerTyrSerTrpThrGlyAlaLeuValThrProCysAlaAlaGluGluGlnLys
7261      TCAATGTCTTACTCTTGGACAGGCGCACTCGTCACCCCGTGCGCCGCGGAAGAACAGAAA
          AGTTACAGAATGAGAACCTGTCCGCGTGAGCAGTGGGGCACGCGGCGCCTTCTTGTCTTT

LeuProIleAsnAlaLeuSerAsnSerLeuLeuArgHisHisAsnLeuValTyrSerThr
7321      CTGCCCATCAATGCACTAAGCAACTCGTTGCTACGTCACCACAATTTGGTGTATTCCACC
          GACGGGTAGTTACGTGATTCGTTGAGCAACGATGCAGTGGTGTTAAACCACATAAGGTGG

ThrSerArgSerAlaCysGlnArgGlnLysLysValThrPheAspArgLeuGlnValLeu
7381      ACCTCACGCAGTGCTTGCCAAAGGCAGAAGAAAGTCACATTTGACAGACTGCAAGTTCTG
          TGGAGTGCGTCACGAACGGTTTCCGTCTTCTTTCAGTGTAAACTGTCTGACGTTCAAGAC

AspSerHisTyrGlnAspValLeuLysGluValLysAlaAlaAlaSerLysValLysAla
7441      GACAGCCATTACCAGGACGTACTCAAGGAGGTTAAAGCAGCGGCGTCAAAAGTGAAGGCT
          CTGTCGGTAATGGTCCTGCATGAGTTCCTCCAATTTCGTCGCCGCAGTTTTCACTTCCGA
```

FIG. IJ

```
                (Phe)
       AsnLeuLeuSerValGluGluAlaCysSerLeuThrProProHisSerAlaLysSerLys
7501   AACTTGCTATCCGTAGAGGAAGCTTGCAGCCTGACGCCCCCACACTCAGCCAAATCCAAG
       TTGAACGATAGGCATCTCCTTCGAACGTCGGACTGCGGGGGTGTGAGTCGGTTTAGGTTC

PheGlyTyrGlyAlaLysAspValArgCysHisAlaArgLysAlaValThrHisIleAsn
7561   TTTGGTTATGGGGCAAAAGACGTCCGTTGCCATGCCAGAAAGGCCGTAACCCACATCAAC
       AAACCAATACCCCGTTTTCTGCAGGCAACGGTACGGTCTTTCCGGCATTGGGTGTAGTTG

SerValTrpLysAspLeuLeuGluAspAsnValThrProIleAspThrThrIleMetAla
7621   TCCGTGTGGAAAGACCTTCTGGAAGACAATGTAACACCAATAGACACTACCATCATGGCT
       AGGCACACCTTTCTGGAAGACCTTCTGTTACATTGTGGTTATCTGTGATGGTAGTACCGA

LysAsnGluValPheCysValGlnProGluLysGlyGlyArgLysProAlaArgLeuIle
7681   AAGAACGAGGTTTTCTGCGTTCAGCCTGAGAAGGGGGGTCGTAAGCCAGCTCGTCTCATC
       TTCTTGCTCCAAAAGACGCAAGTCGGACTCTTCCCCCCAGCATTCGGTCGAGCAGAGTAG

ValPheProAspLeuGlyValArgValCysGluLysMetAlaLeuTyrAspValValThr
7741   GTGTTCCCCGATCTGGGCGTGCGCGTGTGCGAAAAGATGGCTTTGTACGACGTGGTTACA
       CACAAGGGGCTAGACCCGCACGCGCACACGCTTTTCTACCGAAACATGCTGCACCAATGT

LysLeuProLeuAlaValMetGlySerSerTyrGlyPheGlnTyrSerProGlyGlnArg
7801   AAGCTCCCCTTGGCCGTGATGGGAAGCTCCTACGGATTCCAATACTCACCAGGACAGCGG
       TTCGAGGGGAACCGGCACTACCCTTCGAGGATGCCTAAGGTTATGAGTGGTCCTGTCGCC

ValGluPheLeuValGlnAlaTrpLysSerLysLysThrProMetGlyPheSerTyrAsp
7861   GTTGAATTCCTCGTGCAAGCGTGGAAGTCCAAGAAAACCCCAATGGGGTTCTCGTATGAT
       CAACTTAAGGAGCACGTTCGCACCTTCAGGTTCTTTTGGGGTTACCCCAAGAGCATACTA

ThrArgCysPheAspSerThrValThrGluSerAspIleArgThrGluGluAlaIleTyr
7921   ACCCGCTGCTTTGACTCCACAGTCACTGAGAGCGACATCCGTACGGAGGAGGCAATCTAC
       TGGGCGACGAAACTGAGGTGTCAGTGACTCTCGCTGTAGGCATGCCTCCTCCGTTAGATG

GlnCysCysAspLeuAspProGlnAlaArgValAlaIleLysSerLeuThrGluArgLeu
7981   CAATGTTGTGACCTCGACCCCCAAGCCCGCGTGGCCATCAAGTCCCTCACCGAGAGGCTT
       GTTACAACACTGGAGCTGGGGGTTCGGGCGCACCGGTAGTTCAGGGAGTGGCTCTCCGAA (Gly)
       TyrValGlyGlyProLeuThrAsnSerArgGlyGluAsnCysGlyTyrArgArgCysArg
8041   TATGTTGGGGGCCCTCTTACCAATTCAAGGGGGGAGAACTGCGGCTATCGCAGGTGCCGC
       ATACAACCCCCGGGAGAATGGTTAAGTTCCCCCCTCTTGACGCCGATAGCGTCCACGGCG

AlaSerGlyValLeuThrThrSerCysGlyAsnThrLeuThrCysTyrIleLysAlaArg
8101   GCGAGCGGCGTACTGACAACTAGCTGTGGTAACACCCTCACTTGCTACATCAAGGCCCGG
       CGCTCGCCGCATGACTGTTGATCGACACCATTGTGGGAGTGAACGATGTAGTTCCGGGCC

AlaAlaCysArgAlaAlaGlyLeuGlnAspCysThrMetLeuValCysGlyAspAspLeu
8161   GCAGCCTGTCGAGCCGCAGGGCTCCAGGACTGCACCATGCTCGTGTGTGGCGACGACTTA
       CGTCGGACAGCTCGGCGTCCCGAGGTCCTGACGTGGTACGAGCACACACCGCTGCTGAAT

ValValIleCysGluSerAlaGlyValGlnGluAspAlaAlaSerLeuArgAlaPheThr
8221   GTCGTTATCTGTGAAAGCGCGGGGGTCCAGGAGGACGCGGCGAGCCTGAGAGCCTTCACG
       CAGCAATAGACACTTTCGCGCCCCCAGGTCCTCCTGCGCCGCTCGGACTCTCGGAAGTGC
```

FIG. IK

```
      GluAlaMetThrArgTyrSerAlaProProGlyAspProProGlnProGluTyrAspLeu
8281  GAGGCTATGACCAGGTACTCCGCCCCCCTGGGGACCCCCCACAACCAGAATACGACTTG
      CTCCGATACTGGTCCATGAGGCGGGGGGGACCCCTGGGGGGTGTTGGTCTTATGCTGAAC

GluLeuIleThrSerCysSerSerAsnValSerValAlaHisAspGlyAlaGlyLysArg
8341  GAGCTCATAACATCATGCTCCTCCAACGTGTCAGTCGCCCACGACGGCGCTGGAAAGAGG
      CTCGAGTATTGTAGTACGAGGAGGTTGCACAGTCAGCGGGTGCTGCCGCGACCTTTCTCC

ValTyrTyrLeuThrArgAspProThrThrProLeuAlaArgAlaAlaTrpGluThrAla
8401  GTCTACTACCTCACCCGTGACCCTACAACCCCCTCGCGAGAGCTGCGTGGGAGACAGCA
      CAGATGATGGAGTGGGCACTGGGATGTTGGGGGGAGCGCTCTCGACGCACCCTCTGTCGT

ArgHisThrProValAsnSerTrpLeuGlyAsnIleIleMetPheAlaProThrLeuTrp
8461  AGACACACTCCAGTCAATTCCTGGCTAGGCAACATAATCATGTTTGCCCCCACACTGTGG
      TCTGTGTGAGGTCAGTTAAGGACCGATCCGTTGTATTAGTACAAACGGGGGTGTGACACC

AlaArgMetIleLeuMetThrHisPhePheSerValLeuIleAlaArgAspGlnLeuGlu
8521  GCGAGGATGATACTGATGACCCATTTCTTTAGCGTCCTTATAGCCAGGGACCAGCTTGAA
      CGCTCCTACTATGACTACTGGGTAAAGAAATCGCAGGAATATCGGTCCCTGGTCGAACTT

GlnAlaLeuAspCysGluIleTyrGlyAlaCysTyrSerIleGluProLeuAspLeuPro
8581  CAGGCCCTCGATTGCGAGATCTACGGGGCCTGCTACTCCATAGAACCACTTGATCTACCT
      GTCCGGGAGCTAACGCTCTAGATGCCCCGGACGATGAGGTATCTTGGTGAACTAGATGGA

ProIleIleGlnArgLeuHisGlyLeuSerAlaPheSerLeuHisSerTyrSerProGly
8641  CCAATCATTCAAAGACTCCATGGCCTCAGCGCATTTTCACTCCACAGTTACTCTCCAGGT
      GGTTAGTAAGTTTCTGAGGTACCGGAGTCGCGTAAAAGTGAGGTGTCAATGAGAGGTCCA

GluIleAsnArgValAlaAlaCysLeuArgLysLeuGlyValProProLeuArgAlaTrp
8701  GAAATTAATAGGGTGGCCGCATGCCTCAGAAAACTTGGGGTACCGCCCTTGCGAGCTTGG
      CTTTAATTATCCCACCGGCGTACGGAGTCTTTTGAACCCCATGGCGGGAACGCTCGAACC

Gly
      ArgHisArgAlaArgSerValArgAlaArgLeuLeuAlaArgGlyGlyArgAlaAlaIle
8761  AGACACCGGGCCCGGAGCGTCCGCGCTAGGCTTCTGGCCAGAGGAGGCAGGGCTGCCATA
      TCTGTGGCCCGGGCCTCGCAGGCGCGATCCGAAGACCGGTCTCCTCCGTCCCGACGGTAT

CysGlyLysTyrLeuPheAsnTrpAlaValArgThrLysLeuLysLeuThrProIleAla
8821  TGTGGCAAGTACCTCTTCAACTGGGCAGTAAGAACAAAGCTCAAACTCACTCCAATAGCG
      ACACCGTTCATGGAGAAGTTGACCCGTCATTCTTGTTTCGAGTTTGAGTGAGGTTATCGC

AlaAlaGlyGlnLeuAspLeuSerGlyTrpPheThrAlaGlyTyrSerGlyGlyAspIle
8881  GCCGCTGGCCAGCTGGACTTGTCCGGCTGGTTCACGGCTGGCTACAGCGGGGGAGACATT
      CGGCGACCGGTCGACCTGAACAGGCCGACCAAGTGCCGACCGATGTCGCCCCCTCTGTAA (Pro)
      TyrHisSerValSerHisAlaArgProArgTrpIleTrpPheCysLeuLeuLeuLeuAla
8941  TATCACAGCGTGTCTCATGCCCGGCCCCGCTGGATCTGGTTTTGCCTACTCCTGCTTGCT
      ATAGTGTCGCACAGAGTACGGGCCGGGGCGACCTAGACCAAAACGGATGAGGACGAACGA

AlaGlyValGlyIleTyrLeuLeuProAsnArgOP
9001  GCAGGGGTAGGCATCTACCTCCTCCCCAACCGATGAAGGTTGGGGTAAACACTCCGGCCT
      CGTCCCCATCCGTAGATGGAGGAGGGGTTGGCTACTTCCAACCCCATTTGTGAGGCCGGA
```

FIG. IL

Coding:
- aa 1-154     hSOD
- aa 155-159     linker
- aa 160-899     c200 [aa HCV1 1192-1931]
- aa 900-902     linker
- aa 903-1021     c22 [aa HCV1 2-120]

Translation of SODc200core

```
  1                                         10
Met Ala Thr Lys Ala Val Cys Val Leu Lys Gly Asp Gly Pro Val
ATG GCT ACA AAG GCT GTT TGT GTT TTG AAG GGT GAC GGC CCA GTT 20                                      30
Gln Gly Ile Ile Asn Phe Glu Gln Lys Glu Ser Asn Gly Pro Val
CAA GGT ATT ATT AAC TTC GAG CAG AAG GAA AGT AAT GGA CCA GTG

40
Lys Val Trp Gly Ser Ile Lys Gly Leu Thr Glu Gly Leu His Gly
AAG GTG TGG GGA AGC ATT AAA GGA CTG ACT GAA GGC CTG CAT GGA 50                                      60
Phe His Val His Glu Phe Gly Asp Asn Thr Ala Gly Cys Thr Ser
TTC CAT GTT CAT GAG TTT GGA GAT AAT ACA GCA GGC TGT ACC AGT

70
Ala Gly Pro His Phe Asn Pro Leu Ser Arg Lys His Gly Gly Pro
GCA GGT CCT CAC TTT AAT CCT CTA TCC AGA AAA CAC GGT GGG CCA 80                                      90
Lys Asp Glu Glu Arg His Val Gly Asp Leu Gly Asn Val Thr Ala
AAG GAT GAA GAG AGG CAT GTT GGA GAC TTG GGC AAT GTG ACT GCT

100
Asp Lys Asp Gly Val Ala Asp Val Ser Ile Glu Asp Ser Val Ile
GAC AAA GAT GGT GTG GCC GAT GTG TCT ATT GAA GAT TCT GTG ATC 110                                     120
Ser Leu Ser Gly Asp His Cys Ile Ile Gly Arg Thr Leu Val Val
TCA CTC TCA GGA GAC CAT TGC ATC ATT GGC CGC ACA CTG GTG GTC

130
His Glu Lys Ala Asp Asp Leu Gly Lys Gly Gly Asn Glu Glu Ser
CAT GAA AAA GCA GAT GAC TTG GGC AAA GGT GGA AAT GAA GAA AGT 140                                     150
Thr Lys Thr Gly Asn Ala Gly Ser Arg Leu Ala Cys Gly Val Ile
ACA AAG ACA GGA AAC GCT GGA AGT CGT TTG GCT TGT GGT GTA ATT

*                        *160
Gly Ile Ala Gln*Asn Leu Glu Phe Gly*Ala Val Asp Phe Ile Pro
GGG ATC GCC CAG*AAT TTG GAA TTC GGG*GCG GTG GAC TTT ATC CCT
```

FIG. 4A

```
                              170                                              180
Val Glu Asn Leu Glu Thr Thr Met Arg Ser Pro Val Phe Thr Asp
GTG GAG AAC CTA GAG ACA ACC ATG AGG TCC CCG GTG TTC ACG GAT

190
Asn Ser Ser Pro Pro Val Val Pro Gln Ser Phe Gln Val Ala His
AAC TCC TCT CCA CCA GTA GTG CCC CAG AGC TTC CAG GTG GCT CAC 200                                          210
Leu His Ala Pro Thr Gly Ser Gly Lys Ser Thr Lys Val Pro Ala
CTC CAT GCT CCC ACA GGC AGC GGC AAA AGC ACC AAG GTC CCG GCT

220
Ala Tyr Ala Ala Gln Gly Tyr Lys Val Leu Val Leu Asn Pro Ser
GCA TAT GCA GCT CAG GGC TAT AAG GTG CTA GTA CTC AAC CCC TCT 230                                              240
Val Ala Ala Thr Leu Gly Phe Gly Ala Tyr Met Ser Lys Ala His
GTT GCT GCA ACA CTG GGC TTT GGT GCT TAC ATG TCC AAG GCT CAT

250
Gly Ile Asp Pro Asn Ile Arg Thr Gly Val Arg Thr Ile Thr Thr
GGG ATC GAT CCT AAC ATC AGG ACC GGG GTG AGA ACA ATT ACC ACT 260                                                 270
Gly Ser Pro Ile Thr Tyr Ser Thr Tyr Gly Lys Phe Leu Ala Asp
GGC AGC CCC ATC ACG TAC TCC ACC TAC GGC AAG TTC CTT GCC GAC

280
Gly Gly Cys Ser Gly Gly Ala Tyr Asp Ile Ile Ile Cys Asp Glu
GGC GGG TGC TCG GGG GGC GCT TAT GAC ATA ATA ATT TGT GAC GAG 290                                                 300
Cys His Ser Thr Asp Ala Thr Ser Ile Leu Gly Ile Gly Thr Val
TGC CAC TCC ACG GAT GCC ACA TCC ATC TTG GGC ATC GGC ACT GTC

310
Leu Asp Gln Ala Glu Thr Ala Gly Ala Arg Leu Val Val Leu Ala
CTT GAC CAA GCA GAG ACT GCG GGG GCG AGA CTG GTT GTG CTC GCC 320                                                 330
Thr Ala Thr Pro Pro Gly Ser Val Thr Val Pro His Pro Asn Ile
ACC GCC ACC CCT CCG GGC TCC GTC ACT GTG CCC CAT CCC AAC ATC

340
Glu Glu Val Ala Leu Ser Thr Thr Gly Glu Ile Pro Phe Tyr Gly
GAG GAG GTT GCT CTG TCC ACC ACC GGA GAG ATC CCT TTT TAC GGC 350                                                 360
Lys Ala Ile Pro Leu Glu Val Ile Lys Gly Gly Arg His Leu Ile
AAG GCT ATC CCC CTC GAA GTA ATC AAG GGG GGG AGA CAT CTC ATC

370
Phe Cys His Ser Lys Lys Lys Cys Asp Glu Leu Ala Ala Lys Leu
TTC TGT CAT TCA AAG AAG AAG TGC GAC GAA CTC GCC GCA AAG CTG
```

FIG. 4B

```
                    380                                                390
Val Ala Leu Gly Ile Asn Ala Val Ala Tyr Tyr Arg Gly Leu Asp
GTC GCA TTG GGC ATC AAT GCC GTG GCC TAC TAC CGC GGT CTT GAC

400
Val Ser Val Ile Pro Thr Ser Gly Asp Val Val Val Val Ala Thr
GTG TCC GTC ATC CCG ACC AGC GGC GAT GTT GTC GTC GTG GCA ACC 410                                                420
Asp Ala Leu Met Thr Gly Tyr Thr Gly Asp Phe Asp Ser Val Ile
GAT GCC CTC ATG ACC GGC TAT ACC GGC GAC TTC GAC TCG GTG ATA

430
Asp Cys Asn Thr Cys Val Thr Gln Thr Val Asp Phe Ser Leu Asp
GAC TGC AAT ACG TGT GTC ACC CAG ACA GTC GAT TTC AGC CTT GAC 440                                                450
Pro Thr Phe Thr Ile Glu Thr Ile Thr Leu Pro Gln Asp Ala Val
CCT ACC TTC ACC ATT GAG ACA ATC ACG CTC CCC CAG GAT GCT GTC

460
Ser Arg Thr Gln Arg Arg Gly Arg Thr Gly Arg Gly Lys Pro Gly
TCC CGC ACT CAA CGT CGG GGC AGG ACT GGC AGG GGG AAG CCA GGC 470                                                480
Ile Tyr Arg Phe Val Ala Pro Gly Glu Arg Pro Ser Gly Met Phe
ATC TAC AGA TTT GTG GCA CCG GGG GAG CGC CCC TCC GGC ATG TTC

490
Asp Ser Ser Val Leu Cys Glu Cys Tyr Asp Ala Gly Cys Ala Trp
GAC TCG TCC GTC CTC TGT GAG TGC TAT GAC GCA GGC TGT GCT TGG 500                                                510
Tyr Glu Leu Thr Pro Ala Glu Thr Thr Val Arg Leu Arg Ala Tyr
TAT GAG CTC ACG CCC GCC GAG ACT ACA GTT AGG CTA CGA GCG TAC

520
Met Asn Thr Pro Gly Leu Pro Val Cys Gln Asp His Leu Glu Phe
ATG AAC ACC CCG GGG CTT CCC GTG TGC CAG GAC CAT CTT GAA TTT 530                                                540
Trp Glu Gly Val Phe Thr Gly Leu Thr His Ile Asp Ala His Phe
TGG GAG GGC GTC TTT ACA GGC CTC ACT CAT ATA GAT GCC CAC TTT

550
Leu Ser Gln Thr Lys Gln Ser Gly Glu Asn Leu Pro Tyr Leu Val
CTA TCC CAG ACA AAG CAG AGT GGG GAG AAC CTT CCT TAC CTG GTA 560                                                570
Ala Tyr Gln Ala Thr Val Cys Ala Arg Ala Gln Ala Pro Pro Pro
GCG TAC CAA GCC ACC GTG TGC GCT AGG GCT CAA GCC CCT CCC CCA

580
Ser Trp Asp Gln Met Trp Lys Cys Leu Ile Arg Leu Lys Pro Thr
TCG TGG GAC CAG ATG TGG AAG TGT TTG ATT CGC CTC AAG CCC ACC
```

FIG. 4C

```
                  590                                                    600
Leu His Gly Pro Thr Pro Leu Leu Tyr Arg Leu Gly Ala Val Gln
CTC CAT GGG CCA ACA CCC CTG CTA TAC AGA CTG GGC GCT GTT CAG

610
Asn Glu Ile Thr Leu Thr His Pro Val Thr Lys Tyr Ile Met Thr
AAT GAA ATC ACC CTG ACG CAC CCA GTC ACC AAA TAC ATC ATG ACA 620                                                    630
Cys Met Ser Ala Asp Leu Glu Val Val Thr Ser Thr Trp Val Leu
TGC ATG TCG GCC GAC CTG GAG GTC GTC ACG AGC ACC TGG GTG CTC

640
Val Gly Gly Val Leu Ala Ala Leu Ala Ala Tyr Cys Leu Ser Thr
GTT GGC GGC GTC CTG GCT GCT TTG GCC GCG TAT TGC CTG TCA ACA 650                                                    660
Gly Cys Val Val Ile Val Gly Arg Val Val Leu Ser Gly Lys Pro
GGC TGC GTG GTC ATA GTG GGC AGG GTC GTC TTG TCC GGG AAG CCG

670
Ala Ile Ile Pro Asp Arg Glu Val Leu Tyr Arg Glu Phe Asp Glu
GCA ATC ATA CCT GAC AGG GAA GTC CTC TAC CGA GAG TTC GAT GAG 680                                                690
Met Glu Glu Cys Ser Gln His Leu Pro Tyr Ile Glu Gln Gly Met
ATG GAA GAG TGC TCT CAG CAC TTA CCG TAC ATC GAG CAA GGG ATG

700
Met Leu Ala Glu Gln Phe Lys Gln Lys Ala Leu Gly Leu Leu Gln
ATG CTC GCC GAG CAG TTC AAG CAG AAG GCC CTC GGC CTC CTG CAG 710                                                720
Thr Ala Ser Arg Gln Ala Glu Val Ile Ala Pro Ala Val Gln Thr
ACC GCG TCC CGT CAG GCA GAG GTT ATC GCC CCT GCT GTC CAG ACC

730
Asn Trp Gln Lys Leu Glu Thr Phe Trp Ala Lys His Met Trp Asn
AAC TGG CAA AAA CTC GAG ACC TTC TGG GCG AAG CAT ATG TGG AAC 740                                                750
Phe Ile Ser Gly Ile Gln Tyr Leu Ala Gly Leu SEr Thr Leu Pro
TTC ATC AGT GGG ATA CAA TAC TTG GCG GGC TTG TCA ACG CTG CCT

760
Gly Asn Pro Ala Ile Ala Ser Leu Met Ala Phe Thr Ala Ala Val
GGT AAC CCC GCC ATT GCT TCA TTG ATG GCT TTT ACA GCT GCT GTC 770                                                    780
Thr Ser Pro Leu Thr Thr Ser Gln Thr Leu Leu Phe Asn Ile Leu
ACC AGC CCA CTA ACC ACT AGC CAA ACC CTC CTC TTC AAC ATA TTG

790
Gly Gly Trp Val Ala Ala Gln Leu Ala Ala Pro Gly Ala Ala Thr
GGG GGG TGG GTG GCT GCC CAG CTC GCC GCC CCC GGT GCC GCT ACT
```

FIG. 4D

```
                    800                                              810
Ala Phe Val Gly Ala Gly Leu Ala Gly Ala Ala Ile Gly Ser Val
GCC TTT GTG GGC GCT GGC TTA GCT GGC GCC GCC ATC GGC AGT GTT

820
Gly Leu Gly Lys Val Leu Ile Asp Ile Leu Ala Gly Tyr Gly Ala
GGA CTG GGG AAG GTC CTC ATA GAC ATC CTT GCA GGG TAT GGC GCG 830                                              840
Gly Val Ala Gly Ala Leu Val Ala Phe Lys Ile Met Ser Gly Glu
GGC GTG GCG GGA GCT CTT GTG GCA TTC AAG ATC ATG AGC GGT GAG

850
Val Pro Ser Thr Glu Asp Leu Val Asn Leu Leu Pro Ala Ile Leu
GTC CCC TCC ACG GAG GAC CTG GTC AAT CTA CTG CCC GCC ATC CTC 860                                              870
Ser Pro Gly Ala Leu Val Val Gly Val Val Cys Ala Ala Ile Leu
TCG CCC GGA GCC CTC GTA GTC GGC GTG GTC TGT GCA GCA ATA CTG

880
Arg Arg His Val Gly Pro Gly Glu Gly Ala Val Gln Trp Met Asn
CGC CGG CAC GTT GGC CCA GGC GAG GGG GCA GTG CAG TGG ATG AAC

890                                     *900
Arg Leu Ile Ala Phe Ala Ser Arg Gly Asn His Val Ser Pro*Gly
CGG CTG ATA GCC TTC GCC TCA CGG GGG AAC CAT GTT TCA CCC*GGG

*                            910
Asn Ser*Ser Thr ASn Pro Lys Pro Gln Lys Lys Asn Lys Arg Asn
AAT TCC*AGC ACG AAT CCT AAA CCT CAA AAA AAA AAC AAA CGT AAC 920                                              930
Thr Asn Arg Arg Pro Gln Asp Val Lys Phe Pro Gly Gly Gly Gln
ACC AAC CGT CGC CCA CAG GAC GTC AAG TTC CCG GGT GGC GGT CAG

940
Ile Val Gly Gly Val Tyr Leu Leu Pro Arg Arg Gly Pro Arg Leu
ATC GTT GGT GGA GTT TAC TTG TTG CCG CGC AGG GGC CCT AGA TTG 950                                              960
Gly Val Arg Ala Thr Arg Lys Thr Ser Glu Arg Ser Gln Pro Arg
GGT GTG CGC GCG ACG AGA AAG ACT TCC GAG CGG TCG CAA CCT CGA

970
Gly Arg Arg Gln Pro Ile Pro Lys Ala Arg Arg Pro Glu Gly Arg
GGT AGA CGT CAG CCT ATC CCC AAG GCT CGT CGG CCC GAG GGC AGG 980                                  990
Thr Trp Ala Gln Pro Gly Tyr Pro Trp Pro Leu Tyr Gly Asn Glu
ACC TGG GCT CAG CCC GGG TAC CCT TGG CCC CTC TAT GGC AAT GAG

1000
Gly Cys Gly Trp Ala Gly Trp Leu Leu Ser Pro Arg Gly Ser Arg
GGC TGC GGG TGG GCG GGA TGG CTC CTG TCT CCC CGT GGC TCT CGG 1010                                         1020
Pro Ser Trp Gly Pro Thr Asp Pro Arg Arg Arg Ser Arg Asn Leu
CCT AGC TGG GGC CCC ACA GAC CCC CGG CGT AGG TCG CGC AAT TTG

1021
Gly OC
GGT TAA TGAGTCGAC
```

FIG. 4E

COMBINATIONS OF HEPATITIS C VIRUS (HCV) ANTIGENS FOR USE IN IMMUNOASSAYS FOR ANTI-HCV ANTIBODIES

REFERENCE TO RELATED APPLICATIONS

This application is a continuation of application Ser. No. 07/910,760, diled Jul. 7, 1992, which is a continuation-in-part of U.S. Ser. No. 07/504,352 (filed Apr. 4, 1990) abandoned, which in its entirety is hereby incorporated herein by reference.

DESCRIPTION

1. Technical Field

The present invention is in the field of immunoassays for HCV (previously called Non-A, Non-B hepatitis virus). More particularly, it concerns combinations of HCV antigens that permit broad range immunoassays for anti-HCV antibodies.

2. Background

The disease known previously as Non-A, Non-B hepatitis (NANBH) was considered to be a transmissible disease or family of diseases that were believed to be viral-induced, and that were distinguishable from other forms of viral-associated liver diseases, including that caused by the known hepatitis viruses, i.e., hepatitis A virus (HAV), hepatitis B virus (HBV), and delta hepatitis virus (HDV), as well as the hepatitis induced by cytomegalovirus (CMV) or Epstein-Barr virus (EBV). NANBH was first identified in transfused individuals. Transmission from man to chimpanzee and serial passage in chimpanzees provided evidence that NANBH was due to a transmissible infectious agent or agents. Epidemiologic evidence suggested that there may be three types of NANBH: a water-borne epidemic type; a blood-borne or parenterally transmitted type; and a sporadically occurring (community acquired) type. However, until recently; no transmissible agent responsible for NANBH had been identified, and clinical diagnosis and identification of NANBH had been accomplished primarily by exclusion of other viral markers. Among the methods used to detect putative NANBH antigens and antibodies were agar-gel diffusion, counterimmunoelectrophoresis, immunofluorescence microscopy, immune electron microscopy, radioimmunoassay, and enzyme-linked immunosorbent assay. However, none of these assays proved to be sufficiently sensitive, specific, and reproducible to be used as a diagnostic test for NANBH.

In 1987, scientists at Chiron Corporation (the owner of the present application) identified the first nucleic acid definitively linked to blood-borne NANBH. See, e.g., EPO Pub. No. 318,216; Houghton et al., Science 244:359 (1989). These publications describe the cloning of an isolate from a new viral class, hepatitis C virus (HCV), the prototype isolate described therein being named "HCV1." HCV is a Flavi-like virus, with an RNA genome.

U.S. patent application Ser. No. 456,637 (Houghton et al.), incorporated herein by reference, describes the preparation of various recombinant HCV polypeptides by expressing HCV cDNA and the screening of those polypeptides for immunological reactivity with sera from HCV patients. That limited screening showed that at least five of the polypeptides tested were very immunogenic; specifically, those identified as 5-1-1, C100, C33c, CA279a, and CA290a. Of these five polypeptides, 5-1-1 is located in the putative NS4 domain; C100 spans the putative NS3 and NS4 domains; C33c is located within the putative NS3 domain and CA279a and CA290a are located within the putative C domain. The screening also showed that no single polypeptide tested was immunologically reactive with all sera. Thus, improved tests, which react with all or more samples from HCV positive individuals, are desirable.

DISCLOSURE OF THE INVENTION

Applicants have carried out additional serological studies on HCV antigens that confirm that no single HCV polypeptide identified to date is immunologically reactive with all sera. This lack of a single polypeptide that is universally reactive with all sera from individuals with HCV may be due, inter alia, to strain-to-strain variation in HCV epitopes, variability in the humoral response from individual-to-individual and/or variation in serology with the state of the disease.

These additional studies have also enabled applicants to identify combinations of HCV antigens that provide more efficient detection of HCV antibodies than any single HCV polypeptide.

Accordingly, one aspect of this invention is a combination of antigens comprising:

(a) a first HCV antigen from the C domain; and
(b) at least one additional HCV antigen selected from the group consisting of
  (i) an HCV antigen from the NS3 domain;
  (ii) an HCV antigen from the NS4 domain;
  (iii) an HCV antigen from the S domain; and
  (iv) an HCV antigen from the NS5 domain.

In one embodiment, the combination of HCV antigens is in the form of a fusion protein comprised of the antigens. In an alternative embodiment, the combination of antigens is in the form of the individual antigens bound to a common solid matrix. In still another embodiment, the combination of antigens is in the form of a mixture of the individual antigens.

Another aspect of the invention is a method for detecting antibodies to HCV in a mammalian body component suspected of containing said antibodies comprising contacting said body component with the above-described combination of HCV antigens under conditions that permit antibody-antigen reaction and detecting the presence of immune complexes of said antibodies and said antigens.

Another aspect of the invention is a method for detecting antibodies to HCV in a mammalian body component suspected of containing said antibodies comprising contacting said body component with a panel of HCV antigens, simultaneously or sequentially, comprising:

(a) a first HCV antigen from the C domain; and
(b) at least one additional HCV antigen selected from the group consisting of
  (i) an HCV antigen from the NS3 domain;
  (ii) an HCV antigen from the NS4 domain;
  (iii) an HCV antigen from the S domain; and
  (iv) an HCV antigen from the NS5 domain under conditions that permit antibody-antigen reaction and detecting the presence of immune complexes of said antibodies and said antigens.

Another aspect of the invention is a kit for carrying out an assay for detecting antibodies to HCV in a mammalian body component suspected of containing said antibodies comprising in packaged combination (a) said combination of HCV antigens;

(b) standard control reagents; and (c) instructions for carrying out the assay.

BRIEF DESCRIPTION OF THE DRAWINGS

In the drawings:

FIG. 1 is the nucleotide sequence of the cDNA sense and anti-sense strand for the HCV (SEQ ID NO: 9) polyprotein and the amino acid sequence encoded by the sense strand (SEQ ID NO: 10).

FIG. 4 shows the coding sequence of pSOD/c200/core (SEQ ID NO: 11 and SEQ ID NO: 12).

MODES FOR CARRYING OUT THE INVENTION

Definitions

"HCV antigen" intends a polypeptide of at least about 5 amino acids, more usually at least about 8 to 10 amino acids that defines an epitope found in an isolate of HCV. Preferably, the epitope is unique to HCV. When an antigen is designated by an alphanumeric code, the epitope is from the HCV domain specified by the alphanumeric.

"Synthetic" as used to characterize an HCV antigen intends that the HCV antigen has either been isolated from native sources or man-made such as by chemical or recombinant synthesis.

Figure 2:
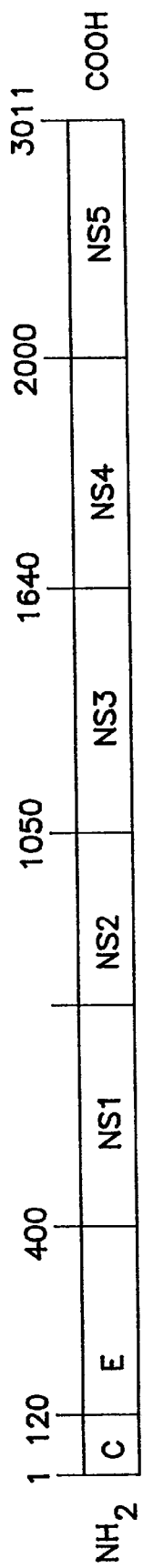
FIG. 2 is a schematic of the amino acid sequence of FIG. 1 showing the putative domains of the HCV polypeptide.

"Domains" intends those segments of the HCV polyprotein shown in FIG. 2 which generally correspond to the putative structural and nonstructural proteins of HCV. Domain designations generally follow the convention used to name Flaviviral proteins. The locations of the domains shown in FIG. 2 are only approximate. The designations "NS" denotes "nonstructural" domains, while "S" denotes the envelope domain, and "C" denotes the nucleocapsid or core domain.

"Fusion polypeptide" intends a polypeptide in which the HCV antigen(s) are part of a single continuous chain of amino acids, which chain does not occur in nature. The HCV antigens may be connected directly to each other by peptide bonds or be separated by intervening amino acid sequences. The fusion polypeptides may also contain amino acid sequences exogenous to HCV.

"Common solid matrix" intends a solid body to which the individual HCV antigens or the fusion polypeptide comprised of HCV antigens are bound covalently or by noncovalent means such as hydrophobic adsorption.

"Mammalian body component" intends a fluid or tissue of a mammalian individual (e.g., a human) that commonly contains antibodies produced by the individual. Such components are known in the art and include, without limitation, blood, plasma, serum, spinal fluid, lymph fluid, secretions of the respiratory, intestinal or genitourinary tracts, tears, saliva, milk, white blood cells, and myelomas.

"Immunologically reactive" means that the antigen in question will react specifically with anti-HCV antibody commonly present in a significant proportion of sera from individuals infected with HCV.

"Immune complex" intends the combination or aggregate formed when an antibody binds to an epitope on an antigen.
Combinations of HCV Antigens FIG. 2 shows the putative domains of the HCV polyprotein. The domains from which the antigens used in the combinations derive are: C, S (or E), NS3, NS4, and NS5. The C domain is believed to define the nucleocapsid protein of HCV. It extends from the N-terminal of the polyprotein to approximately amino acid 120 of FIG. 1. The S domain is believed to define the virion envelope protein, and possibly the matrix (M) protein, and is believed to extend from approximately amino acid 120 to amino acid 400 of FIG. 1. The NS3 domain extends from approximately amino acid 1050 to amino acid 1640 and is believed to constitute the viral protease. The NS4 domain extends from the terminus of NS3 to approximately amino acid 2000. The function of the NS4 protein is not known at this time. Finally, the NS5 domain extends from about amino acid 2000 to the end of the polyprotein and is believed to define the viral polymerase.

The sequence shown in FIG. 1 is the sequence of the HCV1 isolate. It is expected that the sequences of other strains of the blood-borne HCV may differ from the sequence of FIG. 1, particularly in the envelope (S) and nucleocapsid (C) domains. The use of HCV antigens having such differing sequences is intended to be within the scope of the present invention, provided, however, that the variation does not significantly degrade the immunological reactivity of the antigen to sera from persons infected with HCV.

In general, the HCV antigens will comprise entire or truncated domains, the domain fragments being readily screened for antigenicity by those skilled in the art. The individual HCV antigens used in the combination will preferably comprise the immunodominant portion (i.e., the portion primarily responsible for the immunological reactivity of the polypeptide) of the stated domain. In the case of the C domain it is preferred that the C domain antigen comprise a majority of the entire sequence of the domain. The antigen designated C22 (see Example 4, infra), is particularly preferred. The S domain antigen preferably includes the hydrophobic subdomain at the N-terminal end of the domain. This hydrophobic subdomain extends from approximately amino acid 199 to amino acid 328 of FIG. 1. The HCV antigen designated S2 (see Example 3, infra), is particularly preferred. Sequence downstream of the hydrophobic subdomain may be included in the S domain antigen if desired.

A preferred NS3 domain antigen is the antigen designated C33c. That antigen includes amino acids 1192 to 1457 of FIG. 1. A preferred NS4 antigen is C100 which comprises amino acids 1569 to 1931 of FIG. 1. A preferred NS5 antigen comprises amino acids 2054 to 2464 of FIG. 1. Additional preferred S domain antigens are disclosed in commonly owned U.S. Ser. No. 07/910,759 filed on even date herewith, entitled "Immunoassays for Anti-HCV Antibodies Using Antigens with Conformational Epitopes," by David Chien, and in U.S. Ser. No. 07/758,880, filed Sept. 13, 1991, and in WO92/08734, which are incorporated herein by reference.

The HCV antigen may be in the form of a polypeptide composed entirely of HCV amino acid sequence or it may contain sequence exogenous to HCV (i.e., it may be in the form of a fusion protein that includes exogenous sequence). In the case of recombinantly produced HCV antigen, producing the antigen as a fusion protein such as with SOD, alpha-factor or ubiquitin (see commonly owned U.S. Pat. No. 4,751,180, U.S. Pat. No. 4,870,008 and U.S. patent application Ser. No. 390,599, filed Aug. 7, 1989, the disclosures of which are incorporated herein, which describe expression of SOD, alpha-factor and ubiquitin fusion proteins) may increase the level of expression and/or increase the water solubility of the antigen. Fusion proteins such as the alpha-factor and ubiquitin fusion are processed by the expression host to remove the heterologous sequence. Alpha-factor is a secretion system, however, while ubiquitin fusions remain in the cytoplasm.

Further, the combination of antigens may be produced as a fusion protein. Generally, these fusions will combine epitopes from the C domain with one or more epitopes from the S, NS3, NS4 and/or NS5 domains (e.g., C/NS3/NS4 or C/NS5 or C.NS3.NS5). Another preferred class of fusions are those where the C domain epitopes are encoded at the carboxy end of the fusion protein (e.g., N'-NS3/NS4/C–C'; N'-NS3/C–C'; N'-NS5/C–C'; N'-NS3/NS4/NS5/C–C'; N'S/C–C'). For instance, a continuous fragment of DNA encoding C22 and C33c may be constructed, cloned into an expression vector and used to express a fusion protein of C22 and C33c. In a similar manner fusion proteins of C22 and C100; C22 and S2; C22 and an NS5 antigen; C22, C33c, and S2; C22, C100 and S2, and C22, C33c, C100, and S2 may be made. Examples of preferred fusion proteins are fusions with c200, such as c22/c200 and c200/c22. Alternative fragments from the exemplified domain may also be used.

Preparation of HCV Antigens

The HCV antigens of the invention are preferably produced recombinantly or by known solid phase chemical synthesis. They may, however, also be isolated from dissociated HCV or HCV particles using affinity chromatography techniques employing antibodies to the antigens.

When produced by recombinant techniques, standard procedures for constructing DNA encoding the antigen, cloning that DNA into expression vectors, transforming host cells such as bacteria, yeast, insect, or mammalian cells, and expressing such DNA to produce the antigen may be employed. As indicated previously, it may be desirable to express the antigen as a fusion protein to enhance expression, facilitate purification, or enhance solubility. Examples of specific procedures for producing representative HCV antigens are described in the Examples, infra, and in parent application Ser. No. 456,637, and in EPO Publication No. 318,216.

Formulation of Antigens for Use in Immunoassay

The HCV antigens may be combined by producing them in the form of a fusion protein composed of two or more of the antigens, by immobilizing them individually on a common solid matrix, or by physically mixing them. Fusion proteins of the antigen may also be immobilized on (bound to) a solid matrix. Methods and means for covalently or noncovalently binding proteins to solid matrices are known in the art. The nature of the solid surface will vary depending upon the assay format. For assays carried out in microtiter wells, the solid surface will be the wall of the well or cup. For assays using beads, the solid surface will be the surface of the bead. In assays using a dipstick (i.e., a solid body made from a porous or fibrous material such as fabric or paper) the surface will be the surface of the material from which the dipstick is made. In agglutination assays the solid surface may be the surface of latex or gelatin particles. When individual antigens are bound to the matrix they may be distributed homogeneously on the surface or distributed thereon in a pattern, such as bands so that a pattern of antigen binding may be discerned.

Simple mixtures of the antigens comprise the antigens in any suitable solvent or dispersing medium.

Assay Formats Using Combinations of Antigens

The HCV antigens may be employed in virtually any assay format that employs a known antigen to detect antibodies. A common feature of all of these assays is that the antigen is contacted with the body component suspected of containing HCV antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin, and enzyme-labeled and mediated immunoassays, such as ELISA assays.

The immunoassay may be, without limitation, in a heterogenous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immulon™), diazotized paper, nylon membranes, activated beads, and Protein A beads. For example, Dynatech Immulon™ 1 or Immulon™ 2 microtiter plates or 0.25 inch polysterene beads (Precision Plastic Ball) can be used in the heterogeneous format. The solid support containing the antigenic polypeptides is typically washed after separating it from the test sample, and prior to detection of bound antibodies. Both standard and competitive formats are known in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of HCV antibodies forming the antibody-antigen complex is directly monitored. This may be accomplished by determining whether labeled anti-xenogenic (e.g., anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

Complexes formed comprising anti-HCV antibody (or, in the case of competitive assays, the amount of competing antibody) are detected by any of a number of known techniques, depending on the format. For example, unlabeled HCV antibodies in the complex may be detected using a conjugate of antixenogeneic Ig complexed with a label, (e.g., an enzyme label).

In an immunoprecipitation or agglutination assay format the reaction between the HCV antigens and the antibody forms a network that precipitates from the solution or suspension and forms a visible layer or film of precipitate. If no anti-HCV antibody is present in the test specimen, no visible precipitate is formed.

The HCV antigens will typically be packaged in the form of a kit for use in these immunoassays. The kit will normally contain in separate containers the combination of antigens (either already bound to a solid matrix or separate with reagents for binding them to the matrix), control antibody formulations (positive and/or negative), labeled antibody when the assay format requires same and signal generating reagents (e.g., enzyme substrate) if the label does not generate a signal directly. Instructions (e.g., written, tape, VCR, CD-ROM, etc.) for carrying out the assay usually will be included in the kit.

The following examples are intended to illustrate the invention and are not intended to limit the invention in any manner.

EXAMPLE 1

Synthesis of HCV Antigen C33c

HCV antigen C33c contains a sequence from the NS3 domain. Specifically, it includes amino acids 1192–1457 of FIG. 1. This antigen was produced in bacteria as a fusion protein with human superoxide dismutase (SOD) as follows. The vector pSODcf1 (Steiner et al. (1986), J. Virol. 58:9) was digested to completion with EcoRI and BamHI and the resulting EcoRI,BamHI fragment was ligated to the following linker to form pcf1EF:

GATC CTG GAA TTC TGA TAA (SEQ ID NO: 1)

GAC CTT AAG ACT ATT TTA A (SEQ ID NO: 2)

A cDNA clone encoding amino acids 1192–1457 and having EcoRI ends was inserted into pcf1EF to form pcf1EF/C33c. This expression construct was transformed into D1210 *E. coli* cells.

The transformants were used to express a fusion protein comprised of SOD at the N-terminus and in-frame C33c HCV antigen at the C-terminus. Expression was accomplished by inoculating 1500 ml of Luria broth containing ampicillin (100 micrograms/ml) with 15 ml of an overnight culture of the transformants. The cells were grown to an O.D. of 0.3, IPTG was added to yield a final concentration of 2 mM, and growth continued until the cells attained a density of 1 O.D., at which time they were harvested by centrifugation at 3,000×g at 4° C. for 20 minutes. The packed cells can be stored at −80° C. for several months.

In order to purify the SOD-C33c polypeptide the bacterial cells in which the polypeptide was expressed were subjected to osmotic shock and mechanical disruption, the insoluble fraction containing SOD-C33c was isolated and subjected to differential extraction with an alkaline-NaCl solution, and the fusion polypeptide in the extract purified by chromatography on columns of S-Sepharose and Q-Sepharose.

The crude extract resulting from osmotic shock and mechanical disruption was prepared by the following procedure. One gram of the packed cells were suspended in 10 ml of a solution containing 0.02 M Tris HCl, pH 7.5, 10 mM EDTA, 20% sucrose, and incubated for 10 minutes on ice. The cells were then pelleted by centrifugation at 4,000×g for 15 min at 4° C. After the supernatant was removed, the cell pellets were resuspended in 10 ml of Buffer Al (0.01M Tris HCl, pH 7.5, 1 mM EDTA, 14 mM beta-mercaptoethanol [BME]), and incubated on ice for 10 minutes. The cells were again pelleted at 4,000×g for 15 minutes at 4° C. After removal of the clear supernatant (periplasmic fraction I), the cell pellets were resuspended in Buffer A1, incubated on ice for 10 minutes, and again centrifuged at 4,000×g for 15 minutes at 4° C. The clear supernatant (periplasmic fraction II) was removed, and the cell pellet resuspended in 5 ml of Buffer A2 (0.02 M Tris HCl, pH 7.5, 14 mM BME, 1 mM EDTA, 1 mM PMSF). In order to disrupt the cells, the suspension (5 ml) and 7.5 ml of Dyno-mill lead-free acid washed glass beads (0.10–0.15 mm diameter)(obtained from Glen-Mills, Inc.) were placed in a Falcon tube, and vortexed at top speed for two minutes, followed by cooling for at least 2 min on ice; the vortexing-cooling procedure was repeated another four times. After vortexing, the slurry was filtered through a scintered glass funnel using low suction; the glass beads were washed two times with Buffer A2, and the filtrate and washes combined.

The insoluble fraction of the crude extract was collected by centrifugation at 20,000×g for 15 min at 4° C., washed twice with 10 ml Buffer A2, and resuspended in 5 ml of MILLI-Q water.

A fraction containing SOD-C33c was isolated from the insoluble material by adding to the suspension NaOH (2 M) and NaCl (2 M) to yield a final concentration of 20 mM each, vortexing the mixture for 1 minute, centrifuging it 20,000×g for 20 min at 4° C., and retaining the supernatant.

In order to purify SOD-C33c on S-Sepharose, the supernatant fraction was adjusted to a final concentration of 6M urea, 0.05M Tris HCl, pH 7.5, 14 mM BME, 1 mM EDTA. This fraction was then applied to a column of S-Sepharose Fast Flow (1.5×10 cm) which had been equilibrated with Buffer B (0.05M Tris HCl, pH 7.5, 14 mM BME, 1 mM EDTA). After application, the column was washed with two column volumes of Buffer B. The flow through and wash fractions were collected. The flow rate of application and wash, was 1 ml/min; and collected fractions were 1 ml. In order to identify fractions containing SOD-C33c, aliquots of the fractions were analyzed by electrophoresis on 10% polyacrylamide gels containing SDS followed by staining with Coomassie blue. The fractions are also analyzable by Western blots using an antibody directed against SOD. Fractions containing SOD-C33c were pooled.

Further purification of SOD-C33c was on a Q-Sepharose column (1.5×5 cm) which was equilibrated with Buffer B. The pooled fractions containing SOD-C33c obtained from chromatography on S-Sepharose was applied to the column. The column was then washed with Buffer B, and eluted with 60 ml of a gradient of 0.0 to 0.4 M NaCl in Buffer B. The flow rate for application, wash, and elution was 1 ml/min; collected fractions were 1 ml. All fractions from the Q-Sepharose column were analyzed as described for the S-Sepharose column. The peak of SOD-C33c eluted from the column at about 0.2 M NaCl.

The SOD-C33c obtained from the Q-Sepharose column was greater than about 90% pure, as judged by analysis on the polyacrylamide SDS gels and immunoblot using a monoclonal antibody directed against human SOD.

EXAMPLE 2

Synthesis of HCV Antigen C100

HCV antigen C100 contains sequences from the NS3 and NS4 domains (See EPO Pub. No. 318,216, Example IV.B.4-.6.) Specifically, it includes amino acids 1569–1931 of FIG. 1. This antigen was produced in yeast. A cDNA fragment of a 1270 bp encoding the above amino acids and heaving EcoRI termini was prepared.

The construction of a yeast expression vector in which this fragment was fused directly to the *S. cerevisiae* ADH2/GAP promoter was accomplished by a protocol which included amplification of the C100 sequence using a PCR method, followed by ligation of the amplified sequence into a cloning vector. After cloning, the C100 sequence was excised, and with a sequence which contained the ADH2/GAP promoter, was ligated to a large fragment of a yeast vector to yield a yeast expression vector.

The PCR amplification of C100 was performed using as template the vector pS3-56$_{C100m}$, which had been linearized by digestion with SalI. pS3-56, which is a pBR322 derivative, contains an expression cassette which is comprised of the ADH2/GAPDH hybrid yeast promoter upstream of the human superoxide dismutase gene, and a downstream alpha factor transcription terminator.

The oligonucleotide primers used for the amplification were designed to facilitate cloning into the expression vector, and to introduce a translation termination codon. Specifically, novel 5'-HindIII and 3'-SalI sites were generated with the PCR oligonucleotides. The oligonucleotide containing the SalI site also encodes the double termination codons, TAA and TGA. The oligonucleotide containing the HindIII site also contains an untranslated leader sequence derived from the pgap63 gene, situated immediately upstream of the AUG codon. The pEco63GAPDH gene is described by Holland and Holland (1980) and by Kniskern et al. (1986). The PCR primer sequences used for the direct expression of C100m were:

5' GAG TGC TCA AGC TTC AAA ACA AAA TGG CTC ACT TTC TAT CCC AGA CAA AGC AGA GT 3' (SEQ ID NO: 3) and 5' GAG TGC TCG TCG ACT CAT TAG GGG GAA ACA TGG TTC CCC CGG GAG GCG AA 3' (SEQ ID NO: 4).

Amplification by PCR, utilizing the primers, and template, was with a Cetus-Perkin-Elmer PCR kit, and was performed according to the manufacturer's directions. The PCR conditions were 29 cycles of 94° C. for a minute, 37° C. for 2 minutes, 72° C. for 3 minutes; and the final incubation was at 72° C. for 10 minutes. The DNA can be stored at 4° C. or −20° C. overnight.

After amplification, the PCR products were digested with HindIII and SalI. The major product of 1.1 kb was purified by electrophoresis on a gel, and the eluted purified product was ligated with a large SalI-HindIII fragment of pBR322. In order to isolate correct recombinants, competent HB101 cells were transformed with the recombinant vectors, and after cloning, the desired recombinants were identified on the basis of the predicted size of HindIII-SalI fragments excised from the clones. One of the clones which contained the a HindIII-SalI fragment of the correct size was named pBR322/C100 d. Confirmation that this clone contained amplified C100 was by direct sequence analysis of the HindIII-SalI fragment.

The expression vector containing C100 was constructed by ligating the HindIII-SalI fragment from pBR322/C100 d to a 13.1 kb BamHI-SalI fragment of pBS24.1, and a 1369 bm BamHI-HindIII fragment containing the ADH2/GAP promoter. (The latter fragment is described in EPO 164, 556). The pBS24.1 vector is described in commonly owned U.S. Ser. No. 382,805 filed Jul. 19, 1989. The ADH2/GAP promoter fragment was obtained by digestion of the vector pPGAP/AG/HindIII with HindIII and BamHI, followed by purification of the 1369 bp fragment on a gel.

Competent HB101 cells were transformed with the recombinant vectors; and correct recombinants were identified by the generation of a 2464 bp fragment and a 13.1 kb fragment generated by BamHI and SalI digestion of the cloned vectors. One of the cloned correct recombinant vectors was named pC100⁻d#3.

In order to express C100, competent cells of *Saccharomyces cerevisiae* strain AB122 (MATa leu2 ura3-53 prb 1-1122 pep4-3 prcl-407[cir-0]) were transformed with the expression vector pC100⁻d#3. The transformed cells were plated on URA-sorbitol, and individual transformants were then streaked on Leu⁻ plates.

Individual clones were cultured in Leu⁻, ura⁻ medium with 2% glucose at 30° C. for 24–36 hours. One liter of Yeast Extract Peptone Medium (YEP) containing 2% glucose was inoculated with 10 ml of the overnight culture, and the resulting culture was grown at 30° C. at an agitation rate of 400 rpm and an aeration rate of 1 L of air per 1 L of medium per minute (i.e., lvvm) for 48 hours. The pH of the medium was not controlled. The culture was grown in a BioFlo II fermentor manufactured by New Brunswick Science Corp. Following fermentation, the cells were isolated and analyzed for C100 expression.

Analysis for expressed C100 polypeptide by the transformed cells was performed on total cell lysates and crude extracts prepared from single yeast colonies obtained from the Leu⁻ plates. The cell lysates and crude extracts were analyzed by electrophoresis on SDS polyacrylamide gels, and by Western blots. The Western blots were probed with rabbit polyclonal antibodies directed against the SOD-C100 polypeptide expressed in yeast. The expected size of the C100 polypeptide is 364 amino acids. By gel analysis the expressed polypeptide has a $MW_r$ of 39.9K.

Both analytical methods demonstrated that the expressed C100 polypeptide was present in total cell lysates, but was absent from crude extracts. These results suggest that the expressed Cloo polypeptide may be insoluble.

EXAMPLE 3

Expression of HCV Antigen S2

HCV antigen S2 contains a sequence from the hydrophobic N-terminus of the S domain. It includes amino acids 199–328 of FIG. 1.

The protocol for the construction of the expression vector encoding the S2 polypeptide and for its expression in yeast was analogous to that used for the expression of the C100 polypeptide, described in Example 2.

The template for the PCR reaction was the vector pBR322/Pi14a, which had been linearized by digestion with HindIII. Pi14a is a cDNA clone that encodes amino acids 199–328.

The oligonucleotides used as primers for the amplification by PCR of the S2 encoding sequence were the following. For the 5'-region of the S2 sequence:

5' GAG TGC TCA AGC TTC AAA ACA AAA TGG GGC TCT ACC ACG TCA CCA ATG ATT GCC CTA AC 3' (SEQ ID NO: 5); and for the 3'-region of the S2 sequence:

5'GAG TGC TCG TCG ACT CAT TAA GGG GAC CAG TTC ATC ATC ATA TCC CAT GCC AT 3' (SEQ ID NO: 6).

The primer for the 5'-region introduces a HindIII site and an ATG start codon into the amplified product. The primer for the 3'-region introduces translation stop codons and a SalI site into the amplified product.

The PCR conditions were 29 cycles of 94° C. for a minute, 37° C. for 2 minutes, 72° C. for 3 minutes, and the final incubation was at 72° C. for 10 minutes.

The main product of the,PCR reaction was a 413 bp fragment, which was gel purified. The purified fragment was ligated to the large fragment obtained from pBR322 digested with HindIII and SalI fragment, yielding the plasmid pBR322/S2d.

Ligation of the 413 bp HindIII-SalI S2 fragment with the 1.36 kb BamHI-HindIII fragment containing the ADH2/GAP promoter, and with the large BamHI-SalI fragment of the yeast vector pBS24.1 yielded recombinant vectors, which were cloned. Correct recombinant vectors were identified by the presence of a 1.77 kb fragment after digestion with BamHI and SalI. An expression vector constructed from the amplified sequence, and containing the sequence encoding S2 fused directly to the ADH2/GAP promoter is identified as pS2d#9.

EXAMPLE 4

Synthesis of HCV C Antigen

HCV antigen C22 is from the C domain. It comprises amino acids 1-122 of FIG. 1.

The protocol for the construction of the expression vector encoding the C polypeptide and for its expression in yeast was analogous to that used for the expression of the C100 polypeptide, described supra, except for the following.

The template for the PCR reaction was pBR322/Ag30a which had been linearized with HindIII. Ag30 is a cDNA clone that encodes amino acids 1–122. The oligonucleotides used as primers for the amplification by PCR of the C encoding sequence were the following. For the 5'-region of the C sequence:

5' GAG TGC AGC TTC AAA ACA AAA TGA GCA CGA ATC CTA AAC CTC AAA AAA AAA AC 3' (SEQ ID NO: 7), and for the 3'-region of the C sequence:

5' GAG TGC TCG TCG ACT CAT TAA CCC AAA TTG CGC GAC CTA CGC CGG GGG TCT GT 3' (SEQ ID NO: 8).

The primer for the 5'-region introduces a HindIII site into the amplified product, and the primer for the 3'-region introduces translation stop codons and a SalI site.

The PCR was run for 29 cycles of 94° C. for a minute, 37° C. for 2 minutes, 72° C. for 3 minutes, and the final incubation was at 72° C. for 10 minutes.

The major product of PCR amplification is a 381 bp polynucleotide. Ligation of this fragment with the SalI-HindIII large SalI-HindIII fragment of pBR322 yielded the plasmid pBR322/C2.

Ligation of the 381 bp HindIII-SalI C coding fragment excised from pBR322/C2 with the 1.36 kb BamHI-HindIII fragment containing the ADH2/GAP promoter, and with the large BamHI-SalI fragment of the yeast vector pBS24.1 yielded recombinant vectors, which were cloned. Correct recombinant vectors were identified by the presence of a 1.74 kb fragment after digestion with BamHI and SalI. An expression vector constructed from the amplified sequence, and containing the sequence encoding C fused directly to the ADH2/GAP promoter is identified as pC22.

Analysis for expressed C polypeptide by the transformed cells was performed on total cell lysates and crude extracts prepared from single yeast colonies obtained from the Leu plates. The cell lysates and crude extracts were analyzed by electrophoresis on SDS polyacrylamide gels. The C polypeptide is expected to have 122 amino acids and by gel analysis the expressed polypeptide has a $MW_r$ of approximately 13.6 Kd.

EXAMPLE 5

Synthesis of NS5 Polypeptide

This polypeptide contains sequence from the N-terminus of the NS5 domain. Specifically it includes amino acids 2054 to 2464 of FIG. 1. The protocol for the construction of the expression vector encoding the NS5 polypeptide and for its expression were analogous to that used for the expression of C33c (see Example 1).

Another NS5 domain antigen was made by preparing a coding sequence for amino acids 2054–2995 of FIG. 1 and ligating it into a yeast SOD fusion expression vector (pSOD/NS5) in a manner analogous to Example 1 above and expressing it in *S. cerevisiae* strain JSC 308, as described in EPO Pub. No. 318,216, Examples IV.B.0.4–0.6.

EXAMPLE 6

Fusion Proteins

In addition to the C100 fusion protein described above, several other fusion proteins were prepared.

A fusion of NS3 and NS4 domains, called c200 was prepared. The c200 polypeptide spans amino acids 1192–1931 of FIG. 1. An expression plasmid pAB24-c200, which is a yeast SOD fusion expression vector containing a coding sequence for c200 was prepared in a manner analogous to the c100-3 vector in EPO Pub. No. 318,216, Example IV.B.0.4–0.6, and expressed in *S. cerevisiae* JSC308. Id. c200 can be used in place of c100 in the above-described antigen panels. See also U.S. Ser. No. 07/456,637, filed Dec. 21, 1989, Examples IV.A.37 and IV.B.10, incorporated herein by reference.

A fusion of core, NS3 and NS4 called c22/c200 was prepared. The coding domain for the expression plasmid, pSOD/core/c200, encodes amino acids 2–120, 1192–1931 of FIG. 1. This plasmid, a yeast SOD expression vector for core fused to c200, was prepared in a manner analogous to Example 2, above, and expressed in *S. cerevisiae* JSC308.

Figure 3:
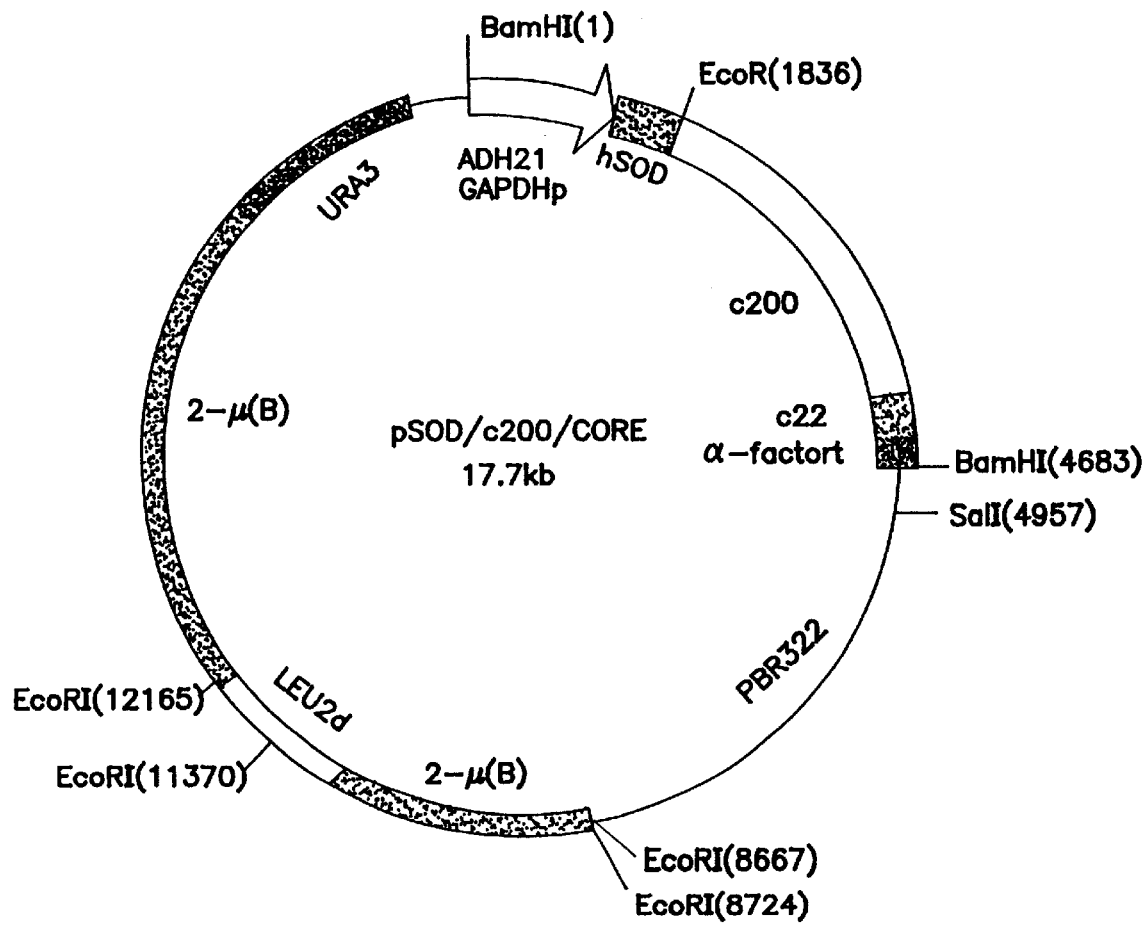
FIG. 3 is a map showing some of the features of the plasmid pSOD/c200/core.

A variation of the above fusion, called c200/c22, was also prepared. In this antigen, the core domain is located at the carboxy rather than the amino terminus of the protein. The expression plasmid, pSOD/c200/core (FIG. 3), has an HCV coding sequence for amino acids 1192–1931, 2–120 (FIG. 4). The vector was preapred as described in Example 2, above, and expressed in *S. cerevisiae* JSC 308.

EXAMPLE 7

Radioimmunoassay (RIA) for Antibodies to HCV

The HCV antigens of Examples 1–5 were tested in an RIA format for their ability to detect antibodies to HCV in the serum of individuals clinically diagnosed as having HCV (Non-A, Non-B) and in serum from blood given by paid blood donors.

The RIA was based upon the procedure of Tsu and Herzenberg (1980) in SELECTED METHODS IN CELLULAR IMMUNOLOGY (W. H. Freeman & Co.), pp. 373–391. Generally, microtiter plates (Immulon 2, Removawell strips) are coated with purified HCV antigen. The coated plates are incubated with the serum samples or appropriate controls. During incubation, antibody, if present, is immunologically bound to the solid phase antigen. After removal of the unbound material and washing of the microtiter plates, complexes of human antibody-NANBV antigen are detected by incubation with $^{125}$I-labeled sheep anti-human immunoglobulin. Unbound labeled antibody is removed by aspiration, and the plates are washed. The radioactivity in individual wells is determined; the amount of bound human anti-HCV antibody is proportional to the radioactivity in the well.

Specifically, one hundred microliter aliquots containing 0.1 to 0.5 micrograms of the HCV antigen in 0.125 M Na borate buffer, pH 8.3, 0.075 M NaCl (BBS) was added to each well of a microtiter plate. (Dynatech Immulon 2 Removawell Strips). The plate was incubated at 4° C. overnight in a humid chamber, after which, the antigen solution was removed and the wells washed 3 times with BBS containing 0.02% TritonX-100™ surfactant, (BBST). To prevent nonspecific binding, the wells were coated with bovine serum albumin (BSA) by addition of 100 microliters of a 5 mg/ml solution of BSA in BBS followed by incubation at room temperature for 1 hour; after this incubation the BSA solution was removed. The antigens in the coated wells were reacted with serum by adding 100 microliters of serum samples diluted 1:100 in 0.01M Na phosphate buffer, pH 7.2, 0.15 M NaCl (PBS) containing 10 mg/ml BSA, and incubating the serum containing wells for 1 hr at 37° C. After incubation, the serum samples were removed by aspiration, and the wells were washed 5 times with BBST. Antibody bound to the antigen was determined by the binding of $^{125}$I-labeled F' (ab)$_2$ sheep anti-human IgG to the coated wells. Aliquots of 100 microliters of the labeled probe (specific activity 5–20 microcuries/microgram) were added to each well, and the plates were incubated at 37° C. for 1 hour, followed by removal of excess probe by aspiration, and 5 washes with BBST. The amount of radioactivity bound in each well was determined by counting in a counter which detects gamma radiation.

Table 1 below presents the results of the tests on the serum from individuals diagnosed as having HCV. The NS5 antigen used in the immunoassays referred to in Table 1 is the antigen spanning amino acids 2054–2464 of FIG. 1 described in Example 5, above."

TABLE 1

| INDIVIDUAL | S2 | C22 | C100 | C33c | NS5 |
|---|---|---|---|---|---|
| CVH IVDA | P | P | P(+++) | P | P |
| CVH IVDA | P | P | P(+) | P | P |
| CVH IVDA | P | P | P(+) | P | P |
| CVH NOS | P | P | P | P | P |
| AVH NOS HS | N | N | N | N | N |
| AVH NOS HS | P | N | N | N | N |
| AVH NOS HS | P | N | N | N | N |
| AVH NOS HS | P/N | N | N | N | N |
| AVH PTVH | N | N | N | P/N | N |
| AVH NOS HS | N | N | N | N | N |
| AVH NOS | N | N | N | N | P |
| AVH PTVH | N | N | N | N | N |
| AVH IVDA | N | P | N | P | P |
| AVH PTVH | P | P/N | N | N | P |
| AVH NOS | N | P | N | N | N |
| AVH IVDA | N | P | N | P | P |
| AVH NOS HS | P/N | N | N | N | N |
| AVH PTVH | N | N | N | N | N |
| CVH IVDA | P | P | P | P | P |
| CVH IVDA | P | P | P | P | P |
| AVH NOS HS | N | N | N | N | N |
| CVH PTVH | P | P | N | P | P |
| AVH PTVH | P | N | P(+) | P(+++) | N |
| CVH PTVH | N | P | P | P | P |
| CVH NOS HS | P | P | P | P | N |
| CVH NOS | N | P | P/N | P | P |
| CVH IVDA | N | N | N | P | N |
| AVH IVDA | P | P | P | P | P |
| AVH IVDA | P | P | P | P | P |
| CVH IVDA | P | P | P | P | P |
| AVH IVDA | P/N | P | P | P | P |
| AVH IVDA | N | P | P | P | N |
| CVH PTVH | P | P/N | N | N | N |
| CVH NOS | N | N | N | N | N |
| CVH NOS | N | N | N | N | N |
| CVH IVDA | P | P | P | P | P |
| AVH IVDA | P | P | P | P | P |
| CVH PTVH | P | P | P | P | P |
| AVH PTVH | N | P | P | P | P |
| AVH IVDA | N | P | N | P | N |
| AVH NOS | N | N | N | N | N |
| AVH NOS | N | N | N | N | N |
| CVH NOS | N | P | N | N | P |
| CVH NOS | P | P | N | N | P |
| CVH NOS HS | P | P | P | P | P |
| CVH PTVH | P | P | N | P | P |
| AVH nurse | P | P | N | N | N |
| AVH IVDA | P | P | P | P | N |
| AVH IVDA | N | P | P(+) | P(+++) | N |
| AVH nurse | P/N | P | N | N | N |
| AVH PTVH | P/N | P | P | N | P |
| AVH NOS | N | P/N | N | N | P |
| AVH NOS | N | P | N | P | N |
| AVH PTVH | P | P/N | N | N | N |
| AVH PTVH | N | P | N | P | P |
| AVH PTVH | P | P | P | P | P |
| AVH PTVH | N | P | N | N | P |
| CVH PTVH | P/N | P | P(+) | P(+++) | N |
| AVH PTVH | N | P/N | P(+) | P(+++) | P |
| AVH PTVH | P | (?) | P | N | P |
| CVH PTVH | N | P | N | P | P |
| CVH PTVH | N | P | P | P | P |
| CVH PTVH | N | N | N | N | N |
| AVH NOS | N | N | N | N | N |
| AVH nurse | P | P | N | N | N |
| CVH PTVH | N | P | N | N | P |
| AVH IVDA | N | P | N | P/N | N |
| CVH PTVH | P | P | P(+) | P(+++) | P |
| AVH NOS | P | P | N | N | N |
| AVH NOS | P/N | P | N | N | P |
| AVH PTVH | P/N | P | P | P | P |
| AVH NOS | N | P | P | P | P/N |
| AVH IVDA | N | P | N | N | P |
| AVH NOS | N | P/N | N | N | N |
| AVH NOS | P | P | N | N | P |
| AVH PTVH | N | P | P | p | P |
| crypto | P | P | P | P | P |
| CVH NOS | N | P | P | P | P |
| CVH NOS | N | N | N | N | N |
| AVH PTVH | N | P | P(+) | P(++) | N |
| AVH PTVH | N | P/N | P(+) | P(++) | P |
| AVH PTVH | N | P/N | P(+) | P(++) | P |
| CVH IVDA | P | P | P | P | P |
| CVH IVDA | P | P | P | P | P |
| CVH IVDA | P | P | P | P | P |
| CVH IVDA | P | P | P | P | P |
| AVH NOS | N | P | N | N | N |
| CVH IVDA | P | P | P | P | P/N |
| AVH IVDA | P | P | P | P | N |
| AVH NOS | P | P | N | N | N |
| AVH NOS | P | P | N | N | N |
| CVH PTVH | P | P | N | N | P/N |
| AVH PTVH | N | P | N | P | P |
| AVH NOS | N | N | N | N | N |
| AVH NOS | N | P | N | N | N |
| AVH NOS | P | N | N | N | N |
| CVH NOS | N | N | N | N | N |
| AVH NOS | N | P/N | N | N | N |
| AVH IVDA | N | P | P | P | P |
| crypto | N | P | N | N | P/N |
| crypto | P | P | P/N | P | P |
| AVH IVDA | N | N | P | P | N |
| AVH IVDA | N | P | P | P | N |
| AVH NOS | N | N | N | N | N |
| AVH NOS | N | N | N | N | N |
| CVH IVDA | P | P | P | P | P |
| CVH PTVH | N | N | N | N | N |
| CVH PTVH | P | P | P(+) | P(+++) | P |
| CVH PTVH | P | P | P(+) | P(+++) | P |
| CVH NOS | P/N | N | N | N | N |
| CVH NOS | N | N | N | N | N |
| CVH PTVH | P | P | P | P | P |
| CVH PTVH | P | P | P | P | P |
| CVH PTVH | P | P | P | P | P |
| AVH IVDA | N | P | P | P | P |
| CVH NOS | N | N | N | N | N |
| CVH NOS | N | N | N | N | N |
| CVH PTVH | P | P | P | P | P |
| AVH NOS | P | P | N | N | P/N |
| AVH NOS | N | P/N | N | N | N |
| CVH PTVH | P | P | N | N | P |
| CVH NOS | N | P/N | N | N | N |
| AVH NOS | N | P | N | N | N |
| AVH NOS | N | P | N | N | N |
| CVH PTVH | N | P | N | N | N |
| AVH IVDA | N | P | N | P | P |
| AVH NOS | P | N | N | N | N |
| CVH NOS | N | N | N | N | N |

TABLE 1-continued

| INDIVIDUAL | S2 | C22 | C100 | C33c | NS5 |
|---|---|---|---|---|---|
| CVH NOS | N | N | N | N | N |
| CVH IVDA | P | P | P | P | P |
| CVH IVDA | P/N | P | P | P | P |
| CVH IVDA | P | P | P | P | P |
| CVH IVDA | N | P | P | P | P |
| AVH NCS | N | P | N | N | N |
| CVH IVDA | N | P | N | N | P |
| CVH IVDA | N | P | N | N | P |
| AVH PTVH | P | P | N | P | P |
| AVH PTVH | P | P | N | P | P |
| CVH NOS | N | P | N | N | P/N |
| CVH NOS | N | P | N | N | N |
| CVH NOS | N | N | N | N | N |
| CVH PTVH | P | P | P | P | P |
| CVH PTVH | P | P | P | P | P |
| CVH PTVH | P | P | P | P | P |
| AVH IVDA | N | P | N | N | P |
| AVH IVDA | N | P | P(++) | P(+) | P |
| CVH PTVH | P | P | P | P | P |
| AVH PTVH | N | P | P | P | P |
| CVH PTVH? | N | P | P | P | P |
| CVH PTVH? | P/N | P | P | P | P |
| CVH NOS HS | P | P | N | N | N |
| CVH IVDA | P | P | P | P | N |
| CVH PTVH | N | P | P | P | P |
| CVH PTVH | P | P | P | P | P/N |
| CVH NOS | P | P | P | P | P |
| CVH IVDA | P | P | P | P | P |
| CVH PTVH | P | P | P | P | N |
| CVH PTVH | P | P | P | P | P |
| CVH NOS | N | N | N | N | P/N |
| CVH NOS | N | P/N | N | N | P/N |
| CVH PTVH | P | P | P | P | P |
| CVH NOS | N | P | N | N | N |
| CVH NOS | N | N | N | N | N |
| CVH NOS | P | P | N | N | P/N |
| CVH NOS | N | N | N | N | N |
| CVH NOS HS | P | P | P | P | P |
| CVH NOS HS | P | P | P | P | P |
| CVH PTVH | N | N | N | N | N |
| AVH PTVH | N | P | P | P | P |
| AVH NOS | | | — | — | |
| CVH PTVH | N | P | P/N | P(+++) | N |
| crypto | P | P | P | P | P |
| crypto | P | P | P | P | P |
| crypto | N | P | N | N | N |
| crypto | N | P | P | P | P |
| CVH PTVH | P | P | P | P | P |
| crypto | N | N | N | N | N |
| crypto | N | P | N | N | P/N |
| crypto | N | P | N | N | P |
| crypto | P | P | P | P | P |
| crypto | N | P | N | P | N |
| crypto | | | — | — | |
| crypto | | | — | — | |
| CVH NOS | | | — | — | |
| AVH-IVDA | N | P | N | P(+) | P |
| AVH-IVDA | N | P/N | N | P(++) | N |

AVH = acute viral hepatitis
CVH = chronic viral hepatitis
PTVH = post-transfusion viral hepatitis
IVDA = intravenous drug abuser
crypto = cryptogenic hepatitis
NOS = non-obvious source
P = positive
N = negative Per these results, no single antigen reacted with all sera. C22 and C33c were the most reactive and S2 reacted with some sera from some putative acute HCV cases with which no other antigen reacted. Based on these results, the combination of two antigens that would provide the greatest range of detection is C22 and C33c. If one wished to detect a maximum of acute infections, S2 would be included in the combination.

Table 2 below presents the results of the testing on the paid blood donors.

TABLE 2

| Donor | C100 | C33c | C22 | S2 | NS5 |
|---|---|---|---|---|---|
| 1 | N | N | N | N | N |
| 2 | N | N | N | N | N |
| 3 | P | P | P | P | P |
| 4 | N | N | N | N | N |
| 5 | N | N | N | N | N |
| 6 | N | N | N | N | N |
| 7 | N | N | N | N | N |
| 8 | N | N | N | N | N |
| 9 | N | N | N | N | N |
| 10 | N | N | N | N | N |
| 11 | N | N | N | N | N |
| 12 | N | N | N | N | N |
| 13 | N | N | N | N | N |
| 14 | N | N | N | N | N |
| 15 | N | N | N | N | N |
| 16 | N | N | N | N | N |
| 17 | N | N | N | N | N |
| 18 | P | P | P | P | P |
| 19 | P | P | N | P | P |
| 20 | P | P | N | P | P |
| 21 | N | N | N | N | N |
| 22 | N | P | P | N | P |
| 23 | P | P | P | P | P |
| 24 | N | N | N | N | N |
| 25 | N | N | N | N | N |
| 26 | N | N | N | N | N |
| 27 | N | N | N | N | N |
| 28 | N | N | N | N | N |
| 29 | N | N | N | N | N |
| 30 | N | N | N | N | N |
| 31 | P | P | P | N | P |
| 32 | N | N | N | N | N |
| 33 | N | N | N | N | N |
| 34 | N | N | N | N | P |
| 35 | N | N | P | N | N |
| 36 | N | N | N | N | N |
| 37 | N | N | N | N | N |
| 38 | N | N | N | N | N |
| 39 | N | N | N | N | N |
| 40 | N | N | N | N | N |
| 41 | N | N | N | N | P |
| 42 | N | N | N | N | N |
| 43 | N | N | N | N | N |
| 44 | N | N | N | N | N |
| 45 | N | N | N | N | N |
| 46 | N | N | N | N | N |
| 47 | P | P | N | N | P |
| 48 | N | N | N | N | N |
| 49 | N | N | N | N | N |
| 50 | N | N | N | N | N |
| 51 | N | P | P | N | P |
| 52 | N | N | N | N | N |
| 53 | N | P | P | N | P |
| 54 | P | P | P | P | N |
| 55 | N | N | N | N | N |
| 56 | N | N | N | N | N |
| 57 | N | N | N | N | N |
| 58 | N | N | N | N | N |
| 59 | N | N | N | N | N |
| 60 | N | N | N | N | N |
| 61 | N | N | N | N | N |
| 62 | N | N | N | N | N |
| 63 | N | N | N | N | N |
| 64 | N | N | N | N | N |
| 65 | N | N | N | N | N |
| 66 | N | N | N | N | N |
| 67 | N | N | N | N | N |
| 68 | N | N | N | N | N |
| 69 | N | N | N | N | N |
| 70 | P | P | P | P | P |

TABLE 2-continued

| Donor | C100 | C33c | C22 | S2 | NS5 |
|---|---|---|---|---|---|
| 71 | N | N | N | N | N |
| 72 | N | N | N | N | N |
| 73 | P | P | P | P | N |
| 74 | N | N | N | N | N |
| 75 | N | N | N | N | N |
| 76 | N | N | N | N | P |
| 77 | N | N | N | N | N |
| 78 | N | N | N | N | N |
| 79 | N | N | N | N | N |
| 80 | N | N | N | N | N |
| 81 | N | N | N | N | N |
| 82 | N | N | N | N | N |
| 83 | P | P | N | N | N |
| 84 | N | N | P | N | N |
| 85 | N | N | N | N | N |
| 86 | P | P | P | P | N |
| 87 | N | N | N | N | N |
| 88 | N | N | N | N | N |
| 89 | P | P | P | P | P |
| 90 | P | P | P | P | N |
| 91 | N | N | N | N | P |
| 92 | P | P | P | N | N |
| 93 | N | N | N | N | N |
| 94 | N | N | N | N | N |
| 95 | N | N | N | N | N |
| 96 | N | N | N | N | N |
| 97 | N | N | N | N | N |
| 98 | N | P | P | P | P |
| 99 | P | P | P | P | P |
| 100 | N | N | N | N | N |
| 101 | P | P | P | P | P |
| 102 | N | N | N | N | N |
| 103 | N | N | N | N | N |
| 104 |   | N | N | N | N |
| 105 | P | P | P | P | N |
| 106 | N | N | N | N | N |
| 107 | N | N | N | N | N |
| 108 | N | N | N | N | N |
| 109 | P | P | P | P | P |
| 110 | P | P | P | N | P |
| 111 | P | P | P | N | P |
| 112 | N | N | N | N | N |
| 113 | P | P | P | P | P |
| 114 | N | N | N | N | N |
| 115 | N | N | N | N | N |
| 116 | P | P | P | P | P |
| 117 | N | N | N | N | N |
| 118 | N | N | N | N | N |
| 119 | N | N | N | N | N |
| 120 | P | P | P | P | P |
| 121 | N | N | N | N | N |
| 122 | N | P | P | N | P |
| 123 | N | N | N | N | N |
| 124 | N | N | N | N | N |
| 125 | N | N | N | N | N |
| 126 | P | N | N | N | N |
| 127 | N | N | N | N | N |
| 128 | N | N | N | N | N |
| 129 | N | N | N | N | N |
| 130 | P | P | P | P | N |
| 131 | N | N | N | N | P |
| 132 | N | N | N | N | N |
| 133 | N | N | N | N | N |
| 134 | N | N | N | N | N |
| 135 | N | N | N | N | N |
| 136 | N | N | N | N | N |
| 137 | N | N | N | N | N |
| 138 | N | N | N | N | N |
| 139 | N | N | N | N | N |
| 140 | P | N | N | N | N |
| 141 | P | N | P | P | P |
| 142 | N | N | N | N | N |
| 143 | N | N | N | N | N |
| 144 | N | N | N | N | N |
| 145 | N | N | N | N | N |
| 146 | N | N | N | N | N |
| 147 | N | N | N | N | N |
| 148 | N | N | N | N | N |
| 149 | N | N | N | N | N |
| 150 | N | N | N | N | N |
| 151 | N | N | N | N | N |
| 152 | N | N | N | N | N |
| 153 | N | N | N | N | N |
| 154 | P | P | P | P | P |
| 155 | N | N | N | N | N |
| 156 | N | N | N | N | N |
| 157 | N | N | N | N | N |
| 158 | N | N | N | N | N |
| 159 | N | N | N | N | N |
| 160 | N | N | N | N | N |
| 161 | P | P | P | P | P |
| 162 | N | N | N | N | N |
| 163 | N | N | N | N | N |
| 164 | P | P | P | N | P |
| 165 | N | N | N | N | N |
| 166 | P | P | P | N | P |
| 167 | N | N | N | N | N |
| 168 | N | N | N | N | N |
| 169 | N | N | N | N | N |
| 170 | N | N | N | N | N |
| 171 | N | N | N | N | N |
| 172 | N | N | N | N | N |
| 173 | N | N | N | N | N |
| 174 | N | N | N | N | N |
| 175 | N | N | N | N | N |
| 176 | N | N | N | N | N |
| 177 | N | N | N | N | P |
| 178 | N | N | N | N | N |
| 179 | N | N | N | N | N |
| 180 | N | N | N | N | N |
| 181 | N | N | N | N | N |
| 182 | N | N | N | N | N |
| 183 | P | P | P | P | P |
| 184 | N | N | N | N | N |
| 185 | N | N | N | N | N |
| 186 | N | N | N | N | N |
| 187 | N | N | N | N | N |
| 188 | N | P | P | N | N |
| 189 | N | N | N | N | N |
| 190 | N | N | N | N | N |
| 191 | N | N | N | N | N |
| 192 | N | N | N | N | N |
| 193 | N | N | N | N | N |
| 194 | N | N | N | N | N |
| 195 | N | N | N | N | N |
| 196 | N | N | N | N | N |
| 197 | N | N | N | N | P |
| 198 | P | P | P | N | N |
| 199 | N | N | N | N | P |
| 200 | P | P | P | P | N |

The results on the paid donors generally confirms the results from the sera of infected individuals.

EXAMPLE 7

ELISA Determinations of HCV Antibodies Using Combination of HCV Antigens

Plates coated with a combination of C22 and C33c antigens are prepared as follows. A solution containing coating buffer (5mM Na Borate, pH 9.0), 21 ml/plate, BSA (25 micrograms/ml), C22 and C33c (2.50 micrograms/ml each) is prepared just prior to addition to the Removeawell Immulon I plates (Dynatech Corp.). After mixing for 5 minutes, 0.2 ml/well of the solution is added to the plates, they are covered and incubated for 2 hours at 37° C., after which the solution is removed by aspiration. The wells are washed once with 400 microliters wash buffer (100 mM sodium phosphate, pH 7.4, 140 mM sodium chloride, 0.1% (W/V) casein, 1% (W/V) Triton X-100™ surfactant 0.01% (W/V) Thimerosal). After removal of the wash solution, 200 microliters/well of Postcoat solution (10 mM sodium phosphate, pH 7.2, 150 mM sodium chloride, 0.1% (w/v) casein, 3% sucrose and 2 mM phenylmethylsulfonylfluoride (PMSF)) is added, the plates are loosely covered to prevent evaporation, and are allowed to stand at room temperature for 30 minutes. The wells are then aspirated to remove the solution, and lyophilized dry overnight, without shelf heating. The prepared plates may be stored at 2–8° C. in sealed aluminum pouches with dessicant (3 g Sorb-it™ packs).

In order to perform the ELISA determination, 20 microliters of serum sample or control sample is added to a well containing 200 microliters of sample diluent (100 mM sodium phosphate, pH 7.4, 500 mM sodium chloride, 1 mM EDTA, 0.1% (W/V) Casein, 0.01% (W/V) Thimerosal, 1% (W/V) Triton X-100™ surfactant 100 micrograms/ml yeast extract). The plates are sealed, and are incubated at 37° C. for two hours, after which the solution is removed by aspiration, and the wells are washed three times with 400 microliters of wash buffer (phosphate buffered saline (PBS) containing 0.05% Tween 20). The washed wells are treated with 200 microliters of mouse anti-human IgG-horse radish peroxidase (HRP) conjugate contained in a solution of Ortho conjugate diluent (10 mM sodium phosphate, pH 7.2, 150 mM sodium chloride, 50% (V/V) fetal bovine serum, 1% (V/V) heat treated horse serum, 1 mM $K_3Fe(CN)_6$, 0.05% (W/V) Tween 20, 0.02% (W/V) Thimerosal). Treatment is for 1 hour at 37° C., the solution is removed by aspiration, and the wells are washed three times with 400 ml wash buffer, which is also removed by aspiration. To determine the amount of bound enzyme conjugate, 200 microliters of substrate solution (10 mg O-phenylenediamine dihydrochloride per 5 ml of Developer solution) is added. Developer solution contains 50 mM sodium citrate adjusted to pH 5.1 with phosphoric acid, and 0.6 microliters/ml of 30% $H_2O_2$. The plates containing the substrate solution are incubated in the dark for 30 minutes at room temperature, the reactions are stopped by the addition of 50 microliters/ml 4N sulfuric acid, and the ODs determined.

In a similar manner, ELISAs using fusion proteins of C22 and C33c, and C22, C33c, and S2 and combinations of C22 and C100, C22 and S2, C22 and an NS5 antigen, C22, C33c, and S2, and C22, C100, and S2 may be carried out.

Modifications of the above-described modes for carrying out the invention that are obvious to those of skill in the fields of molecular biology, immunology, and related fields are intended to be within the scope of the following claims.

We claim:

1. A combination of hepatitis C viral (HCV) antigens for use in an immunoassay comprising:
   (a) a first HCV antigen comprising the C domain or an immunologically reactive fragment thereof containing at least 8 amino acids, said C domain consisting of amino acids 1 to 120 of the HCV polyprotein; and
   (b) a second HCV antigen selected from the group consisting of:
   (i) an HCV antigen consisting of the NS3 domain or an immunologically reactive fragment thereof containing at least 8 amino acids, said NS3 domain consisting of amino acids 1050 to 1640 of the HCV polyprotein;
   (ii) an HCV antigen consisting of the NS4 domain or an immunologically reactive fragment thereof containing at least 8 amino acids, said NS4 domain consisting of amino acids 1640 to 2000 of the HCV polyprotein;
   (iii) an HCV antigen comprising the S domain or an immunologically reactive fragment thereof containing at least 8 amino acids, said S domain consisting of amino acids 120 to 400 of the HCV polyprotein; and
   (iv) an HCV antigen comprising the NS5 domain or an immunologically reactive fragment thereof containing at least 8 amino acids, said NS5 domain consisting of amino acids 2000 to 3011 of the HCV polyprotein.

2. A combination of hepatitis C viral (HCV) antigens according to claim 1, wherein said second antigen consists of the NS3 domain or an immunologically reactive fragment thereof containing at least 8 amino acids, said NS3 domain consisting of amino acids 1050 to 1640 of the HCV polyprotein.

3. A combination of hepatitis C viral (HCV) antigens according to claim 1, wherein said second antigen consists of the NS4 domain or an immunologically reactive fragment thereof containing at least 8 amino acids, said NS4 domain consisting of amino acids 1640 to 2000 of the HCV polyprotein.

4. A combination of hepatitis C viral (HCV) antigens according to claim 1, wherein said second antigen comprises the S domain or an immunologically reactive fragment thereof containing at least 8 amino acids, said S domain consisting of amino acids 120–400 of the HCV polyprotein.

5. A combination of hepatitis C viral (HCV) antigens according to claim 1, wherein said second antigen comprises the NS5 domain or an immunologically reactive fragment thereof containing at least 8 amino acids, said NS5 domain consisting of amino acids 2000–3011 of the HCV polyprotein.

6. A combination of hepatitis C viral (HCV) antigens according to claim 1, wherein said second antigen is amino acids 1192–1457 of the HCV polyprotein or an immunologically reactive fragment thereof containing at least 8 amino acids.

7. A combination of hepatitis C viral (HCV) antigens according to claim 1, wherein said second antigen is amino acids 199–328 of the HCV polyprotein or an immunologically reactive fragment thereof containing at least 8 amino acids.

8. A combination of hepatitis C viral (HCV) antigens according to claim 1, wherein said second antigen is amino acids 2054–2464 of the HCV polyprotein or an immunologically reactive fragment thereof containing at least 8 amino acids.

9. A combination of hepatitis C viral (HCV) antigens according to claim 1, wherein said first HCV antigen is amino acids 1–120 of the HCV polyprotein.

10. A combination of hepatitis C viral (HCV) antigens for use in an immunoassay comprising:
   (a) a first HCV antigen which is amino acids 1–122 of the HCV polyprotein, or an immunologically reactive fragment of said first antigen containing at least 8 amino acids; and
   (b) a second HCV antigen selected from the group consisting of:
   (i) an HCV antigen comprising the NS3 domain or an immunologically reactive fragment thereof containing at least 8 amino acids, said NS3 domain consisting of amino acids 1050 to 1640 of the HCV polyprotein;
   (ii) an HCV antigen comprising the NS4 domain or an immunologically reactive fragment thereof containing at least 8 amino acids, said NS4 domain consisting of amino acids 1640 to 2000 of the HCV polyprotein;
   (iii) an HCV antigen comprising the S domain or an immunologically reactive fragment thereof containing at least 8 amino acids, said S domain consisting of amino acids 120 to 400 of the HCV polyprotein;
   (iv) an HCV antigen comprising the NS5 domain or an immunologically reactive fragment thereof containing at least 8 amino acids, said NS5 domain consisting of amino acids 2000 to 3011 of the HCV polyprotein.

11. A combination of hepatitis C viral (HCV) antigens for use in an immunoassay comprising:
   (a) a first HCV antigen which is amino acids 9–177 of the HCV polyprotein; and
   (b) a second HCV antigen selected from the group consisting of:
   (i) an HCV antigen comprising the NS3 domain or an immunologically reactive fragment thereof containing at least 8 amino acids, said NS3 domain consisting of amino acids 1050 to 1640 of the HCV polyprotein;
   (ii) an HCV antigen comprising the NS4 domain or an immunologically reactive fragment thereof containing at least 8 amino acids, said NS4 domain consisting of amino acids 1640 to 2000 of the HCV polyprotein;
   (iii) an HCV antigen comprising the S domain or an immunologically reactive fragment thereof containing at least 8 amino acids, said S domain consisting of amino acids 120 to 400 of the HCV polyprotein; and (iv) an HCV antigen comprising the NSS domain or an immunologically reactive fragment thereof containing at least 8 amino acids, said NS5 domain consisting of amino acids 2000 to 3011 of the HCV polyprotein.

12. A combination according to claims 1, 2, 3, 4, 5, 6, 7, 8, 9, 10, or 11, wherein said HCV antigens are produced by recombinant expression or chemical synthesis.

13. A combination according to claims 1, 2, 3, 4, 5, 6, 7, 8, 9, 10, or 11, wherein the combination is in the form of a fusion polypeptide.

14. A combination according to claims 1, 2, 3, 4, 5, 6, 7, 8, 9, 10, or 11, wherein the combination is in the form of said first HCV antigen and said second antigen individually bound to a common solid matrix.

15. A combination according to claim 14, wherein the solid matrix is selected from the group consisting of the surface of a microtiter plate well, a bead and a dipstick.

16. A combination according to claims 1, 2, 3, 4, 5, 6, 7, 8, 9, 10, or 11, wherein the combination is in the form of a mixture of said first HCV antigen and said second antigen.

17. A combination according to claims 1, 2, 3, 4, 5, 6, 7, 8, 9, 10, or 11, wherein the combination is packaged into a kit further comprising standard control reagents and instructions for detecting antibodies to hepatitis C virus (HCV) in a mammalian body component suspected of containing said antibodies.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GATCCTGGAA TTCTGATAA      19

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

AATTTTATCA GAATTCCAG      19

(2) INFORMATION FOR SEQ ID NO:3:

(i) SEQUENCE CHARACTERISTICS:
      (A) LENGTH: 56 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

GAGTGCTCAA GCTTCAAAAC AAAATGGCTC ACTTTCTATC CCAGACAAAG CAGAGT        56

(2) INFORMATION FOR SEQ ID NO:4:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GAGTGCTCGT CGACTCATTA GGGGGAAACA TGGTTCCCCC GGGAGGCGAA        50

(2) INFORMATION FOR SEQ ID NO:5:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GAGTGCTCAA GCTTCAAAAC AAAATGGGGC TCTACCACGT CACCAATGAT TGCCCTAAC        59

(2) INFORMATION FOR SEQ ID NO:6:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GAGTGCTCGT CGACTCATTA AGGGGACCAG TTCATCATCA TATCCCATGC CAT        53

(2) INFORMATION FOR SEQ ID NO:7:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GAGTGCAGCC TTCAAAACAA AATGAGCACG AATCCTAAAC CTCAAAAAAA AAAC        54

(2) INFORMATION FOR SEQ ID NO:8:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GAGTGCTCGT CGACTCATTA ACCCAAATTG CGCGACCTAC GCCGGGGTC TGT        53

```
(2) INFORMATION FOR SEQ ID NO:9:

(i) SEQUENCE CHARACTERISTICS:
        (A) LENGTH: 9401 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 342..9374

(ix) FEATURE:
        (A) NAME/KEY: misc_feature
        (B) LOCATION: 366
        (D) OTHER INFORMATION: /note= "This amino acid position
            can also be Arg."

(ix) FEATURE:
        (A) NAME/KEY: misc_feature
        (B) LOCATION: 372
        (D) OTHER INFORMATION: /note= "This amino acid position
            can also be Thr."

(ix) FEATURE:
        (A) NAME/KEY: misc_feature
        (B) LOCATION: 867
        (D) OTHER INFORMATION: /note= "This amino acid position
            can also be Thr."

(ix) FEATURE:
        (A) NAME/KEY: misc_feature
        (B) LOCATION: 1341
        (D) OTHER INFORMATION: /note= "This amino acid position
            can also be Val."

(ix) FEATURE:
        (A) NAME/KEY: misc_feature
        (B) LOCATION: 2148
        (D) OTHER INFORMATION: /note= "This amino acid position
            can also be Ile."

(ix) FEATURE:
        (A) NAME/KEY: misc_feature
        (B) LOCATION: 2883
        (D) OTHER INFORMATION: /note= "This amino acid position
            can also be Asn."

(ix) FEATURE:
        (A) NAME/KEY: misc_feature
        (B) LOCATION: 3681
        (D) OTHER INFORMATION: /note= "This amino acid position
            can also be Ser."

(ix) FEATURE:
        (A) NAME/KEY: misc_feature
        (B) LOCATION: 3690
        (D) OTHER INFORMATION: /note= "This amino acid position
            can also be Thr."

(ix) FEATURE:
        (A) NAME/KEY: misc_feature
        (B) LOCATION: 4167
        (D) OTHER INFORMATION: /note= "This amino acid position
            can also be Leu."

(ix) FEATURE:
        (A) NAME/KEY: misc_feature
        (B) LOCATION: 4323
        (D) OTHER INFORMATION: /note= "This amino acid position
            can also be Val."

(ix) FEATURE:
        (A) NAME/KEY: misc_feature
        (B) LOCATION: 4701
        (D) OTHER INFORMATION: /note= "This amino acid position
            can also be Tyr."
```

```
(ix) FEATURE:
    (A) NAME/KEY: misc_feature
    (B) LOCATION: 4752
    (D) OTHER INFORMATION: /note= "This amino acid position
        can also be Ser."

(ix) FEATURE:
    (A) NAME/KEY: misc_feature
    (B) LOCATION: 5970
    (D) OTHER INFORMATION: /note= "This amino acid position
        can also be Gly."

(ix) FEATURE:
    (A) NAME/KEY: misc_feature
    (B) LOCATION: 6183
    (D) OTHER INFORMATION: /note= "This amino acid position
        can also be His."

(ix) FEATURE:
    (A) NAME/KEY: misc_feature
    (B) LOCATION: 6186
    (D) OTHER INFORMATION: /note= "This amino acid position
        can also be Cys."

(ix) FEATURE:
    (A) NAME/KEY: misc_feature
    (B) LOCATION: 6402
    (D) OTHER INFORMATION: /note= "This amino acid position
        can also be Val."

(ix) FEATURE:
    (A) NAME/KEY: misc_feature
    (B) LOCATION: 7386
    (D) OTHER INFORMATION: /note= "This amino acid position
        can also be Ser."

(ix) FEATURE:
    (A) NAME/KEY: misc_feature
    (B) LOCATION: 7494
    (D) OTHER INFORMATION: /note= "This amino acid position
        can also be Phe."

(ix) FEATURE:
    (A) NAME/KEY: misc_feature
    (B) LOCATION: 7497
    (D) OTHER INFORMATION: /note= "This amino acid position
        can also be Ala."

(ix) FEATURE:
    (A) NAME/KEY: misc_feature
    (B) LOCATION: 7845
    (D) OTHER INFORMATION: /note= "This amino acid position
        can also be Phe."

(ix) FEATURE:
    (A) NAME/KEY: misc_feature
    (B) LOCATION: 8409
    (D) OTHER INFORMATION: /note= "This amino acid position
        can also be Gly."

(ix) FEATURE:
    (A) NAME/KEY: misc_feature
    (B) LOCATION: 9102
    (D) OTHER INFORMATION: /note= "This amino acid position
        can also by Gly."

(ix) FEATURE:
    (A) NAME/KEY: misc_feature
    (B) LOCATION: 9327
    (D) OTHER INFORMATION: /note= "This amino acid position
        can also be Pro."

(xi) SEQUENCE DESCRIPTION: SEQ ID NO:9:

GCCAGCCCCC TGATGGGGGC GACACTCCAC CATGAATCAC TCCCCTGTGA GGAACTACTG      60

TCTTCACGCA GAAAGCGTCT AGCCATGGCG TTAGTATGAG TGTCGTGCAG CCTCCAGGAC     120
```

```
CCCCCCTCCC GGGAGAGCCA TAGTGGTCTG CGGAACCGGT GAGTACACCG GAATTGCCAG      180

GACGACCGGG TCCTTTCTTG GATCAACCCG CTCAATGCCT GGAGATTTGG GCGTGCCCCC      240

GCAAGACTGC TAGCCGAGTA GTGTTGGGTC GCGAAAGGCC TTGTGGTACT GCCTGATAGG      300

GTGCTTGCGA GTGCCCCGGG AGGTCTCGTA GACCGTGCAC C ATG AGC ACG AAT          353
                                             Met Ser Thr Asn
                                              1

CCT AAA CCT CAA AAA AAA AAC AAA CGT AAC ACC AAC CGT CGC CCA CAG        401
Pro Lys Pro Gln Lys Lys Asn Lys Arg Asn Thr Asn Arg Arg Pro Gln
 5              10                  15                  20

GAC GTC AAG TTC CCG GGT GGC GGT CAG ATC GTT GGT GGA GTT TAC TTG        449
Asp Val Lys Phe Pro Gly Gly Gly Gln Ile Val Gly Gly Val Tyr Leu
                25                  30                  35

TTG CCG CGC AGG GGC CCT AGA TTG GGT GTG CGC GCG ACG AGA AAG ACT        497
Leu Pro Arg Arg Gly Pro Arg Leu Gly Val Arg Ala Thr Arg Lys Thr
            40                  45                  50

TCC GAG CGG TCG CAA CCT CGA GGT AGA CGT CAG CCT ATC CCC AAG GCT        545
Ser Glu Arg Ser Gln Pro Arg Gly Arg Arg Gln Pro Ile Pro Lys Ala
        55                  60                  65

CGT CGG CCC GAG GGC AGG ACC TGG GCT CAG CCC GGG TAC CCT TGG CCC        593
Arg Arg Pro Glu Gly Arg Thr Trp Ala Gln Pro Gly Tyr Pro Trp Pro
    70                  75                  80

CTC TAT GGC AAT GAG GGC TGC GGG TGG GCG GGA TGG CTC CTG TCT CCC        641
Leu Tyr Gly Asn Glu Gly Cys Gly Trp Ala Gly Trp Leu Leu Ser Pro
85                  90                  95                  100

CGT GGC TCT CGG CCT AGC TGG GGC CCC ACA GAC CCC CGG CGT AGG TCG        689
Arg Gly Ser Arg Pro Ser Trp Gly Pro Thr Asp Pro Arg Arg Arg Ser
                105                 110                 115

CGC AAT TTG GGT AAG GTC ATC GAT ACC CTT ACG TGC GGC TTC GCC GAC        737
Arg Asn Leu Gly Lys Val Ile Asp Thr Leu Thr Cys Gly Phe Ala Asp
            120                 125                 130

CTC ATG GGG TAC ATA CCG CTC GTC GGC GCC CCT CTT GGA GGC GCT GCC        785
Leu Met Gly Tyr Ile Pro Leu Val Gly Ala Pro Leu Gly Gly Ala Ala
        135                 140                 145

AGG GCC CTG GCG CAT GGC GTC CGG GTT CTG GAA GAC GGC GTG AAC TAT        833
Arg Ala Leu Ala His Gly Val Arg Val Leu Glu Asp Gly Val Asn Tyr
    150                 155                 160

GCA ACA GGG AAC CTT CCT GGT TGC TCT TTC TCT ATC TTC CTT CTG GCC        881
Ala Thr Gly Asn Leu Pro Gly Cys Ser Phe Ser Ile Phe Leu Leu Ala
165                 170                 175                 180

CTG CTC TCT TGC TTG ACT GTG CCC GCT TCG GCC TAC CAA GTG CGC AAC        929
Leu Leu Ser Cys Leu Thr Val Pro Ala Ser Ala Tyr Gln Val Arg Asn
                185                 190                 195

TCC ACG GGG CTT TAC CAC GTC ACC AAT GAT TGC CCT AAC TCG AGT ATT        977
Ser Thr Gly Leu Tyr His Val Thr Asn Asp Cys Pro Asn Ser Ser Ile
            200                 205                 210

GTG TAC GAG GCG GCC GAT GCC ATC CTG CAC ACT CCG GGG TGC GTC CCT       1025
Val Tyr Glu Ala Ala Asp Ala Ile Leu His Thr Pro Gly Cys Val Pro
        215                 220                 225

TGC GTT CGT GAG GGC AAC GCC TCG AGG TGT TGG GTG GCG ATG ACC CCT       1073
Cys Val Arg Glu Gly Asn Ala Ser Arg Cys Trp Val Ala Met Thr Pro
    230                 235                 240

ACG GTG GCC ACC AGG GAT GGC AAA CTC CCC GCG ACG CAG CTT CGA CGT       1121
Thr Val Ala Thr Arg Asp Gly Lys Leu Pro Ala Thr Gln Leu Arg Arg
245                 250                 255                 260

CAC ATC GAT CTG CTT GTC GGG AGC GCC ACC CTC TGT TCG GCC CTC TAC       1169
His Ile Asp Leu Leu Val Gly Ser Ala Thr Leu Cys Ser Ala Leu Tyr
                265                 270                 275

GTG GGG GAC CTA TGC GGG TCT GTC TTT CTT GTC GGC CAA CTG TTC ACC       1217
```

```
                                                                    -continued Val Gly Asp Leu Cys Gly Ser Val Phe Leu Val Gly Gln Leu Phe Thr
            280                 285                 290

TTC TCT CCC AGG CGC CAC TGG ACG ACG CAA GGT TGC AAT TGC TCT ATC      1265
Phe Ser Pro Arg Arg His Trp Thr Thr Gln Gly Cys Asn Cys Ser Ile
        295                 300                 305

TAT CCC GGC CAT ATA ACG GGT CAC CGC ATG GCA TGG GAT ATG ATG ATG      1313
Tyr Pro Gly His Ile Thr Gly His Arg Met Ala Trp Asp Met Met Met
    310                 315                 320

AAC TGG TCC CCT ACG ACG GCG TTG GTA ATG GCT CAG CTG CTC CGG ATC      1361
Asn Trp Ser Pro Thr Thr Ala Leu Val Met Ala Gln Leu Leu Arg Ile
325                 330                 335                 340

CCA CAA GCC ATC TTG GAC ATG ATC GCT GGT GCT CAC TGG GGA GTC CTG      1409
Pro Gln Ala Ile Leu Asp Met Ile Ala Gly Ala His Trp Gly Val Leu
                345                 350                 355

GCG GGC ATA GCG TAT TTC TCC ATG GTG GGG AAC TGG GCG AAG GTC CTG      1457
Ala Gly Ile Ala Tyr Phe Ser Met Val Gly Asn Trp Ala Lys Val Leu
            360                 365                 370

GTA GTG CTG CTG CTA TTT GCC GGC GTC GAC GCG GAA ACC CAC GTC ACC      1505
Val Val Leu Leu Leu Phe Ala Gly Val Asp Ala Glu Thr His Val Thr
        375                 380                 385

GGG GGA AGT GCC GGC CAC ACT GTG TCT GGA TTT GTT AGC CTC CTC GCA      1553
Gly Gly Ser Ala Gly His Thr Val Ser Gly Phe Val Ser Leu Leu Ala
    390                 395                 400

CCA GGC GCC AAG CAG AAC GTC CAG CTG ATC AAC ACC AAC GGC AGT TGG      1601
Pro Gly Ala Lys Gln Asn Val Gln Leu Ile Asn Thr Asn Gly Ser Trp
405                 410                 415                 420

CAC CTC AAT AGC ACG GCC CTG AAC TGC AAT GAT AGC CTC AAC ACC GGC      1649
His Leu Asn Ser Thr Ala Leu Asn Cys Asn Asp Ser Leu Asn Thr Gly
                425                 430                 435

TGG TTG GCA GGG CTT TTC TAT CAC CAC AAG TTC AAC TCT TCA GGC TGT      1697
Trp Leu Ala Gly Leu Phe Tyr His His Lys Phe Asn Ser Ser Gly Cys
            440                 445                 450

CCT GAG AGG CTA GCC AGC TGC CGA CCC CTT ACC GAT TTT GAC CAG GGC      1745
Pro Glu Arg Leu Ala Ser Cys Arg Pro Leu Thr Asp Phe Asp Gln Gly
        455                 460                 465

TGG GGC CCT ATC AGT TAT GCC AAC GGA AGC GGC CCC GAC CAG CGC CCC      1793
Trp Gly Pro Ile Ser Tyr Ala Asn Gly Ser Gly Pro Asp Gln Arg Pro
    470                 475                 480

TAC TGC TGG CAC TAC CCC CCA AAA CCT TGC GGT ATT GTG CCC GCG AAG      1841
Tyr Cys Trp His Tyr Pro Pro Lys Pro Cys Gly Ile Val Pro Ala Lys
485                 490                 495                 500

AGT GTG TGT GGT CCG GTA TAT TGC TTC ACT CCC AGC CCC GTG GTG GTG      1889
Ser Val Cys Gly Pro Val Tyr Cys Phe Thr Pro Ser Pro Val Val Val
                505                 510                 515

GGA ACG ACC GAC AGG TCG GGC GCG CCC ACC TAC AGC TGG GGT GAA AAT      1937
Gly Thr Thr Asp Arg Ser Gly Ala Pro Thr Tyr Ser Trp Gly Glu Asn
            520                 525                 530

GAT ACG GAC GTC TTC GTC CTT AAC AAT ACC AGG CCA CCG CTG GGC AAT      1985
Asp Thr Asp Val Phe Val Leu Asn Asn Thr Arg Pro Pro Leu Gly Asn
        535                 540                 545

TGG TTC GGT TGT ACC TGG ATG AAC TCA ACT GGA TTC ACC AAA GTG TGC      2033
Trp Phe Gly Cys Thr Trp Met Asn Ser Thr Gly Phe Thr Lys Val Cys
    550                 555                 560

GGA GCG CCT CCT TGT GTC ATC GGA GGG GCG GGC AAC AAC ACC CTG CAC      2081
Gly Ala Pro Pro Cys Val Ile Gly Gly Ala Gly Asn Asn Thr Leu His
565                 570                 575                 580

TGC CCC ACT GAT TGC TTC CGC AAG CAT CCG GAC GCC ACA TAC TCT CGG      2129
Cys Pro Thr Asp Cys Phe Arg Lys His Pro Asp Ala Thr Tyr Ser Arg
                585                 590                 595
```

```
TGC GGC TCC GGT CCC TGG ATC ACA CCC AGG TGC CTG GTC GAC TAC CCG      2177
Cys Gly Ser Gly Pro Trp Ile Thr Pro Arg Cys Leu Val Asp Tyr Pro
            600                 605                 610

TAT AGG CTT TGG CAT TAT CCT TGT ACC ATC AAC TAC ACC ATA TTT AAA      2225
Tyr Arg Leu Trp His Tyr Pro Cys Thr Ile Asn Tyr Thr Ile Phe Lys
            615                 620                 625

ATC AGG ATG TAC GTG GGA GGG GTC GAA CAC AGG CTG GAA GCT GCC TGC      2273
Ile Arg Met Tyr Val Gly Gly Val Glu His Arg Leu Glu Ala Ala Cys
            630                 635                 640

AAC TGG ACG CGG GGC GAA CGT TGC GAT CTG GAA GAC AGG GAC AGG TCC      2321
Asn Trp Thr Arg Gly Glu Arg Cys Asp Leu Glu Asp Arg Asp Arg Ser
645                 650                 655                 660

GAG CTC AGC CCG TTA CTG CTG ACC ACT ACA CAG TGG CAG GTC CTC CCG      2369
Glu Leu Ser Pro Leu Leu Leu Thr Thr Thr Gln Trp Gln Val Leu Pro
            665                 670                 675

TGT TCC TTC ACA ACC CTA CCA GCC TTG TCC ACC GGC CTC ATC CAC CTC      2417
Cys Ser Phe Thr Thr Leu Pro Ala Leu Ser Thr Gly Leu Ile His Leu
            680                 685                 690

CAC CAG AAC ATT GTG GAC GTG CAG TAC TTG TAC GGG GTG GGG TCA AGC      2465
His Gln Asn Ile Val Asp Val Gln Tyr Leu Tyr Gly Val Gly Ser Ser
            695                 700                 705

ATC GCG TCC TGG GCC ATT AAG TGG GAG TAC GTC GTT CTC CTG TTC CTT      2513
Ile Ala Ser Trp Ala Ile Lys Trp Glu Tyr Val Val Leu Leu Phe Leu
            710                 715                 720

CTG CTT GCA GAC GCG CGC GTC TGC TCC TGC TTG TGG ATG ATG CTA CTC      2561
Leu Leu Ala Asp Ala Arg Val Cys Ser Cys Leu Trp Met Met Leu Leu
725                 730                 735                 740

ATA TCC CAA GCG GAG GCG GCT TTG GAG AAC CTC GTA ATA CTT AAT GCA      2609
Ile Ser Gln Ala Glu Ala Ala Leu Glu Asn Leu Val Ile Leu Asn Ala
            745                 750                 755

GCA TCC CTG GCC GGG ACG CAC GGT CTT GTA TCC TTC CTC GTG TTC TTC      2657
Ala Ser Leu Ala Gly Thr His Gly Leu Val Ser Phe Leu Val Phe Phe
            760                 765                 770

TGC TTT GCA TGG TAT TTG AAG GGT AAG TGG GTG CCC GGA GCG GTC TAC      2705
Cys Phe Ala Trp Tyr Leu Lys Gly Lys Trp Val Pro Gly Ala Val Tyr
            775                 780                 785

ACC TTC TAC GGG ATG TGG CCT CTC CTC CTG CTC CTG TTG GCG TTG CCC      2753
Thr Phe Tyr Gly Met Trp Pro Leu Leu Leu Leu Leu Ala Leu Pro
            790                 795                 800

CAG CGG GCG TAC GCG CTG GAC ACG GAG GTG GCC GCG TCG TGT GGC GGT      2801
Gln Arg Ala Tyr Ala Leu Asp Thr Glu Val Ala Ala Ser Cys Gly Gly
805                 810                 815                 820

GTT GTT CTC GTC GGG TTG ATG GCG CTG ACT CTG TCA CCA TAT TAC AAG      2849
Val Val Leu Val Gly Leu Met Ala Leu Thr Leu Ser Pro Tyr Tyr Lys
            825                 830                 835

CGC TAT ATC AGC TGG TGC TTG TGG TGG CTT CAG TAT TTT CTG ACC AGA      2897
Arg Tyr Ile Ser Trp Cys Leu Trp Trp Leu Gln Tyr Phe Leu Thr Arg
            840                 845                 850

GTG GAA GCG CAA CTG CAC GTG TGG ATT CCC CCC CTC AAC GTC CGA GGG      2945
Val Glu Ala Gln Leu His Val Trp Ile Pro Pro Leu Asn Val Arg Gly
            855                 860                 865

GGG CGC GAC GCC GTC ATC TTA CTC ATG TGT GCT GTA CAC CCG ACT CTG      2993
Gly Arg Asp Ala Val Ile Leu Leu Met Cys Ala Val His Pro Thr Leu
            870                 875                 880

GTA TTT GAC ATC ACC AAA TTG CTG CTG GCC GTC TTC GGA CCC CTT TGG      3041
Val Phe Asp Ile Thr Lys Leu Leu Leu Ala Val Phe Gly Pro Leu Trp
885                 890                 895                 900

ATT CTT CAA GCC AGT TTG CTT AAA GTA CCC TAC TTT GTG CGC GTC CAA      3089
Ile Leu Gln Ala Ser Leu Leu Lys Val Pro Tyr Phe Val Arg Val Gln
            905                 910                 915
```

```
GGC CTT CTC CGG TTC TGC GCG TTA GCG CGG AAG ATG ATC GGA GGC CAT    3137
Gly Leu Leu Arg Phe Cys Ala Leu Ala Arg Lys Met Ile Gly Gly His
            920                 925                 930

TAC GTG CAA ATG GTC ATC ATT AAG TTA GGG GCG CTT ACT GGC ACC TAT    3185
Tyr Val Gln Met Val Ile Ile Lys Leu Gly Ala Leu Thr Gly Thr Tyr
            935                 940                 945

GTT TAT AAC CAT CTC ACT CCT CTT CGG GAC TGG GCG CAC AAC GGC TTG    3233
Val Tyr Asn His Leu Thr Pro Leu Arg Asp Trp Ala His Asn Gly Leu
            950                 955                 960

CGA GAT CTG GCC GTG GCT GTA GAG CCA GTC GTC TTC TCC CAA ATG GAG    3281
Arg Asp Leu Ala Val Ala Val Glu Pro Val Val Phe Ser Gln Met Glu
965                 970                 975                 980

ACC AAG CTC ATC ACG TGG GGG GCA GAT ACC GCC GCG TGC GGT GAC ATC    3329
Thr Lys Leu Ile Thr Trp Gly Ala Asp Thr Ala Ala Cys Gly Asp Ile
            985                 990                 995

ATC AAC GGC TTG CCT GTT TCC GCC CGC AGG GGC CGG GAG ATA CTG CTC    3377
Ile Asn Gly Leu Pro Val Ser Ala Arg Arg Gly Arg Glu Ile Leu Leu
            1000                1005                1010

GGG CCA GCC GAT GGA ATG GTC TCC AAG GGG TGG AGG TTG CTG GCG CCC    3425
Gly Pro Ala Asp Gly Met Val Ser Lys Gly Trp Arg Leu Leu Ala Pro
            1015                1020                1025

ATC ACG GCG TAC GCC CAG CAG ACA AGG GGC CTC CTA GGG TGC ATA ATC    3473
Ile Thr Ala Tyr Ala Gln Gln Thr Arg Gly Leu Leu Gly Cys Ile Ile
            1030                1035                1040

ACC AGC CTA ACT GGC CGG GAC AAA AAC CAA GTG GAG GGT GAG GTC CAG    3521
Thr Ser Leu Thr Gly Arg Asp Lys Asn Gln Val Glu Gly Glu Val Gln
1045                1050                1055                1060

ATT GTG TCA ACT GCT GCC CAA ACC TTC CTG GCA ACG TGC ATC AAT GGG    3569
Ile Val Ser Thr Ala Ala Gln Thr Phe Leu Ala Thr Cys Ile Asn Gly
            1065                1070                1075

GTG TGC TGG ACT GTC TAC CAC GGG GCC GGA ACG AGG ACC ATC GCG TCA    3617
Val Cys Trp Thr Val Tyr His Gly Ala Gly Thr Arg Thr Ile Ala Ser
            1080                1085                1090

CCC AAG GGT CCT GTC ATC CAG ATG TAT ACC AAT GTA GAC CAA GAC CTT    3665
Pro Lys Gly Pro Val Ile Gln Met Tyr Thr Asn Val Asp Gln Asp Leu
            1095                1100                1105

GTG GGC TGG CCC GCT CCG CAA GGT AGC CGC TCA TTG ACA CCC TGC ACT    3713
Val Gly Trp Pro Ala Pro Gln Gly Ser Arg Ser Leu Thr Pro Cys Thr
            1110                1115                1120

TGC GGC TCC TCG GAC CTT TAC CTG GTC ACG AGG CAC GCC GAT GTC ATT    3761
Cys Gly Ser Ser Asp Leu Tyr Leu Val Thr Arg His Ala Asp Val Ile
1125                1130                1135                1140

CCC GTG CGC CGG CGG GGT GAT AGC AGG GGC AGC CTG CTG TCG CCC CGG    3809
Pro Val Arg Arg Arg Gly Asp Ser Arg Gly Ser Leu Leu Ser Pro Arg
            1145                1150                1155

CCC ATT TCC TAC TTG AAA GGC TCC TCG GGG GGT CCG CTG TTG TGC CCC    3857
Pro Ile Ser Tyr Leu Lys Gly Ser Ser Gly Gly Pro Leu Leu Cys Pro
            1160                1165                1170

GCG GGG CAC GCC GTG GGC ATA TTT AGG GCC GCG GTG TGC ACC CGT GGA    3905
Ala Gly His Ala Val Gly Ile Phe Arg Ala Ala Val Cys Thr Arg Gly
            1175                1180                1185

GTG GCT AAG GCG GTG GAC TTT ATC CCT GTG GAG AAC CTA GAG ACA ACC    3953
Val Ala Lys Ala Val Asp Phe Ile Pro Val Glu Asn Leu Glu Thr Thr
            1190                1195                1200

ATG AGG TCC CCG GTG TTC ACG GAT AAC TCC TCT CCA CCA GTA GTG CCC    4001
Met Arg Ser Pro Val Phe Thr Asp Asn Ser Ser Pro Pro Val Val Pro
1205                1210                1215                1220

CAG AGC TTC CAG GTG GCT CAC CTC CAT GCT CCC ACA GGC AGC GGC AAA    4049
Gln Ser Phe Gln Val Ala His Leu His Ala Pro Thr Gly Ser Gly Lys
```

-continued

```
                     1225                1230                1235
AGC ACC AAG GTC CCG GCT GCA TAT GCA GCT CAG GGC TAT AAG GTG CTA       4097
Ser Thr Lys Val Pro Ala Ala Tyr Ala Ala Gln Gly Tyr Lys Val Leu
            1240                1245                1250

GTA CTC AAC CCC TCT GTT GCT GCA ACA CTG GGC TTT GGT GCT TAC ATG       4145
Val Leu Asn Pro Ser Val Ala Ala Thr Leu Gly Phe Gly Ala Tyr Met
            1255                1260                1265

TCC AAG GCT CAT GGG ATC GAT CCT AAC ATC AGG ACC GGG GTG AGA ACA       4193
Ser Lys Ala His Gly Ile Asp Pro Asn Ile Arg Thr Gly Val Arg Thr
            1270                1275                1280

ATT ACC ACT GGC AGC CCC ATC ACG TAC TCC ACC TAC GGC AAG TTC CTT       4241
Ile Thr Thr Gly Ser Pro Ile Thr Tyr Ser Thr Tyr Gly Lys Phe Leu
1285                1290                1295                1300

GCC GAC GGC GGG TGC TCG GGG GGC GCT TAT GAC ATA ATA ATT TGT GAC       4289
Ala Asp Gly Gly Cys Ser Gly Gly Ala Tyr Asp Ile Ile Ile Cys Asp
            1305                1310                1315

GAG TGC CAC TCC ACG GAT GCC ACA TCC ATC TTG GGC ATC GGC ACT GTC       4337
Glu Cys His Ser Thr Asp Ala Thr Ser Ile Leu Gly Ile Gly Thr Val
            1320                1325                1330

CTT GAC CAA GCA GAG ACT GCG GGG GCG AGA CTG GTT GTG CTC GCC ACC       4385
Leu Asp Gln Ala Glu Thr Ala Gly Ala Arg Leu Val Val Leu Ala Thr
            1335                1340                1345

GCC ACC CCT CCG GGC TCC GTC ACT GTG CCC CAT CCC AAC ATC GAG GAG       4433
Ala Thr Pro Pro Gly Ser Val Thr Val Pro His Pro Asn Ile Glu Glu
            1350                1355                1360

GTT GCT CTG TCC ACC ACC GGA GAG ATC CCT TTT TAC GGC AAG GCT ATC       4481
Val Ala Leu Ser Thr Thr Gly Glu Ile Pro Phe Tyr Gly Lys Ala Ile
1365                1370                1375                1380

CCC CTC GAA GTA ATC AAG GGG GGG AGA CAT CTC ATC TTC TGT CAT TCA       4529
Pro Leu Glu Val Ile Lys Gly Gly Arg His Leu Ile Phe Cys His Ser
            1385                1390                1395

AAG AAG AAG TGC GAC GAA CTC GCC GCA AAG CTG GTC GCA TTG GGC ATC       4577
Lys Lys Lys Cys Asp Glu Leu Ala Ala Lys Leu Val Ala Leu Gly Ile
            1400                1405                1410

AAT GCC GTG GCC TAC TAC CGC GGT CTT GAC GTG TCC GTC ATC CCG ACC       4625
Asn Ala Val Ala Tyr Tyr Arg Gly Leu Asp Val Ser Val Ile Pro Thr
            1415                1420                1425

AGC GGC GAT GTT GTC GTC GTG GCA ACC GAT GCC CTC ATG ACC GGC TAT       4673
Ser Gly Asp Val Val Val Val Ala Thr Asp Ala Leu Met Thr Gly Tyr
            1430                1435                1440

ACC GGC GAC TTC GAC TCG GTG ATA GAC TGC AAT ACG TGT GTC ACC CAG       4721
Thr Gly Asp Phe Asp Ser Val Ile Asp Cys Asn Thr Cys Val Thr Gln
1445                1450                1455                1460

ACA GTC GAT TTC AGC CTT GAC CCT ACC TTC ACC ATT GAG ACA ATC ACG       4769
Thr Val Asp Phe Ser Leu Asp Pro Thr Phe Thr Ile Glu Thr Ile Thr
            1465                1470                1475

CTC CCC CAG GAT GCT GTC TCC CGC ACT CAA CGT CGG GGC AGG ACT GGC       4817
Leu Pro Gln Asp Ala Val Ser Arg Thr Gln Arg Arg Gly Arg Thr Gly
            1480                1485                1490

AGG GGG AAG CCA GGC ATC TAC AGA TTT GTG GCA CCG GGG GAG CGC CCC       4865
Arg Gly Lys Pro Gly Ile Tyr Arg Phe Val Ala Pro Gly Glu Arg Pro
            1495                1500                1505

TCC GGC ATG TTC GAC TCG TCC GTC CTC TGT GAG TGC TAT GAC GCA GGC       4913
Ser Gly Met Phe Asp Ser Ser Val Leu Cys Glu Cys Tyr Asp Ala Gly
            1510                1515                1520

TGT GCT TGG TAT GAG CTC ACG CCC GCC GAG ACT ACA GTT AGG CTA CGA       4961
Cys Ala Trp Tyr Glu Leu Thr Pro Ala Glu Thr Thr Val Arg Leu Arg
1525                1530                1535                1540

GCG TAC ATG AAC ACC CCG GGG CTT CCC GTG TGC CAG GAC CAT CTT GAA       5009
```

```
Ala Tyr Met Asn Thr Pro Gly Leu Pro Val Cys Gln Asp His Leu Glu
            1545                1550                1555

TTT TGG GAG GGC GTC TTT ACA GGC CTC ACT CAT ATA GAT GCC CAC TTT          5057
Phe Trp Glu Gly Val Phe Thr Gly Leu Thr His Ile Asp Ala His Phe
        1560                1565                1570

CTA TCC CAG ACA AAG CAG AGT GGG GAG AAC CTT CCT TAC CTG GTA GCG          5105
Leu Ser Gln Thr Lys Gln Ser Gly Glu Asn Leu Pro Tyr Leu Val Ala
    1575                1580                1585

TAC CAA GCC ACC GTG TGC GCT AGG GCT CAA GCC CCT CCC CCA TCG TGG          5153
Tyr Gln Ala Thr Val Cys Ala Arg Ala Gln Ala Pro Pro Pro Ser Trp
1590                1595                1600

GAC CAG ATG TGG AAG TGT TTG ATT CGC CTC AAG CCC ACC CTC CAT GGG          5201
Asp Gln Met Trp Lys Cys Leu Ile Arg Leu Lys Pro Thr Leu His Gly
1605                1610                1615                1620

CCA ACA CCC CTG CTA TAC AGA CTG GGC GCT GTT CAG AAT GAA ATC ACC          5249
Pro Thr Pro Leu Leu Tyr Arg Leu Gly Ala Val Gln Asn Glu Ile Thr
                1625                1630                1635

CTG ACG CAC CCA GTC ACC AAA TAC ATC ATG ACA TGC ATG TCG GCC GAC          5297
Leu Thr His Pro Val Thr Lys Tyr Ile Met Thr Cys Met Ser Ala Asp
            1640                1645                1650

CTG GAG GTC GTC ACG AGC ACC TGG GTG CTC GTT GGC GGC GTC CTG GCT          5345
Leu Glu Val Val Thr Ser Thr Trp Val Leu Val Gly Gly Val Leu Ala
        1655                1660                1665

GCT TTG GCC GCG TAT TGC CTG TCA ACA GGC TGC GTG GTC ATA GTG GGC          5393
Ala Leu Ala Ala Tyr Cys Leu Ser Thr Gly Cys Val Val Ile Val Gly
    1670                1675                1680

AGG GTC GTC TTG TCC GGG AAG CCG GCA ATC ATA CCT GAC AGG GAA GTC          5441
Arg Val Val Leu Ser Gly Lys Pro Ala Ile Ile Pro Asp Arg Glu Val
1685                1690                1695                1700

CTC TAC CGA GAG TTC GAT GAG ATG GAA GAG TGC TCT CAG CAC TTA CCG          5489
Leu Tyr Arg Glu Phe Asp Glu Met Glu Glu Cys Ser Gln His Leu Pro
                1705                1710                1715

TAC ATC GAG CAA GGG ATG ATG CTC GCC GAG CAG TTC AAG CAG AAG GCC          5537
Tyr Ile Glu Gln Gly Met Met Leu Ala Glu Gln Phe Lys Gln Lys Ala
            1720                1725                1730

CTC GGC CTC CTG CAG ACC GCG TCC CGT CAG GCA GAG GTT ATC GCC CCT          5585
Leu Gly Leu Leu Gln Thr Ala Ser Arg Gln Ala Glu Val Ile Ala Pro
        1735                1740                1745

GCT GTC CAG ACC AAC TGG CAA AAA CTC GAG ACC TTC TGG GCG AAG CAT          5633
Ala Val Gln Thr Asn Trp Gln Lys Leu Glu Thr Phe Trp Ala Lys His
    1750                1755                1760

ATG TGG AAC TTC ATC AGT GGG ATA CAA TAC TTG GCG GGC TTG TCA ACG          5681
Met Trp Asn Phe Ile Ser Gly Ile Gln Tyr Leu Ala Gly Leu Ser Thr
1765                1770                1775                1780

CTG CCT GGT AAC CCC GCC ATT GCT TCA TTG ATG GCT TTT ACA GCT GCT          5729
Leu Pro Gly Asn Pro Ala Ile Ala Ser Leu Met Ala Phe Thr Ala Ala
                1785                1790                1795

GTC ACC AGC CCA CTA ACC ACT AGC CAA ACC CTC CTC TTC AAC ATA TTG          5777
Val Thr Ser Pro Leu Thr Thr Ser Gln Thr Leu Leu Phe Asn Ile Leu
            1800                1805                1810

GGG GGG TGG GTG GCT GCC CAG CTC GCC GCC CCC GGT GCC GCT ACT GCC          5825
Gly Gly Trp Val Ala Ala Gln Leu Ala Ala Pro Gly Ala Ala Thr Ala
        1815                1820                1825

TTT GTG GGC GCT GGC TTA GCT GGC GCC GCC ATC GGC AGT GTT GGA CTG          5873
Phe Val Gly Ala Gly Leu Ala Gly Ala Ala Ile Gly Ser Val Gly Leu
    1830                1835                1840

GGG AAG GTC CTC ATA GAC ATC CTT GCA GGG TAT GGC GCG GGC GTG GCG          5921
Gly Lys Val Leu Ile Asp Ile Leu Ala Gly Tyr Gly Ala Gly Val Ala
1845                1850                1855                1860
```

```
                                                     -continued

GGA GCT CTT GTG GCA TTC AAG ATC ATG AGC GGT GAG GTC CCC TCC ACG      5969
Gly Ala Leu Val Ala Phe Lys Ile Met Ser Gly Glu Val Pro Ser Thr
                1865                1870                1875

GAG GAC CTG GTC AAT CTA CTG CCC GCC ATC CTC TCG CCC GGA GCC CTC      6017
Glu Asp Leu Val Asn Leu Leu Pro Ala Ile Leu Ser Pro Gly Ala Leu
            1880                1885                1890

GTA GTC GGC GTG GTC TGT GCA GCA ATA CTG CGC GGC CAC GTT GGC CCG      6065
Val Val Gly Val Val Cys Ala Ala Ile Leu Arg Arg His Val Gly Pro
        1895                1900                1905

GGC GAG GGG GCA GTG CAG TGG ATG AAC CGG CTG ATA GCC TTC GCC TCC      6113
Gly Glu Gly Ala Val Gln Trp Met Asn Arg Leu Ile Ala Phe Ala Ser
    1910                1915                1920

CGG GGG AAC CAT GTT TCC CCC ACG CAC TAC GTG CCG GAG AGC GAT GCA      6161
Arg Gly Asn His Val Ser Pro Thr His Tyr Val Pro Glu Ser Asp Ala
1925                1930                1935                1940

GCT GCC CGC GTC ACT GCC ATA CTC AGC AGC CTC ACT GTA ACC CAG CTC      6209
Ala Ala Arg Val Thr Ala Ile Leu Ser Ser Leu Thr Val Thr Gln Leu
                1945                1950                1955

CTG AGG CGA CTG CAC CAG TGG ATA AGC TCG GAG TGT ACC ACT CCA TGC      6257
Leu Arg Arg Leu His Gln Trp Ile Ser Ser Glu Cys Thr Thr Pro Cys
            1960                1965                1970

TCC GGT TCC TGG CTA AGG GAC ATC TGG GAC TGG ATA TGC GAG GTG TTG      6305
Ser Gly Ser Trp Leu Arg Asp Ile Trp Asp Trp Ile Cys Glu Val Leu
        1975                1980                1985

AGC GAC TTT AAG ACC TGG CTA AAA GCT AAG CTC ATG CCA CAG CTG CCT      6353
Ser Asp Phe Lys Thr Trp Leu Lys Ala Lys Leu Met Pro Gln Leu Pro
    1990                1995                2000

GGG ATC CCC TTT GTG TCC TGC CAG CGC GGG TAT AAG GGG GTC TGG CGA      6401
Gly Ile Pro Phe Val Ser Cys Gln Arg Gly Tyr Lys Gly Val Trp Arg
2005                2010                2015                2020

GTG GAC GGC ATC ATG CAC ACT CGC TGC CAC TGT GGA GCT GAG ATC ACT      6449
Val Asp Gly Ile Met His Thr Arg Cys His Cys Gly Ala Glu Ile Thr
                2025                2030                2035

GGA CAT GTC AAA AAC GGG ACG ATG AGG ATC GTC GGT CCT AGG ACC TGC      6497
Gly His Val Lys Asn Gly Thr Met Arg Ile Val Gly Pro Arg Thr Cys
            2040                2045                2050

AGG AAC ATG TGG AGT GGG ACC TTC CCC ATT AAT GCC TAC ACC ACG GGC      6545
Arg Asn Met Trp Ser Gly Thr Phe Pro Ile Asn Ala Tyr Thr Thr Gly
        2055                2060                2065

CCC TGT ACC CCC CTT CCT GCG CCG AAC TAC ACG TTC GCG CTA TGG AGG      6593
Pro Cys Thr Pro Leu Pro Ala Pro Asn Tyr Thr Phe Ala Leu Trp Arg
    2070                2075                2080

GTG TCT GCA GAG GAA TAT GTG GAG ATA AGG CAG GTG GGG GAC TTC CAC      6641
Val Ser Ala Glu Glu Tyr Val Glu Ile Arg Gln Val Gly Asp Phe His
2085                2090                2095                2100

TAC GTG ACG GGT ATG ACT ACT GAC AAT CTC AAA TGC CCG TGC CAG GTC      6689
Tyr Val Thr Gly Met Thr Thr Asp Asn Leu Lys Cys Pro Cys Gln Val
                2105                2110                2115

CCA TCG CCC GAA TTT TTC ACA GAA TTG GAC GGG GTG CGC CTA CAT AGG      6737
Pro Ser Pro Glu Phe Phe Thr Glu Leu Asp Gly Val Arg Leu His Arg
            2120                2125                2130

TTT GCG CCC CCC TGC AAG CCC TTG CTG CGG GAG GAG GTA TCA TTC AGA      6785
Phe Ala Pro Pro Cys Lys Pro Leu Leu Arg Glu Glu Val Ser Phe Arg
        2135                2140                2145

GTA GGA CTC CAC GAA TAC CCG GTA GGG TCG CAA TTA CCT TGC GAG CCC      6833
Val Gly Leu His Glu Tyr Pro Val Gly Ser Gln Leu Pro Cys Glu Pro
    2150                2155                2160

GAA CCG GAC GTG GCC GTG TTG ACG TCC ATG CTC ACT GAT CCC TCC CAT      6881
Glu Pro Asp Val Ala Val Leu Thr Ser Met Leu Thr Asp Pro Ser His
2165                2170                2175                2180
```

```
ATA ACA GCA GAG GCG GCC GGG CGA AGG TTG GCG AGG GGA TCA CCC CCC      6929
Ile Thr Ala Glu Ala Ala Gly Arg Arg Leu Ala Arg Gly Ser Pro Pro
                2185                2190                2195

TCT GTG GCC AGC TCC TCG GCT AGC CAG CTA TCC GCT CCA TCT CTC AAG      6977
Ser Val Ala Ser Ser Ala Ser Gln Leu Ser Ala Pro Ser Leu Lys
                2200                2205                2210

GCA ACT TGC ACC GCT AAC CAT GAC TCC CCT GAT GCT GAG CTC ATA GAG      7025
Ala Thr Cys Thr Ala Asn His Asp Ser Pro Asp Ala Glu Leu Ile Glu
                2215                2220                2225

GCC AAC CTC CTA TGG AGG CAG GAG ATG GGC GGC AAC ATC ACC AGG GTT      7073
Ala Asn Leu Leu Trp Arg Gln Glu Met Gly Gly Asn Ile Thr Arg Val
                2230                2235                2240

GAG TCA GAA AAC AAA GTG GTG ATT CTG GAC TCC TTC GAT CCG CTT GTG      7121
Glu Ser Glu Asn Lys Val Val Ile Leu Asp Ser Phe Asp Pro Leu Val
2245                2250                2255                2260

GCG GAG GAG GAC GAG CGG GAG ATC TCC GTA CCC GCA GAA ATC CTG CGG      7169
Ala Glu Glu Asp Glu Arg Glu Ile Ser Val Pro Ala Glu Ile Leu Arg
                2265                2270                2275

AAG TCT CGG AGA TTC GCC CAG GCC CTG CCC GTT TGG GCG CGG CCG GAC      7217
Lys Ser Arg Arg Phe Ala Gln Ala Leu Pro Val Trp Ala Arg Pro Asp
                2280                2285                2290

TAT AAC CCC CCG CTA GTG GAG ACG TGG AAA AAG CCC GAC TAC GAA CCA      7265
Tyr Asn Pro Pro Leu Val Glu Thr Trp Lys Lys Pro Asp Tyr Glu Pro
                2295                2300                2305

CCT GTG GTC CAT GGC TGT CCG CTT CCA CCT CCA AAG TCC CCT CCT GTG      7313
Pro Val Val His Gly Cys Pro Leu Pro Pro Pro Lys Ser Pro Pro Val
                2310                2315                2320

CCT CCG CCT CGG AAG AAG CGG ACG GTG GTC CTC ACT GAA TCA ACC CTA      7361
Pro Pro Pro Arg Lys Lys Arg Thr Val Val Leu Thr Glu Ser Thr Leu
2325                2330                2335                2340

TCT ACT GCC TTG GCC GAG CTC GCC ACC AGA AGC TTT GGC AGC TCC TCA      7409
Ser Thr Ala Leu Ala Glu Leu Ala Thr Arg Ser Phe Gly Ser Ser Ser
                2345                2350                2355

ACT TCC GGC ATT ACG GGC GAC AAT ACG ACA ACA TCC TCT GAG CCC GCC      7457
Thr Ser Gly Ile Thr Gly Asp Asn Thr Thr Thr Ser Ser Glu Pro Ala
                2360                2365                2370

CCT TCT GGC TGC CCC CCC GAC TCC GAC GCT GAG TCC TAT TCC TCC ATG      7505
Pro Ser Gly Cys Pro Pro Asp Ser Asp Ala Glu Ser Tyr Ser Ser Met
                2375                2380                2385

CCC CCC CTG GAG GGG GAG CCT GGG GAT CCG GAT CTT AGC GAC GGG TCA      7553
Pro Pro Leu Glu Gly Glu Pro Gly Asp Pro Asp Leu Ser Asp Gly Ser
                2390                2395                2400

TGG TCA ACG GTC AGT AGT GAG GCC AAC GCG GAG GAT GTC GTG TGC TGC      7601
Trp Ser Thr Val Ser Ser Glu Ala Asn Ala Glu Asp Val Val Cys Cys
2405                2410                2415                2420

TCA ATG TCT TAC TCT TGG ACA GGC GCA CTC GTC ACC CCG TGC GCC GCG      7649
Ser Met Ser Tyr Ser Trp Thr Gly Ala Leu Val Thr Pro Cys Ala Ala
                2425                2430                2435

GAA GAA CAG AAA CTG CCC ATC AAT GCA CTA AGC AAC TCG TTG CTA CGT      7697
Glu Glu Gln Lys Leu Pro Ile Asn Ala Leu Ser Asn Ser Leu Leu Arg
                2440                2445                2450

CAC CAC AAT TTG GTG TAT TCC ACC ACC TCA CGC AGT GCT TGC CAA AGG      7745
His His Asn Leu Val Tyr Ser Thr Thr Ser Arg Ser Ala Cys Gln Arg
                2455                2460                2465

CAG AAG AAA GTC ACA TTT GAC AGA CTG CAA GTT CTG GAC AGC CAT TAC      7793
Gln Lys Lys Val Thr Phe Asp Arg Leu Gln Val Leu Asp Ser His Tyr
                2470                2475                2480

CAG GAC GTA CTC AAG GAG GTT AAA GCA GCG GCG TCA AAA GTG AAG GCT      7841
Gln Asp Val Leu Lys Glu Val Lys Ala Ala Ala Ser Lys Val Lys Ala
```

-continued

```
   2485              2490                2495                 2500
AAC TTG CTA TCC GTA GAG GAA GCT TGC AGC CTG ACG CCA CAC TCA      7889
Asn Leu Leu Ser Val Glu Glu Ala Cys Ser Leu Thr Pro Pro His Ser
             2505              2510              2515

GCC AAA TCC AAG TTT GGT TAT GGG GCA AAA GAC GTC CGT TGC CAT GCC  7937
Ala Lys Ser Lys Phe Gly Tyr Gly Ala Lys Asp Val Arg Cys His Ala
             2520              2525              2530

AGA AAG GCC GTA ACC CAC ATC AAC TCC GTG TGG AAA GAC CTT CTG GAA  7985
Arg Lys Ala Val Thr His Ile Asn Ser Val Trp Lys Asp Leu Leu Glu
             2535              2540              2545

GAC AAT GTA ACA CCA ATA GAC ACT ACC ATC ATG GCT AAG AAC GAG GTT  8033
Asp Asn Val Thr Pro Ile Asp Thr Thr Ile Met Ala Lys Asn Glu Val
             2550              2555              2560

TTC TGC GTT CAG CCT GAG AAG GGG GGT CGT AAG CCA GCT CGT CTC ATC  8081
Phe Cys Val Gln Pro Glu Lys Gly Gly Arg Lys Pro Ala Arg Leu Ile
2565              2570              2575              2580

GTG TTC CCC GAT CTG GGC GTG CGC GTG TGC GAA AAG ATG GCT TTG TAC  8129
Val Phe Pro Asp Leu Gly Val Arg Val Cys Glu Lys Met Ala Leu Tyr
             2585              2590              2595

GAC GTG GTT ACA AAG CTC CCC TTG GCC GTG ATG GGA AGC TCC TAC GGA  8177
Asp Val Val Thr Lys Leu Pro Leu Ala Val Met Gly Ser Ser Tyr Gly
             2600              2605              2610

TTC CAA TAC TCA CCA GGA CAG CGG GTT GAA TTC CTC GTG CAA GCG TGG  8225
Phe Gln Tyr Ser Pro Gly Gln Arg Val Glu Phe Leu Val Gln Ala Trp
             2615              2620              2625

AAG TCC AAG AAA ACC CCA ATG GGG TTC TCG TAT GAT ACC CGC TGC TTT  8273
Lys Ser Lys Lys Thr Pro Met Gly Phe Ser Tyr Asp Thr Arg Cys Phe
             2630              2635              2640

GAC TCC ACA GTC ACT GAG AGC GAC ATC CGT ACG GAG GAG GCA ATC TAC  8321
Asp Ser Thr Val Thr Glu Ser Asp Ile Arg Thr Glu Glu Ala Ile Tyr
2645              2650              2655              2660

CAA TGT TGT GAC CTC GAC CCC CAA GCC CGC GTG GCC ATC AAG TCC CTC  8369
Gln Cys Cys Asp Leu Asp Pro Gln Ala Arg Val Ala Ile Lys Ser Leu
             2665              2670              2675

ACC GAG AGG CTT TAT GTT GGG GGC CCT CTT ACC AAT TCA AGG GGG GAG  8417
Thr Glu Arg Leu Tyr Val Gly Gly Pro Leu Thr Asn Ser Arg Gly Glu
             2680              2685              2690

AAC TGC GGC TAT CGC AGG TGC CGC GCG AGC GGC GTA CTG ACA ACT AGC  8465
Asn Cys Gly Tyr Arg Arg Cys Arg Ala Ser Gly Val Leu Thr Thr Ser
             2695              2700              2705

TGT GGT AAC ACC CTC ACT TGC TAC ATC AAG GCC CGG GCA GCC TGT CGA  8513
Cys Gly Asn Thr Leu Thr Cys Tyr Ile Lys Ala Arg Ala Ala Cys Arg
             2710              2715              2720

GCC GCA GGG CTC CAG GAC TGC ACC ATG CTC GTG TGT GGC GAC GAC TTA  8561
Ala Ala Gly Leu Gln Asp Cys Thr Met Leu Val Cys Gly Asp Asp Leu
2725              2730              2735              2740

GTC GTT ATC TGT GAA AGC GCG GGG GTC CAG GAG GAC GCG GCG AGC CTG  8609
Val Val Ile Cys Glu Ser Ala Gly Val Gln Glu Asp Ala Ala Ser Leu
             2745              2750              2755

AGA GCC TTC ACG GAG GCT ATG ACC AGG TAC TCC GCC CCC CCT GGG GAC  8657
Arg Ala Phe Thr Glu Ala Met Thr Arg Tyr Ser Ala Pro Pro Gly Asp
             2760              2765              2770

CCC CCA CAA CCA GAA TAC GAC TTG GAG CTC ATA ACA TCA TGC TCC TCC  8705
Pro Pro Gln Pro Glu Tyr Asp Leu Glu Leu Ile Thr Ser Cys Ser Ser
             2775              2780              2785

AAC GTG TCA GTC GCC CAC GAC GGC GCT GGA AAG AGG GTC TAC TAC CTC  8753
Asn Val Ser Val Ala His Asp Gly Ala Gly Lys Arg Val Tyr Tyr Leu
             2790              2795              2800

ACC CGT GAC CCT ACA ACC CCC CTC GCG AGA GCT GCG TGG GAG ACA GCA  8801
```

```
                                         -continued

Thr Arg Asp Pro Thr Thr Pro Leu Ala Arg Ala Ala Trp Glu Thr Ala
2805                2810                2815                2820

AGA CAC ACT CCA GTC AAT TCC TGG CTA GGC AAC ATA ATC ATG TTT GCC      8849
Arg His Thr Pro Val Asn Ser Trp Leu Gly Asn Ile Ile Met Phe Ala
                    2825                2830                2835

CCC ACA CTG TGG GCG AGG ATG ATA CTG ATG ACC CAT TTC TTT AGC GTC      8897
Pro Thr Leu Trp Ala Arg Met Ile Leu Met Thr His Phe Phe Ser Val
                2840                2845                2850

CTT ATA GCC AGG GAC CAG CTT GAA CAG GCC CTC GAT TGC GAG ATC TAC      8945
Leu Ile Ala Arg Asp Gln Leu Glu Gln Ala Leu Asp Cys Glu Ile Tyr
            2855                2860                2865

GGG GCC TGC TAC TCC ATA GAA CCA CTT GAT CTA CCT CCA ATC ATT CAA      8993
Gly Ala Cys Tyr Ser Ile Glu Pro Leu Asp Leu Pro Pro Ile Ile Gln
        2870                2875                2880

AGA CTC CAT GGC CTC AGC GCA TTT TCA CTC CAC AGT TAC TCT CCA GGT      9041
Arg Leu His Gly Leu Ser Ala Phe Ser Leu His Ser Tyr Ser Pro Gly
2885                2890                2895                2900

GAA ATT AAT AGG GTG GCC GCA TGC CTC AGA AAA CTT GGG GTA CCG CCC      9089
Glu Ile Asn Arg Val Ala Ala Cys Leu Arg Lys Leu Gly Val Pro Pro
                    2905                2910                2915

TTG CGA GCT TGG AGA CAC CGG GCC CGG AGC GTC CGC GCT AGG CTT CTG      9137
Leu Arg Ala Trp Arg His Arg Ala Arg Ser Val Arg Ala Arg Leu Leu
                2920                2925                2930

GCC AGA GGA GGC AGG GCT GCC ATA TGT GGC AAG TAC CTC TTC AAC TGG      9185
Ala Arg Gly Gly Arg Ala Ala Ile Cys Gly Lys Tyr Leu Phe Asn Trp
            2935                2940                2945

GCA GTA AGA ACA AAG CTC AAA CTC ACT CCA ATA GCG GCC GCT GGC CAG      9233
Ala Val Arg Thr Lys Leu Lys Leu Thr Pro Ile Ala Ala Ala Gly Gln
        2950                2955                2960

CTG GAC TTG TCC GGC TGG TTC ACG GCT GGC TAC AGC GGG GGA GAC ATT      9281
Leu Asp Leu Ser Gly Trp Phe Thr Ala Gly Tyr Ser Gly Gly Asp Ile
2965                2970                2975                2980

TAT CAC AGC GTG TCT CAT GCC CGG CCC CGC TGG ATC TGG TTT TGC CTA      9329
Tyr His Ser Val Ser His Ala Arg Pro Arg Trp Ile Trp Phe Cys Leu
                    2985                2990                2995

CTC CTG CTT GCT GCA GGG GTA GGC ATC TAC CTC CTC CCC AAC CGA          9374
Leu Leu Leu Ala Ala Gly Val Gly Ile Tyr Leu Leu Pro Asn Arg
                3000                3005                3010

TGAAGGTTGG GGTAAACACT CCGGCCT                                        9401

(2) INFORMATION FOR SEQ ID NO:10:

(i) SEQUENCE CHARACTERISTICS:
        (A) LENGTH: 3011 amino acids
        (B) TYPE: amino acid
        (D) TOPOLOGY: linear (ii) MOLECULE TYPE: protein (xi) SEQUENCE DESCRIPTION: SEQ ID NO:10:

Met Ser Thr Asn Pro Lys Pro Gln Lys Lys Asn Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80
```

```
Tyr Pro Trp Pro Leu Tyr Gly Asn Glu Gly Cys Gly Trp Ala Gly Trp
                85                  90                  95
Leu Leu Ser Pro Arg Gly Ser Arg Pro Ser Trp Gly Pro Thr Asp Pro
            100                 105                 110
Arg Arg Arg Ser Arg Asn Leu Gly Lys Val Ile Asp Thr Leu Thr Cys
        115                 120                 125
Gly Phe Ala Asp Leu Met Gly Tyr Ile Pro Leu Val Gly Ala Pro Leu
    130                 135                 140
Gly Gly Ala Ala Arg Ala Leu Ala His Gly Val Arg Val Leu Glu Asp
145                 150                 155                 160
Gly Val Asn Tyr Ala Thr Gly Asn Leu Pro Gly Cys Ser Phe Ser Ile
            165                 170                 175
Phe Leu Leu Ala Leu Leu Ser Cys Leu Thr Val Pro Ala Ser Ala Tyr
        180                 185                 190
Gln Val Arg Asn Ser Thr Gly Leu Tyr His Val Thr Asn Asp Cys Pro
    195                 200                 205
Asn Ser Ser Ile Val Tyr Glu Ala Ala Asp Ala Ile Leu His Thr Pro
    210                 215                 220
Gly Cys Val Pro Cys Val Arg Glu Gly Asn Ala Ser Arg Cys Trp Val
225                 230                 235                 240
Ala Met Thr Pro Thr Val Ala Thr Arg Asp Gly Lys Leu Pro Ala Thr
            245                 250                 255
Gln Leu Arg Arg His Ile Asp Leu Leu Val Gly Ser Ala Thr Leu Cys
        260                 265                 270
Ser Ala Leu Tyr Val Gly Asp Leu Cys Gly Ser Val Phe Leu Val Gly
    275                 280                 285
Gln Leu Phe Thr Phe Ser Pro Arg Arg His Trp Thr Thr Gln Gly Cys
    290                 295                 300
Asn Cys Ser Ile Tyr Pro Gly His Ile Thr Gly His Arg Met Ala Trp
305                 310                 315                 320
Asp Met Met Met Asn Trp Ser Pro Thr Thr Ala Leu Val Met Ala Gln
            325                 330                 335
Leu Leu Arg Ile Pro Gln Ala Ile Leu Asp Met Ile Ala Gly Ala His
        340                 345                 350
Trp Gly Val Leu Ala Gly Ile Ala Tyr Phe Ser Met Val Gly Asn Trp
    355                 360                 365
Ala Lys Val Leu Val Leu Leu Leu Phe Ala Gly Val Asp Ala Glu
    370                 375                 380
Thr His Val Thr Gly Gly Ser Ala Gly His Thr Val Ser Gly Phe Val
385                 390                 395                 400
Ser Leu Leu Ala Pro Gly Ala Lys Gln Asn Val Gln Leu Ile Asn Thr
            405                 410                 415
Asn Gly Ser Trp His Leu Asn Ser Thr Ala Leu Asn Cys Asn Asp Ser
        420                 425                 430
Leu Asn Thr Gly Trp Leu Ala Gly Leu Phe Tyr His His Lys Phe Asn
    435                 440                 445
Ser Ser Gly Cys Pro Glu Arg Leu Ala Ser Cys Arg Pro Leu Thr Asp
    450                 455                 460
Phe Asp Gln Gly Trp Gly Pro Ile Ser Tyr Ala Asn Gly Ser Gly Pro
465                 470                 475                 480
Asp Gln Arg Pro Tyr Cys Trp His Tyr Pro Pro Lys Pro Cys Gly Ile
            485                 490                 495
```

```
Val Pro Ala Lys Ser Val Cys Gly Pro Val Tyr Cys Phe Thr Pro Ser
            500                 505                 510
Pro Val Val Gly Thr Thr Asp Arg Ser Gly Ala Pro Thr Tyr Ser
        515                 520                 525
Trp Gly Glu Asn Asp Thr Asp Val Phe Val Leu Asn Asn Thr Arg Pro
            530                 535                 540
Pro Leu Gly Asn Trp Phe Gly Cys Thr Trp Met Asn Ser Thr Gly Phe
545                 550                 555                 560
Thr Lys Val Cys Gly Ala Pro Pro Cys Val Ile Gly Gly Ala Gly Asn
                565                 570                 575
Asn Thr Leu His Cys Pro Thr Asp Cys Phe Arg Lys His Pro Asp Ala
                580                 585                 590
Thr Tyr Ser Arg Cys Gly Ser Gly Pro Trp Ile Thr Pro Arg Cys Leu
                595                 600                 605
Val Asp Tyr Pro Tyr Arg Leu Trp His Tyr Pro Cys Thr Ile Asn Tyr
            610                 615                 620
Thr Ile Phe Lys Ile Arg Met Tyr Val Gly Gly Val Glu His Arg Leu
625                 630                 635                 640
Glu Ala Ala Cys Asn Trp Thr Arg Gly Glu Arg Cys Asp Leu Glu Asp
                645                 650                 655
Arg Asp Arg Ser Glu Leu Ser Pro Leu Leu Leu Thr Thr Thr Gln Trp
            660                 665                 670
Gln Val Leu Pro Cys Ser Phe Thr Thr Leu Pro Ala Leu Ser Thr Gly
            675                 680                 685
Leu Ile His Leu His Gln Asn Ile Val Asp Val Gln Tyr Leu Tyr Gly
            690                 695                 700
Val Gly Ser Ser Ile Ala Ser Trp Ala Ile Lys Trp Glu Tyr Val Val
705                 710                 715                 720
Leu Leu Phe Leu Leu Leu Ala Asp Ala Arg Val Cys Ser Cys Leu Trp
                725                 730                 735
Met Met Leu Leu Ile Ser Gln Ala Glu Ala Ala Leu Glu Asn Leu Val
            740                 745                 750
Ile Leu Asn Ala Ala Ser Leu Ala Gly Thr His Gly Leu Val Ser Phe
            755                 760                 765
Leu Val Phe Phe Cys Phe Ala Trp Tyr Leu Lys Gly Lys Trp Val Pro
            770                 775                 780
Gly Ala Val Tyr Thr Phe Tyr Gly Met Trp Pro Leu Leu Leu Leu
785                 790                 795                 800
Leu Ala Leu Pro Gln Arg Ala Tyr Ala Leu Asp Thr Glu Val Ala Ala
                805                 810                 815
Ser Cys Gly Gly Val Val Leu Val Gly Leu Met Ala Leu Thr Leu Ser
                820                 825                 830
Pro Tyr Tyr Lys Arg Tyr Ile Ser Trp Cys Leu Trp Trp Leu Gln Tyr
            835                 840                 845
Phe Leu Thr Arg Val Glu Ala Gln Leu His Val Trp Ile Pro Pro Leu
            850                 855                 860
Asn Val Arg Gly Gly Arg Asp Ala Val Ile Leu Leu Met Cys Ala Val
865                 870                 875                 880
His Pro Thr Leu Val Phe Asp Ile Thr Lys Leu Leu Leu Ala Val Phe
                885                 890                 895
Gly Pro Leu Trp Ile Leu Gln Ala Ser Leu Leu Lys Val Pro Tyr Phe
            900                 905                 910
Val Arg Val Gln Gly Leu Leu Arg Phe Cys Ala Leu Ala Arg Lys Met
```

-continued

```
            915                 920                 925
Ile Gly Gly His Tyr Val Gln Met Val Ile Lys Leu Gly Ala Leu
            930                 935                 940
Thr Gly Thr Tyr Val Tyr Asn His Leu Thr Pro Leu Arg Asp Trp Ala
945                 950                 955                 960
His Asn Gly Leu Arg Asp Leu Ala Val Ala Val Glu Pro Val Phe
                965                 970                 975
Ser Gln Met Glu Thr Lys Leu Ile Thr Trp Gly Ala Asp Thr Ala Ala
                980                 985                 990
Cys Gly Asp Ile Ile Asn Gly Leu Pro Val Ser Ala Arg Arg Gly Arg
                995                 1000                1005
Glu Ile Leu Leu Gly Pro Ala Asp Gly Met Val Ser Lys Gly Trp Arg
    1010                1015                1020
Leu Leu Ala Pro Ile Thr Ala Tyr Ala Gln Gln Thr Arg Gly Leu Leu
1025                1030                1035                1040
Gly Cys Ile Ile Thr Ser Leu Thr Gly Arg Asp Lys Asn Gln Val Glu
                1045                1050                1055
Gly Glu Val Gln Ile Val Ser Thr Ala Ala Gln Thr Phe Leu Ala Thr
                1060                1065                1070
Cys Ile Asn Gly Val Cys Trp Thr Val Tyr His Gly Ala Gly Thr Arg
                1075                1080                1085
Thr Ile Ala Ser Pro Lys Gly Pro Val Ile Gln Met Tyr Thr Asn Val
                1090                1095                1100
Asp Gln Asp Leu Val Gly Trp Pro Ala Pro Gln Gly Ser Arg Ser Leu
1105                1110                1115                1120
Thr Pro Cys Thr Cys Gly Ser Ser Asp Leu Tyr Leu Val Thr Arg His
                1125                1130                1135
Ala Asp Val Ile Pro Val Arg Arg Arg Gly Asp Ser Arg Gly Ser Leu
                1140                1145                1150
Leu Ser Pro Arg Pro Ile Ser Tyr Leu Lys Gly Ser Ser Gly Gly Pro
                1155                1160                1165
Leu Leu Cys Pro Ala Gly His Ala Val Gly Ile Phe Arg Ala Ala Val
                1170                1175                1180
Cys Thr Arg Gly Val Ala Lys Ala Val Asp Phe Ile Pro Val Glu Asn
1185                1190                1195                1200
Leu Glu Thr Thr Met Arg Ser Pro Val Phe Thr Asp Asn Ser Ser Pro
                1205                1210                1215
Pro Val Val Pro Gln Ser Phe Gln Val Ala His Leu His Ala Pro Thr
                1220                1225                1230
Gly Ser Gly Lys Ser Thr Lys Val Pro Ala Ala Tyr Ala Ala Gln Gly
                1235                1240                1245
Tyr Lys Val Leu Val Leu Asn Pro Ser Val Ala Ala Thr Leu Gly Phe
                1250                1255                1260
Gly Ala Tyr Met Ser Lys Ala His Gly Ile Asp Pro Asn Ile Arg Thr
1265                1270                1275                1280
Gly Val Arg Thr Ile Thr Thr Gly Ser Pro Ile Thr Tyr Ser Thr Tyr
                1285                1290                1295
Gly Lys Phe Leu Ala Asp Gly Gly Cys Ser Gly Gly Ala Tyr Asp Ile
                1300                1305                1310
Ile Ile Cys Asp Glu Cys His Ser Thr Asp Ala Thr Ser Ile Leu Gly
                1315                1320                1325
Ile Gly Thr Val Leu Asp Gln Ala Glu Thr Ala Gly Ala Arg Leu Val
                1330                1335                1340
```

-continued

```
Val Leu Ala Thr Ala Thr Pro Pro Gly Ser Val Thr Val Pro His Pro
1345                1350                1355                1360

Asn Ile Glu Glu Val Ala Leu Ser Thr Thr Gly Glu Ile Pro Phe Tyr
            1365                1370                1375

Gly Lys Ala Ile Pro Leu Glu Val Ile Lys Gly Gly Arg His Leu Ile
            1380                1385                1390

Phe Cys His Ser Lys Lys Lys Cys Asp Glu Leu Ala Ala Lys Leu Val
            1395                1400                1405

Ala Leu Gly Ile Asn Ala Val Ala Tyr Tyr Arg Gly Leu Asp Val Ser
        1410                1415                1420

Val Ile Pro Thr Ser Gly Asp Val Val Val Ala Thr Asp Ala Leu
1425                1430                1435                1440

Met Thr Gly Tyr Thr Gly Asp Phe Asp Ser Val Ile Asp Cys Asn Thr
            1445                1450                1455

Cys Val Thr Gln Thr Val Asp Phe Ser Leu Asp Pro Thr Phe Thr Ile
            1460                1465                1470

Glu Thr Ile Thr Leu Pro Gln Asp Ala Val Ser Arg Thr Gln Arg Arg
            1475                1480                1485

Gly Arg Thr Gly Arg Gly Lys Pro Gly Ile Tyr Arg Phe Val Ala Pro
        1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
            1525                1530                1535

Val Arg Leu Arg Ala Tyr Met Asn Thr Pro Gly Leu Pro Val Cys Gln
            1540                1545                1550

Asp His Leu Glu Phe Trp Glu Gly Val Phe Thr Gly Leu Thr His Ile
            1555                1560                1565

Asp Ala His Phe Leu Ser Gln Thr Lys Gln Ser Gly Glu Asn Leu Pro
            1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
            1620                1625                1630

Asn Glu Ile Thr Leu Thr His Pro Val Thr Lys Tyr Ile Met Thr Cys
            1635                1640                1645

Met Ser Ala Asp Leu Glu Val Val Thr Ser Thr Trp Val Leu Val Gly
            1650                1655                1660

Gly Val Leu Ala Ala Leu Ala Ala Tyr Cys Leu Ser Thr Gly Cys Val
1665                1670                1675                1680

Val Ile Val Gly Arg Val Val Leu Ser Gly Lys Pro Ala Ile Ile Pro
            1685                1690                1695

Asp Arg Glu Val Leu Tyr Arg Glu Phe Asp Glu Met Glu Glu Cys Ser
            1700                1705                1710

Gln His Leu Pro Tyr Ile Glu Gln Gly Met Met Leu Ala Glu Gln Phe
            1715                1720                1725

Lys Gln Lys Ala Leu Gly Leu Leu Gln Thr Ala Ser Arg Gln Ala Glu
            1730                1735                1740

Val Ile Ala Pro Ala Val Gln Thr Asn Trp Gln Lys Leu Glu Thr Phe
1745                1750                1755                1760
```

```
Trp Ala Lys His Met Trp Asn Phe Ile Ser Gly Ile Gln Tyr Leu Ala
            1765                1770                1775

Gly Leu Ser Thr Leu Pro Gly Asn Pro Ala Ile Ala Ser Leu Met Ala
        1780                1785                1790

Phe Thr Ala Ala Val Thr Ser Pro Leu Thr Thr Ser Gln Thr Leu Leu
    1795                1800                1805

Phe Asn Ile Leu Gly Gly Trp Val Ala Ala Gln Leu Ala Ala Pro Gly
1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Ile Asp Ile Leu Ala Gly Tyr Gly
            1845                1850                1855

Ala Gly Val Ala Gly Ala Leu Val Ala Phe Lys Ile Met Ser Gly Glu
        1860                1865                1870

Val Pro Ser Thr Glu Asp Leu Val Asn Leu Leu Pro Ala Ile Leu Ser
    1875                1880                1885

Pro Gly Ala Leu Val Val Gly Val Val Cys Ala Ala Ile Leu Arg Arg
1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
            1925                1930                1935

Glu Ser Asp Ala Ala Ala Arg Val Thr Ala Ile Leu Ser Ser Leu Thr
        1940                1945                1950

Val Thr Gln Leu Leu Arg Arg Leu His Gln Trp Ile Ser Ser Glu Cys
    1955                1960                1965

Thr Thr Pro Cys Ser Gly Ser Trp Leu Arg Asp Ile Trp Asp Trp Ile
    1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Lys
            2005                2010                2015

Gly Val Trp Arg Val Asp Gly Ile Met His Thr Arg Cys His Cys Gly
        2020                2025                2030

Ala Glu Ile Thr Gly His Val Lys Asn Gly Thr Met Arg Ile Val Gly
    2035                2040                2045

Pro Arg Thr Cys Arg Asn Met Trp Ser Gly Thr Phe Pro Ile Asn Ala
2050                2055                2060

Tyr Thr Thr Gly Pro Cys Thr Pro Leu Pro Ala Pro Asn Tyr Thr Phe
2065                2070                2075                2080

Ala Leu Trp Arg Val Ser Ala Glu Glu Tyr Val Glu Ile Arg Gln Val
            2085                2090                2095

Gly Asp Phe His Tyr Val Thr Gly Met Thr Thr Asp Asn Leu Lys Cys
        2100                2105                2110

Pro Cys Gln Val Pro Ser Pro Glu Phe Phe Thr Glu Leu Asp Gly Val
    2115                2120                2125

Arg Leu His Arg Phe Ala Pro Pro Cys Lys Pro Leu Leu Arg Glu Glu
    2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
            2165                2170                2175

Asp Pro Ser His Ile Thr Ala Glu Ala Ala Gly Arg Arg Leu Ala Arg
```

-continued

```
                2180                2185                2190
Gly Ser Pro Pro Ser Val Ala Ser Ser Ala Ser Gln Leu Ser Ala
            2195                2200                2205
Pro Ser Leu Lys Ala Thr Cys Thr Ala Asn His Asp Ser Pro Asp Ala
    2210                2215                2220
Glu Leu Ile Glu Ala Asn Leu Leu Trp Arg Gln Glu Met Gly Gly Asn
2225                2230                2235                2240
Ile Thr Arg Val Glu Ser Glu Asn Lys Val Val Ile Leu Asp Ser Phe
            2245                2250                2255
Asp Pro Leu Val Ala Glu Glu Asp Glu Arg Glu Ile Ser Val Pro Ala
            2260                2265                2270
Glu Ile Leu Arg Lys Ser Arg Arg Phe Ala Gln Ala Leu Pro Val Trp
            2275                2280                2285
Ala Arg Pro Asp Tyr Asn Pro Pro Leu Val Glu Thr Trp Lys Lys Pro
            2290                2295                2300
Asp Tyr Glu Pro Pro Val Val His Gly Cys Pro Leu Pro Pro Pro Lys
2305                2310                2315                2320
Ser Pro Pro Val Pro Pro Arg Lys Lys Arg Thr Val Val Leu Thr
            2325                2330                2335
Glu Ser Thr Leu Ser Thr Ala Leu Ala Glu Leu Ala Thr Arg Ser Phe
            2340                2345                2350
Gly Ser Ser Ser Thr Ser Gly Ile Thr Gly Asp Asn Thr Thr Thr Ser
            2355                2360                2365
Ser Glu Pro Ala Pro Ser Gly Cys Pro Pro Asp Ser Asp Ala Glu Ser
        2370                2375                2380
Tyr Ser Ser Met Pro Pro Leu Glu Gly Glu Pro Gly Asp Pro Asp Leu
2385                2390                2395                2400
Ser Asp Gly Ser Trp Ser Thr Val Ser Ser Glu Ala Asn Ala Glu Asp
            2405                2410                2415
Val Val Cys Cys Ser Met Ser Tyr Ser Trp Thr Gly Ala Leu Val Thr
            2420                2425                2430
Pro Cys Ala Ala Glu Glu Gln Lys Leu Pro Ile Asn Ala Leu Ser Asn
        2435                2440                2445
Ser Leu Leu Arg His His Asn Leu Val Tyr Ser Thr Thr Ser Arg Ser
    2450                2455                2460
Ala Cys Gln Arg Gln Lys Lys Val Thr Phe Asp Arg Leu Gln Val Leu
2465                2470                2475                2480
Asp Ser His Tyr Gln Asp Val Leu Lys Glu Val Lys Ala Ala Ala Ser
            2485                2490                2495
Lys Val Lys Ala Asn Leu Leu Ser Val Glu Glu Ala Cys Ser Leu Thr
            2500                2505                2510
Pro Pro His Ser Ala Lys Ser Lys Phe Gly Tyr Gly Ala Lys Asp Val
        2515                2520                2525
Arg Cys His Ala Arg Lys Ala Val Thr His Ile Asn Ser Val Trp Lys
    2530                2535                2540
Asp Leu Leu Glu Asp Asn Val Thr Pro Ile Asp Thr Thr Ile Met Ala
2545                2550                2555                2560
Lys Asn Glu Val Phe Cys Val Gln Pro Glu Lys Gly Gly Arg Lys Pro
            2565                2570                2575
Ala Arg Leu Ile Val Phe Pro Asp Leu Gly Val Arg Val Cys Glu Lys
            2580                2585                2590
Met Ala Leu Tyr Asp Val Val Thr Lys Leu Pro Leu Ala Val Met Gly
            2595                2600                2605
```

```
Ser Ser Tyr Gly Phe Gln Tyr Ser Pro Gly Gln Arg Val Glu Phe Leu
    2610                2615                2620
Val Gln Ala Trp Lys Ser Lys Lys Thr Pro Met Gly Phe Ser Tyr Asp
2625                2630                2635                2640
Thr Arg Cys Phe Asp Ser Thr Val Thr Glu Ser Asp Ile Arg Thr Glu
                2645                2650                2655
Glu Ala Ile Tyr Gln Cys Cys Asp Leu Asp Pro Gln Ala Arg Val Ala
                2660                2665                2670
Ile Lys Ser Leu Thr Glu Arg Leu Tyr Val Gly Gly Pro Leu Thr Asn
                2675                2680                2685
Ser Arg Gly Glu Asn Cys Gly Tyr Arg Arg Cys Arg Ala Ser Gly Val
    2690                2695                2700
Leu Thr Thr Ser Cys Gly Asn Thr Leu Thr Cys Tyr Ile Lys Ala Arg
2705                2710                2715                2720
Ala Ala Cys Arg Ala Ala Gly Leu Gln Asp Cys Thr Met Leu Val Cys
                2725                2730                2735
Gly Asp Asp Leu Val Val Ile Cys Glu Ser Ala Gly Val Gln Glu Asp
                2740                2745                2750
Ala Ala Ser Leu Arg Ala Phe Thr Glu Ala Met Thr Arg Tyr Ser Ala
                2755                2760                2765
Pro Pro Gly Asp Pro Pro Gln Pro Glu Tyr Asp Leu Glu Leu Ile Thr
    2770                2775                2780
Ser Cys Ser Ser Asn Val Ser Val Ala His Asp Gly Ala Gly Lys Arg
2785                2790                2795                2800
Val Tyr Tyr Leu Thr Arg Asp Pro Thr Thr Pro Leu Ala Arg Ala Ala
                2805                2810                2815
Trp Glu Thr Ala Arg His Thr Pro Val Asn Ser Trp Leu Gly Asn Ile
                2820                2825                2830
Ile Met Phe Ala Pro Thr Leu Trp Ala Arg Met Ile Leu Met Thr His
                2835                2840                2845
Phe Phe Ser Val Leu Ile Ala Arg Asp Gln Leu Glu Gln Ala Leu Asp
                2850                2855                2860
Cys Glu Ile Tyr Gly Ala Cys Tyr Ser Ile Glu Pro Leu Asp Leu Pro
2865                2870                2875                2880
Pro Ile Ile Gln Arg Leu His Gly Leu Ser Ala Phe Ser Leu His Ser
                2885                2890                2895
Tyr Ser Pro Gly Glu Ile Asn Arg Val Ala Ala Cys Leu Arg Lys Leu
                2900                2905                2910
Gly Val Pro Pro Leu Arg Ala Trp Arg His Arg Ala Arg Ser Val Arg
                2915                2920                2925
Ala Arg Leu Leu Ala Arg Gly Gly Arg Ala Ala Ile Cys Gly Lys Tyr
                2930                2935                2940
Leu Phe Asn Trp Ala Val Arg Thr Lys Leu Lys Leu Thr Pro Ile Ala
2945                2950                2955                2960
Ala Ala Gly Gln Leu Asp Leu Ser Gly Trp Phe Thr Ala Gly Tyr Ser
                2965                2970                2975
Gly Gly Asp Ile Tyr His Ser Val Ser His Ala Arg Pro Arg Trp Ile
                2980                2985                2990
Trp Phe Cys Leu Leu Leu Leu Ala Ala Gly Val Gly Ile Tyr Leu Leu
                2995                3000                3005
Pro Asn Arg
    3010
```

(2) INFORMATION FOR SEQ ID NO:11:

(i) SEQUENCE CHARACTERISTICS:
        (A) LENGTH: 3075 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..3063

(xi) SEQUENCE DESCRIPTION: SEQ ID NO:11:

```
ATG GCT ACA AAG GCT GTT TGT GTT TTG AAG GGT GAC GGC CCA GTT CAA      48
Met Ala Thr Lys Ala Val Cys Val Leu Lys Gly Asp Gly Pro Val Gln
 1               5                  10                  15

GGT ATT ATT AAC TTC GAG CAG AAG GAA AGT AAT GGA CCA GTG AAG GTG      96
Gly Ile Ile Asn Phe Glu Gln Lys Glu Ser Asn Gly Pro Val Lys Val
                20                  25                  30

TGG GGA AGC ATT AAA GGA CTG ACT GAA GGC CTG CAT GGA TTC CAT GTT     144
Trp Gly Ser Ile Lys Gly Leu Thr Glu Gly Leu His Gly Phe His Val
            35                  40                  45

CAT GAG TTT GGA GAT AAT ACA GCA GGC TGT ACC AGT GCA GGT CCT CAC     192
His Glu Phe Gly Asp Asn Thr Ala Gly Cys Thr Ser Ala Gly Pro His
        50                  55                  60

TTT AAT CCT CTA TCC AGA AAA CAC GGT GGG CCA AAG GAT GAA GAG AGG     240
Phe Asn Pro Leu Ser Arg Lys His Gly Gly Pro Lys Asp Glu Glu Arg
 65                 70                  75                  80

CAT GTT GGA GAC TTG GGC AAT GTG ACT GCT GAC AAA GAT GGT GTG GCC     288
His Val Gly Asp Leu Gly Asn Val Thr Ala Asp Lys Asp Gly Val Ala
                85                  90                  95

GAT GTG TCT ATT GAA GAT TCT GTG ATC TCA CTC TCA GGA GAC CAT TGC     336
Asp Val Ser Ile Glu Asp Ser Val Ile Ser Leu Ser Gly Asp His Cys
                100                 105                 110

ATC ATT GGC CGC ACA CTG GTG GTC CAT GAA AAA GCA GAT GAC TTG GGC     384
Ile Ile Gly Arg Thr Leu Val Val His Glu Lys Ala Asp Asp Leu Gly
            115                 120                 125

AAA GGT GGA AAT GAA GAA AGT ACA AAG ACA GGA AAC GCT GGA AGT CGT     432
Lys Gly Gly Asn Glu Glu Ser Thr Lys Thr Gly Asn Ala Gly Ser Arg
        130                 135                 140

TTG GCT TGT GGT GTA ATT GGG ATC GCC CAG AAT TTG GAA TTC GGG GCG     480
Leu Ala Cys Gly Val Ile Gly Ile Ala Gln Asn Leu Glu Phe Gly Ala
145                 150                 155                 160

GTG GAC TTT ATC CCT GTG GAG AAC CTA GAG ACA ACC ATG AGG TCC CCG     528
Val Asp Phe Ile Pro Val Glu Asn Leu Glu Thr Thr Met Arg Ser Pro
                165                 170                 175

GTG TTC ACG GAT AAC TCC TCT CCA CCA GTA GTG CCC CAG AGC TTC CAG     576
Val Phe Thr Asp Asn Ser Ser Pro Pro Val Val Pro Gln Ser Phe Gln
                180                 185                 190

GTG GCT CAC CTC CAT GCT CCC ACA GGC AGC GGC AAA AGC ACC AAG GTC     624
Val Ala His Leu His Ala Pro Thr Gly Ser Gly Lys Ser Thr Lys Val
            195                 200                 205

CCG GCT GCA TAT GCA GCT CAG GGC TAT AAG GTG CTA GTA CTC AAC CCC     672
Pro Ala Ala Tyr Ala Ala Gln Gly Tyr Lys Val Leu Val Leu Asn Pro
        210                 215                 220

TCT GTT GCT GCA ACA CTG GGC TTT GGT GCT TAC ATG TCC AAG GCT CAT     720
Ser Val Ala Ala Thr Leu Gly Phe Gly Ala Tyr Met Ser Lys Ala His
225                 230                 235                 240

GGG ATC GAT CCT AAC ATC AGG ACC GGG GTG AGA ACA ATT ACC ACT GGC     768
Gly Ile Asp Pro Asn Ile Arg Thr Gly Val Arg Thr Ile Thr Thr Gly
```

-continued

```
                245                 250                 255
AGC CCC ATC ACG TAC TCC ACC TAC GGC AAG TTC CTT GCC GAC GGC GGG      816
Ser Pro Ile Thr Tyr Ser Thr Tyr Gly Lys Phe Leu Ala Asp Gly Gly
        260                 265                 270

TGC TCG GGG GGC GCT TAT GAC ATA ATA ATT TGT GAC GAG TGC CAC TCC      864
Cys Ser Gly Gly Ala Tyr Asp Ile Ile Ile Cys Asp Glu Cys His Ser
            275                 280                 285

ACG GAT GCC ACA TCC ATC TTG GGC ATC GGC ACT GTC CTT GAC CAA GCA      912
Thr Asp Ala Thr Ser Ile Leu Gly Ile Gly Thr Val Leu Asp Gln Ala
        290                 295                 300

GAG ACT GCG GGG GCG AGA CTG GTT GTG CTC GCC ACC GCC ACC CCT CCG      960
Glu Thr Ala Gly Ala Arg Leu Val Val Leu Ala Thr Ala Thr Pro Pro
305                 310                 315                 320

GGC TCC GTC ACT GTG CCC CAT CCC AAC ATC GAG GAG GTT GCT CTG TCC     1008
Gly Ser Val Thr Val Pro His Pro Asn Ile Glu Glu Val Ala Leu Ser
            325                 330                 335

ACC ACC GGA GAG ATC CCT TTT TAC GGC AAG GCT ATC CCC CTC GAA GTA     1056
Thr Thr Gly Glu Ile Pro Phe Tyr Gly Lys Ala Ile Pro Leu Glu Val
        340                 345                 350

ATC AAG GGG GGG AGA CAT CTC ATC TTC TGT CAT TCA AAG AAG AAG TGC     1104
Ile Lys Gly Gly Arg His Leu Ile Phe Cys His Ser Lys Lys Lys Cys
            355                 360                 365

GAC GAA CTC GCC GCA AAG CTG GTC GCA TTG GGC ATC AAT GCC GTG GCC     1152
Asp Glu Leu Ala Ala Lys Leu Val Ala Leu Gly Ile Asn Ala Val Ala
370                 375                 380

TAC TAC CGC GGT CTT GAC GTG TCC GTC ATC CCG ACC AGC GGC GAT GTT     1200
Tyr Tyr Arg Gly Leu Asp Val Ser Val Ile Pro Thr Ser Gly Asp Val
385                 390                 395                 400

GTC GTC GTG GCA ACC GAT GCC CTC ATG ACC GGC TAT ACC GGC GAC TTC     1248
Val Val Val Ala Thr Asp Ala Leu Met Thr Gly Tyr Thr Gly Asp Phe
            405                 410                 415

GAC TCG GTG ATA GAC TGC AAT ACG TGT GTC ACC CAG ACA GTC GAT TTC     1296
Asp Ser Val Ile Asp Cys Asn Thr Cys Val Thr Gln Thr Val Asp Phe
        420                 425                 430

AGC CTT GAC CCT ACC TTC ACC ATT GAG ACA ATC ACG CTC CCC CAG GAT     1344
Ser Leu Asp Pro Thr Phe Thr Ile Glu Thr Ile Thr Leu Pro Gln Asp
            435                 440                 445

GCT GTC TCC CGC ACT CAA CGT CGG GGC AGG ACT GGC AGG GGG AAG CCA     1392
Ala Val Ser Arg Thr Gln Arg Arg Gly Arg Thr Gly Arg Gly Lys Pro
        450                 455                 460

GGC ATC TAC AGA TTT GTG GCA CCG GGG GAG CGC CCC TCC GGC ATG TTC     1440
Gly Ile Tyr Arg Phe Val Ala Pro Gly Glu Arg Pro Ser Gly Met Phe
465                 470                 475                 480

GAC TCG TCC GTC CTC TGT GAG TGC TAT GAC GCA GGC TGT GCT TGG TAT     1488
Asp Ser Ser Val Leu Cys Glu Cys Tyr Asp Ala Gly Cys Ala Trp Tyr
            485                 490                 495

GAG CTC ACG CCC GCC GAG ACT ACA GTT AGG CTA CGA GCG TAC ATG AAC     1536
Glu Leu Thr Pro Ala Glu Thr Thr Val Arg Leu Arg Ala Tyr Met Asn
        500                 505                 510

ACC CCG GGG CTT CCC GTG TGC CAG GAC CAT CTT GAA TTT TGG GAG GGC     1584
Thr Pro Gly Leu Pro Val Cys Gln Asp His Leu Glu Phe Trp Glu Gly
            515                 520                 525

GTC TTT ACA GGC CTC ACT CAT ATA GAT GCC CAC TTT CTA TCC CAG ACA     1632
Val Phe Thr Gly Leu Thr His Ile Asp Ala His Phe Leu Ser Gln Thr
        530                 535                 540

AAG CAG AGT GGG GAG AAC CTT CCT TAC CTG GTA GCG TAC CAA GCC ACC     1680
Lys Gln Ser Gly Glu Asn Leu Pro Tyr Leu Val Ala Tyr Gln Ala Thr
545                 550                 555                 560

GTG TGC GCT AGG GCT CAA GCC CCT CCC CCA TCG TGG GAC CAG ATG TGG     1728
```

```
                                                                    -continued Val Cys Ala Arg Ala Gln Ala Pro Pro Ser Trp Asp Gln Met Trp
            565                 570                 575

AAG TGT TTG ATT CGC CTC AAG CCC ACC CTC CAT GGG CCA ACA CCC CTG       1776
Lys Cys Leu Ile Arg Leu Lys Pro Thr Leu His Gly Pro Thr Pro Leu
            580                 585                 590

CTA TAC AGA CTG GGC GCT GTT CAG AAT GAA ATC ACC CTG ACG CAC CCA       1824
Leu Tyr Arg Leu Gly Ala Val Gln Asn Glu Ile Thr Leu Thr His Pro
            595                 600                 605

GTC ACC AAA TAC ATC ATG ACA TGC ATG TCG GCC GAC CTG GAG GTC GTC       1872
Val Thr Lys Tyr Ile Met Thr Cys Met Ser Ala Asp Leu Glu Val Val
            610                 615                 620

ACG AGC ACC TGG GTG CTC GTT GGC GGC GTC CTG GCT GCT TTG GCC GCG       1920
Thr Ser Thr Trp Val Leu Val Gly Gly Val Leu Ala Ala Leu Ala Ala
625                 630                 635                 640

TAT TGC CTG TCA ACA GGC TGC GTG GTC ATA GTG GGC AGG GTC GTC TTG       1968
Tyr Cys Leu Ser Thr Gly Cys Val Val Ile Val Gly Arg Val Val Leu
                    645                 650                 655

TCC GGG AAG CCG GCA ATC ATA CCT GAC AGG GAA GTC CTC TAC CGA GAG       2016
Ser Gly Lys Pro Ala Ile Ile Pro Asp Arg Glu Val Leu Tyr Arg Glu
                660                 665                 670

TTC GAT GAG ATG GAA GAG TGC TCT CAG CAC TTA CCG TAC ATC GAG CAA       2064
Phe Asp Glu Met Glu Glu Cys Ser Gln His Leu Pro Tyr Ile Glu Gln
            675                 680                 685

GGG ATG ATG CTC GCC GAG CAG TTC AAG CAG AAG GCC CTC GGC CTC CTG       2112
Gly Met Met Leu Ala Glu Gln Phe Lys Gln Lys Ala Leu Gly Leu Leu
            690                 695                 700

CAG ACC GCG TCC CGT CAG GCA GAG GTT ATC GCC CCT GCT GTC CAG ACC       2160
Gln Thr Ala Ser Arg Gln Ala Glu Val Ile Ala Pro Ala Val Gln Thr
705                 710                 715                 720

AAC TGG CAA AAA CTC GAG ACC TTC TGG GCG AAG CAT ATG TGG AAC TTC       2208
Asn Trp Gln Lys Leu Glu Thr Phe Trp Ala Lys His Met Trp Asn Phe
                725                 730                 735

ATC AGT GGG ATA CAA TAC TTG GCG GGC TTG TCA ACG CTG CCT GGT AAC       2256
Ile Ser Gly Ile Gln Tyr Leu Ala Gly Leu Ser Thr Leu Pro Gly Asn
            740                 745                 750

CCC GCC ATT GCT TCA TTG ATG GCT TTT ACA GCT GCT GTC ACC AGC CCA       2304
Pro Ala Ile Ala Ser Leu Met Ala Phe Thr Ala Ala Val Thr Ser Pro
            755                 760                 765

CTA ACC ACT AGC CAA ACC CTC CTC TTC AAC ATA TTG GGG GGG TGG GTG       2352
Leu Thr Thr Ser Gln Thr Leu Leu Phe Asn Ile Leu Gly Gly Trp Val
            770                 775                 780

GCT GCC CAG CTC GCC GCC CCC GGT GCC GCT ACT GCC TTT GTG GGC GCT       2400
Ala Ala Gln Leu Ala Ala Pro Gly Ala Ala Thr Ala Phe Val Gly Ala
785                 790                 795                 800

GGC TTA GCT GGC GCC GCC ATC GGC AGT GTT GGA CTG GGG AAG GTC CTC       2448
Gly Leu Ala Gly Ala Ala Ile Gly Ser Val Gly Leu Gly Lys Val Leu
                805                 810                 815

ATA GAC ATC CTT GCA GGG TAT GGC GCG GGC GTG GCG GGA GCT CTT GTG       2496
Ile Asp Ile Leu Ala Gly Tyr Gly Ala Gly Val Ala Gly Ala Leu Val
            820                 825                 830

GCA TTC AAG ATC ATG AGC GGT GAG GTC CCC TCC ACG GAG GAC CTG GTC       2544
Ala Phe Lys Ile Met Ser Gly Glu Val Pro Ser Thr Glu Asp Leu Val
            835                 840                 845

AAT CTA CTG CCC GCC ATC CTC TCG CCC GGA GCC CTC GTA GTC GGC GTG       2592
Asn Leu Leu Pro Ala Ile Leu Ser Pro Gly Ala Leu Val Val Gly Val
            850                 855                 860

GTC TGT GCA GCA ATA CTC GCC CGG CAC GTT GGC CCA GGC GAG GGG GCA       2640
Val Cys Ala Ala Ile Leu Arg Arg His Val Gly Pro Gly Glu Gly Ala
865                 870                 875                 880
```

```
GTG CAG TGG ATG AAC CGG CTG ATA GCC TTC GCC TCA CGG GGG AAC CAT         2688
Val Gln Trp Met Asn Arg Leu Ile Ala Phe Ala Ser Arg Gly Asn His
                885                 890                 895

GTT TCA CCC GGG AAT TCC AGC ACG AAT CCT AAA CCT CAA AAA AAA AAC         2736
Val Ser Pro Gly Asn Ser Ser Thr Asn Pro Lys Pro Gln Lys Lys Asn
        900                 905                 910

AAA CGT AAC ACC AAC CGT CGC CCA CAG GAC GTC AAG TTC CCG GGT GGC         2784
Lys Arg Asn Thr Asn Arg Arg Pro Gln Asp Val Lys Phe Pro Gly Gly
            915                 920                 925

GGT CAG ATC GTT GGT GGA GTT TAC TTG TTG CCG CGC AGG GGC CCT AGA         2832
Gly Gln Ile Val Gly Gly Val Tyr Leu Leu Pro Arg Arg Gly Pro Arg
        930                 935                 940

TTG GGT GTG CGC GCG ACG AGA AAG ACT TCC GAG CGG TCG CAA CCT CGA         2880
Leu Gly Val Arg Ala Thr Arg Lys Thr Ser Glu Arg Ser Gln Pro Arg
945                 950                 955                 960

GGT AGA CGT CAG CCT ATC CCC AAG GCT CGT CGG CCC GAG GGC AGG ACC         2928
Gly Arg Arg Gln Pro Ile Pro Lys Ala Arg Arg Pro Glu Gly Arg Thr
                965                 970                 975

TGG GCT CAG CCC GGG TAC CCT TGG CCC CTC TAT GGC AAT GAG GGC TGC         2976
Trp Ala Gln Pro Gly Tyr Pro Trp Pro Leu Tyr Gly Asn Glu Gly Cys
            980                 985                 990

GGG TGG GCG GGA TGG CTC CTG TCT CCC CGT GGC TCT CGG CCT AGC TGG         3024
Gly Trp Ala Gly Trp Leu Leu Ser Pro Arg Gly Ser Arg Pro Ser Trp
        995                 1000                1005

GGC CCC ACA GAC CCC CGG CGT AGG TCG CGC AAT TTG GGT TAATGAGTCG          3073
Gly Pro Thr Asp Pro Arg Arg Arg Ser Arg Asn Leu Gly
    1010                1015                1020

AC                                                                      3075

(2) INFORMATION FOR SEQ ID NO:12:

(i) SEQUENCE CHARACTERISTICS:
        (A) LENGTH: 1021 amino acids
        (B) TYPE: amino acid
        (D) TOPOLOGY: linear (ii) MOLECULE TYPE: protein (xi) SEQUENCE DESCRIPTION: SEQ ID NO:12:

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Asn Leu Glu Phe Gly Ala
145                 150                 155                 160
```

-continued

```
Val Asp Phe Ile Pro Val Glu Asn Leu Glu Thr Thr Met Arg Ser Pro
                165                 170                 175
Val Phe Thr Asp Asn Ser Ser Pro Pro Val Val Pro Gln Ser Phe Gln
                180                 185                 190
Val Ala His Leu His Ala Pro Thr Gly Ser Gly Lys Ser Thr Lys Val
                195                 200                 205
Pro Ala Ala Tyr Ala Ala Gln Gly Tyr Lys Val Leu Val Leu Asn Pro
                210                 215                 220
Ser Val Ala Ala Thr Leu Gly Phe Gly Ala Tyr Met Ser Lys Ala His
225                 230                 235                 240
Gly Ile Asp Pro Asn Ile Arg Thr Gly Val Arg Thr Ile Thr Thr Gly
                245                 250                 255
Ser Pro Ile Thr Tyr Ser Thr Tyr Gly Lys Phe Leu Ala Asp Gly Gly
                260                 265                 270
Cys Ser Gly Gly Ala Tyr Asp Ile Ile Ile Cys Asp Glu Cys His Ser
                275                 280                 285
Thr Asp Ala Thr Ser Ile Leu Gly Ile Gly Thr Val Leu Asp Gln Ala
                290                 295                 300
Glu Thr Ala Gly Ala Arg Leu Val Val Leu Ala Thr Ala Thr Pro Pro
305                 310                 315                 320
Gly Ser Val Thr Val Pro His Pro Asn Ile Glu Val Ala Leu Ser
                325                 330                 335
Thr Thr Gly Glu Ile Pro Phe Tyr Gly Lys Ala Ile Pro Leu Glu Val
                340                 345                 350
Ile Lys Gly Gly Arg His Leu Ile Phe Cys His Ser Lys Lys Lys Cys
                355                 360                 365
Asp Glu Leu Ala Ala Lys Leu Val Ala Leu Gly Ile Asn Ala Val Ala
370                 375                 380
Tyr Tyr Arg Gly Leu Asp Val Ser Val Ile Pro Thr Ser Gly Asp Val
385                 390                 395                 400
Val Val Val Ala Thr Asp Ala Leu Met Thr Gly Tyr Thr Gly Asp Phe
                405                 410                 415
Asp Ser Val Ile Asp Cys Asn Thr Cys Val Thr Gln Thr Val Asp Phe
                420                 425                 430
Ser Leu Asp Pro Thr Phe Thr Ile Glu Thr Ile Thr Leu Pro Gln Asp
                435                 440                 445
Ala Val Ser Arg Thr Gln Arg Arg Gly Arg Thr Gly Arg Gly Lys Pro
                450                 455                 460
Gly Ile Tyr Arg Phe Val Ala Pro Gly Glu Arg Pro Ser Gly Met Phe
465                 470                 475                 480
Asp Ser Ser Val Leu Cys Glu Cys Tyr Asp Ala Gly Cys Ala Trp Tyr
                485                 490                 495
Glu Leu Thr Pro Ala Glu Thr Thr Val Arg Leu Arg Ala Tyr Met Asn
                500                 505                 510
Thr Pro Gly Leu Pro Val Cys Gln Asp His Leu Glu Phe Trp Glu Gly
                515                 520                 525
Val Phe Thr Gly Leu Thr His Ile Asp Ala His Phe Leu Ser Gln Thr
                530                 535                 540
Lys Gln Ser Gly Glu Asn Leu Pro Tyr Leu Val Ala Tyr Gln Ala Thr
545                 550                 555                 560
Val Cys Ala Arg Ala Gln Ala Pro Pro Ser Trp Asp Gln Met Trp
                565                 570                 575
```

-continued

```
Lys Cys Leu Ile Arg Leu Lys Pro Thr Leu His Gly Pro Thr Pro Leu
            580                 585                 590
Leu Tyr Arg Leu Gly Ala Val Gln Asn Glu Ile Thr Leu Thr His Pro
            595                 600                 605
Val Thr Lys Tyr Ile Met Thr Cys Met Ser Ala Asp Leu Glu Val Val
            610                 615                 620
Thr Ser Thr Trp Val Leu Val Gly Gly Val Leu Ala Ala Leu Ala Ala
625                 630                 635                 640
Tyr Cys Leu Ser Thr Gly Cys Val Val Ile Val Gly Arg Val Val Leu
                645                 650                 655
Ser Gly Lys Pro Ala Ile Ile Pro Asp Arg Glu Val Leu Tyr Arg Glu
                660                 665                 670
Phe Asp Glu Met Glu Glu Cys Ser Gln His Leu Pro Tyr Ile Glu Gln
                675                 680                 685
Gly Met Met Leu Ala Glu Gln Phe Lys Gln Lys Ala Leu Gly Leu Leu
                690                 695                 700
Gln Thr Ala Ser Arg Gln Ala Glu Val Ile Ala Pro Ala Val Gln Thr
705                 710                 715                 720
Asn Trp Gln Lys Leu Glu Thr Phe Trp Ala Lys His Met Trp Asn Phe
                725                 730                 735
Ile Ser Gly Ile Gln Tyr Leu Ala Gly Leu Ser Thr Leu Pro Gly Asn
                740                 745                 750
Pro Ala Ile Ala Ser Leu Met Ala Phe Thr Ala Ala Val Thr Ser Pro
                755                 760                 765
Leu Thr Thr Ser Gln Thr Leu Leu Phe Asn Ile Leu Gly Gly Trp Val
770                 775                 780
Ala Ala Gln Leu Ala Ala Pro Gly Ala Ala Thr Ala Phe Val Gly Ala
785                 790                 795                 800
Gly Leu Ala Gly Ala Ala Ile Gly Ser Val Gly Leu Gly Lys Val Leu
                805                 810                 815
Ile Asp Ile Leu Ala Gly Tyr Gly Ala Gly Val Ala Gly Ala Leu Val
                820                 825                 830
Ala Phe Lys Ile Met Ser Gly Glu Val Pro Ser Thr Glu Asp Leu Val
                835                 840                 845
Asn Leu Leu Pro Ala Ile Leu Ser Pro Gly Ala Leu Val Val Gly Val
850                 855                 860
Val Cys Ala Ala Ile Leu Arg Arg His Val Gly Pro Gly Glu Gly Ala
865                 870                 875                 880
Val Gln Trp Met Asn Arg Leu Ile Ala Phe Ala Ser Arg Gly Asn His
                885                 890                 895
Val Ser Pro Gly Asn Ser Ser Thr Asn Pro Lys Pro Gln Lys Lys Asn
                900                 905                 910
Lys Arg Asn Thr Asn Arg Arg Pro Gln Asp Val Lys Phe Pro Gly Gly
                915                 920                 925
Gly Gln Ile Val Gly Gly Val Tyr Leu Leu Pro Arg Arg Gly Pro Arg
                930                 935                 940
Leu Gly Val Arg Ala Thr Arg Lys Thr Ser Glu Arg Ser Gln Pro Arg
945                 950                 955                 960
Gly Arg Arg Gln Pro Ile Pro Lys Ala Arg Arg Pro Glu Gly Arg Thr
                965                 970                 975
Trp Ala Gln Pro Gly Tyr Pro Trp Pro Leu Tyr Gly Asn Glu Gly Cys
                980                 985                 990
```

```
Gly Trp Ala Gly Trp Leu Leu Ser Pro Arg Gly Ser Arg Pro Ser Trp
            995                 1000                1005

Gly Pro Thr Asp Pro Arg Arg Arg Ser Arg Asn Leu Gly
       1010                1015            1020
```